United States Patent
Saitoh et al.

(10) Patent No.: US 7,691,491 B2
(45) Date of Patent: Apr. 6, 2010

(54) MONOAMINOFLUORENE COMPOUND AND ORGANIC LIGHT-EMITTING DEVICE USING THE SAME

(75) Inventors: Akihito Saitoh, Yokohama (JP); Mizuho Hiraoka, Kawasaki (JP); Koichi Suzuki, Yokohama (JP); Akihiro Senoo, Kawasaki (JP); Hiroshi Tanabe, Yokohama (JP); Naoki Yamada, Komae (JP); Chika Negishi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 878 days.

(21) Appl. No.: 10/525,194

(22) PCT Filed: Aug. 12, 2003

(86) PCT No.: PCT/JP03/10260

§ 371 (c)(1),
(2), (4) Date: Feb. 22, 2005

(87) PCT Pub. No.: WO2004/020387

PCT Pub. Date: Mar. 11, 2004

(65) Prior Publication Data

US 2006/0166034 A1 Jul. 27, 2006

(30) Foreign Application Priority Data

Aug. 30, 2002 (JP) ............................. 2002-252846

(51) Int. Cl.
*H01L 51/54* (2006.01)
*C07C 211/00* (2006.01)
*C07D 209/82* (2006.01)
*C07D 221/02* (2006.01)

(52) U.S. Cl. .................. 428/690; 428/917; 313/504; 313/506; 257/E51.051; 564/426; 564/427; 564/429; 564/433; 548/440; 546/94

(58) Field of Classification Search .......... 428/690, 428/917; 313/504, 506; 564/426, 427, 429, 564/433; 548/440; 546/94
See application file for complete search history.

(56) References Cited

U.S. PATENT DOCUMENTS

| 4,539,507 A | 9/1985 | VanSlyke et al. ............. 313/504 |
| 4,720,432 A | 1/1988 | VanSlyke et al. ............. 428/457 |

(Continued)

FOREIGN PATENT DOCUMENTS

EP 0 821 277 A1 1/1998

(Continued)

OTHER PUBLICATIONS

Proceedings of SPIE, (1998), 3472, p. 70-79.*

(Continued)

*Primary Examiner*—Dawn Garrett
(74) *Attorney, Agent, or Firm*—Fitzpatrick, Cella, Harper & Scinto

(57) ABSTRACT

Novel monoaminofluorene compounds are provided, and organic light-emitting devices which exhibit good luminescence hue of extremely high purity and have optical output with high luminescence efficiency, high luminance and longer operating life are provided using the compounds. The monoaminofluorene compound represented by the following general formula [1]:

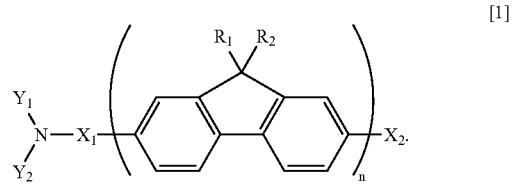

14 Claims, 3 Drawing Sheets

U.S. PATENT DOCUMENTS

| | | | | |
|---|---|---|---|---|
| 4,885,211 | A | 12/1989 | Tang et al. | 428/457 |
| 5,130,303 | A | 7/1992 | Tokailin et al. | 313/504 |
| 5,151,629 | A | 9/1992 | VanSlyke | 313/504 |
| 5,227,252 | A | 7/1993 | Murayama et al. | 428/690 |
| 5,247,190 | A | 9/1993 | Friend et al. | 257/40 |
| 5,317,169 | A | 5/1994 | Nakano et al. | 257/40 |
| 5,382,477 | A | 1/1995 | Saito et al. | 428/690 |
| 5,409,783 | A | 4/1995 | Tang et al. | 428/690 |
| 5,514,878 | A | 5/1996 | Holmes et al. | 257/40 |
| 5,672,678 | A | 9/1997 | Holmes et al. | 528/373 |
| 5,726,457 | A | 3/1998 | Nakano et al. | 257/40 |
| 5,989,737 | A * | 11/1999 | Xie et al. | 428/690 |
| 6,093,864 | A | 7/2000 | Tokailin et al. | 585/25 |
| 6,743,948 | B1 | 6/2004 | Hosokawa et al. | 564/426 |
| 6,916,555 | B2 | 7/2005 | Suzuki et al. | 428/690 |
| 7,241,513 | B2 * | 7/2007 | Suzuki et al. | 428/690 |
| 2003/0039838 | A1 * | 2/2003 | Chen et al. | 428/411.1 |
| 2003/0065190 | A1 | 4/2003 | Spreitzer et al. | 548/134 |
| 2003/0072966 | A1 | 4/2003 | Hosokawa et al. | 428/690 |
| 2004/0253389 | A1 * | 12/2004 | Suzuki et al. | 428/1.1 |
| 2005/0038296 | A1 | 2/2005 | Hosokawa et al. | 564/426 |
| 2005/0106414 | A1 * | 5/2005 | Saitoh et al. | 428/690 |

FOREIGN PATENT DOCUMENTS

| | | |
|---|---|---|
| EP | 1221434 A1 | 10/2002 |
| JP | 02-247278 | 10/1990 |
| JP | 03-255190 | 11/1991 |
| JP | 04-145192 | 5/1992 |
| JP | 09-227576 | 9/1992 |
| JP | 05-202356 | 8/1993 |
| JP | 05-247460 | 9/1993 |
| JP | 7-43920 | 7/1995 |
| JP | 07-281464 | 10/1995 |
| JP | 08-044096 | 2/1996 |
| JP | 09-202878 | 8/1997 |
| JP | 09-281728 | 10/1997 |
| JP | 11-144873 | 5/1999 |
| JP | 11-144875 | 5/1999 |
| JP | 11-184109 | 7/1999 |
| JP | 11-312587 | 11/1999 |
| JP | 2000-327639 | 11/2000 |
| JP | 2001-010996 | 1/2001 |
| JP | 2001-052868 | 2/2001 |
| JP | 2001-66809 | 3/2001 |
| JP | 2001-192651 | 7/2001 |
| JP | 2001-196177 | 7/2001 |
| JP | 2002-8866 | 11/2002 |
| JP | 2003-128651 A * | 5/2003 |
| WO | 97/33323 | 9/1997 |
| WO | 99/40655 | 8/1999 |
| WO | WO 00/39247 * | 7/2000 |
| WO | 2004/020372 A1 | 3/2004 |

OTHER PUBLICATIONS

Chemistry of Materials, (2000), 12(5), pp. 1184-1186.*
Machine generated translation of Description section of JP 2003-128651 A published May 2003.*
Machine generated translation of Examples section of JP 2003-128651 A published May 2003.*
Machine generated translation of Claims section of JP 2003-128651 A published May 2003.*
Tang, et al; "Organic Electroluminescent Devices"; Appl. Phys. Lett. vol. 51, No. 12, pp. 913-915 (1987).
Burroughes, et al; Light-emitting diodes based on conjugated polymers; Nature, vol. 347, pp. 539-541 (1990).
Kelley et al., "Synthesis of Bridged Oligophenylenes from Fluorene", J. Chem. Research (S),1997, 446-447.

* cited by examiner

MONOAMINOFLUORENE COMPOUND AND ORGANIC LIGHT-EMITTING DEVICE USING THE SAME

TECHNICAL FIELD

The present invention relates to a monoaminofluorene compound and an organic light-emitting device, more particularly to a light-emitting device using an organic compound which emits light by applying an electric field to a thin film of the organic compound.

BACKGROUND ART

An organic light-emitting device is a device having a thin film containing a fluorescent organic compound interposed between an anode and a cathode, in which excitons of the fluorescent compound are generated by injecting electrons and holes (positive holes) from each electrode into the compound and the light emitted when these excitons return to the ground state is utilized.

In a research by Eastman Kodak Company in 1987 (Appl. Phys. Lett. 51, 913 (1987)), luminescence on the order of 1000 $cd/m^2$ upon application of voltage on the order of 10 V was reported in relation to a device having a function separate type two-layer structure using ITO for the anode, and magnesium silver alloy for the cathode, respectively, and using aluminum quinolinol complex as an electron-transporting material as well as a light-emitting material and triphenylamine derivative as a hole-transporting material. Relevant patents include U.S. Pat. Nos. 4,539,507, 4,720,432, 4,885,211, etc.

Moreover, luminescence ranging from ultraviolet to infrared rays can be obtained by changing the kind of fluorescent organic compound, and, recently, studies on various compounds are actively conducted. For example, such studies are described in U.S. Pat. Nos. 5,151,629, 5,409,783, 5,382,477, Japanese Patent Application Laid-Open No. 2-247278, Japanese Patent Application Laid-Open No. 3-255190, Japanese Patent Application Laid-Open No. 5-202356, Japanese Patent Application Laid-Open No. 9-202878, Japanese Patent Application Laid-Open No. 9-227576, etc.

In addition to the organic light-emitting devices using low molecular materials as mentioned above, an organic light-emitting device using a conjugated polymer was reported by a group in Cambridge University (Nature, 347, 539 (1990)). This report confirms that luminescence occurs in a single layer film which is formed of poly(phenylene vinylene) (PPV) using a coating system. Related patents of the organic light-emitting device using conjugated polymer include U.S. Pat. Nos. 5,247,190, 5,514,878, 5,672,678, Japanese Patent Application Laid-Open No. 4-145192, Japanese Patent Application Laid-Open No. 5-247460, etc.

The latest progress in the organic light-emitting device is remarkable in this way, and the features thereof facilitate production of light-emitting devices imparted with high luminance at low applied voltage, diversity of luminescence wavelength, high-speed response, thin shape and lightweight, thereby suggesting possibility for a wide variety of applications.

However, there still remain many problems in respect of durability, such as change with the passage of time by prolonged use, degradation by atmospheric gas containing oxygen, humidity, etc. Furthermore, when the application to a full color display and the like is envisaged, optical output of further higher luminance or higher conversion efficiency, and luminescence in blue, green and red of high color purity are required under the present condition.

For example, although diamine compounds as a luminescent material were disclosed in Japanese Patent Application Laid-Open No. 2001-52868, blue luminescence of high color purity (chromaticity coordinate: x, y=0.14-0.15, 0.09-0.10) was not obtained. An example using a compound having the similar diamino structure was also disclosed in Japanese Patent Application Laid-Open No. 2001-196177, but the compound was used as a hole injection layer, and there was no description of the use as a light-emitting layer and light-emitting properties thereof such as luminescence color and efficiency.

DISCLOSURE OF THE INVENTION

The present invention has been made to solve these problems of the prior art, and an object of the present invention is to provide a novel monoamino compound.

Another object of the present invention is to provide an organic light-emitting device exhibiting good luminescence hue of extremely high purity and high luminance optical output with a high efficiency and a longer operating life.

Still another object of the present invention is to provide an organic light-emitting device which can be readily manufactured at relatively low cost.

The inventors of the present invention conducted intensive study in order to solve the above-mentioned problems and came to complete the present invention.

That is, the monoaminofluorene compound of the present invention is characterized in that it is represented by the following general formula [1] or [2].

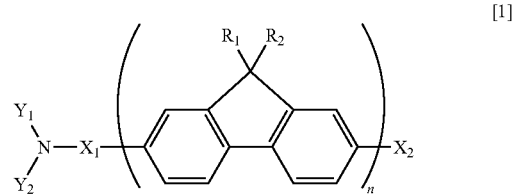

[1]

wherein $X_1$ is a divalent group selected from the group consisting of substituted or unsubstituted alkylene, aralkylene, arylene and heterocyclic ring groups, and alkylene, aralkylene, alkenylene, amino, silyl, carbonyl, ether and thioether groups having a linking group consisting of a substituted or unsubstituted arylene or divalent heterocyclic ring group, or $X_1$ may be a direct bond;

$X_2$ is a group selected from the group consisting of a hydrogen atom, a halogen group, substituted or unsubstituted alkyl, aralkyl, alkenyl, alkynyl, alkoxy, aryl, heterocyclic ring and sulfide groups, a substituted silyl group and a cyano group;

$Y_1$ and $Y_2$ may be the same or different and are groups selected from the group consisting of substituted or unsubstituted alkyl, aralkyl, aryl and heterocyclic ring groups, substituted or unsubstituted alkylene, aralkylene, alkenylene, amino and silyl groups having a linking group consisting of a substituted or unsubstituted arylene or divalent heterocyclic ring group, and unsubstituted carbonyl, ether and thioether groups having a linking group consisting of a substituted or unsubstituted arylene or divalent heterocyclic ring group;

$Y_1$ and $Y_2$, or $X_1$, $Y_1$ and $Y_2$ may also join together to form a ring;

$R_1$ and $R_2$ may be the same or different and are groups selected from the group consisting of a hydrogen atom, and substituted or unsubstituted alkyl, aralkyl and aryl groups; and n is an integer of 2 to 10 when $X_1$ is a direct bond and $X_2$ is a hydrogen atom, and otherwise an integer of 1 to 10.

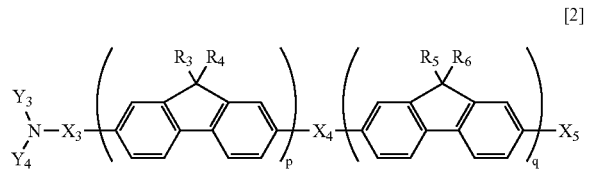

[2]

wherein $X_3$ and $X_4$ may be the same or different and are divalent groups selected from the group consisting of a substituted or unsubstituted alkylene, aralkylene, arylene and heterocyclic ring groups, substituted or unsubstituted alkylene, aralkylene, alkenylene, amino and silyl groups having a linking group consisting of a substituted or unsubstituted arylene or divalent heterocyclic ring group, unsubstituted carbonyl, ether and thioether groups, or $X_3$ may be a direct bond;

$X_5$ is a group selected from the group consisting of a hydrogen atom, a halogen group, substituted or unsubstituted alkyl, aralkyl, alkenyl, alkynyl, alkoxy, aryl, heterocyclic ring and sulfide groups, a substituted silyl group, and a cyano group;

$Y_3$ and $Y_4$ may be the same or different and are groups selected from the group consisting of substituted or unsubstituted alkyl, aralkyl, aryl and heterocyclic ring groups, substituted or unsubstituted alkylene, aralkylene, alkenylene, amino and silyl groups having a linking group consisting of a substituted or unsubstituted arylene or divalent heterocyclic ring group, and unsubstituted carbonyl, ether and thioether groups having a linking group consisting of a substituted or unsubstituted arylene or divalent heterocyclic ring group;

$Y_3$ and $Y_4$, or $X_3$, $Y_3$ and $Y_4$ may also join together to form a ring;

$R_3$ to $R_6$ may be the same or different and are groups selected from the group consisting of a hydrogen atom, and substituted or unsubstituted alkyl, aralkyl and aryl groups; and each of p and q is an integer not less than one and p+q is an integer of 2 to 10.

In the organic light-emitting device of the present invention comprising a pair of electrodes which consist of an anode and a cathode and one or more layers which are interposed between the electrodes and contain an organic compound, the at least one layer containing the organic compound preferably contains at least one compound represented by the above-mentioned general formula [1] or [2].

BEST MODE FOR CARRYING OUT THE INVENTION

Figure 1:
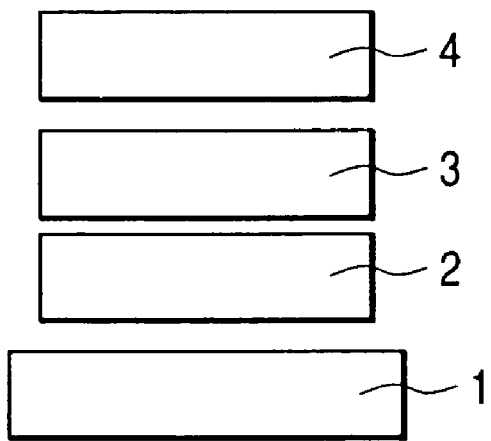
FIG. 1 is a cross-sectional view showing an example of the organic light-emitting device according to the present invention.

The present invention will be described in detail below.

The monoaminofluorene compound of the present invention is described first.

The monoaminofluorene compound of the present invention is represented by the above-mentioned general formula [1] or [2].

The monoaminofluorene compound of the present invention can mainly be used as an organic light-emitting device material, and when it is used as a light-emitting device material, devices having high color purity, high luminescence efficiency and a longer operating life can respectively be obtained even in a single layer. Furthermore, a luminescence spectrum with a narrower half-value width, i.e., luminescence more excellent in color purity is obtained by introducing fluorene having a rigid structure into the main chain of the molecule. Furthermore, since the Stokes shift is suppressed, a shift of the luminescence wavelength is suppressed, and it is also possible to shift the absorption even toward a longer wavelength side, and when it is used as a dopant material, use of a host material which has a luminescence spectrum in a relatively longer wavelength side is also enabled.

Each of the monoaminofluorene compounds of the present invention can be used for the purpose of both dopant material and host material in a light-emitting layer to provide a device having high color purity, high luminescence efficiency, and longer operating life, and in particular can be used as a dopant material in combination with a suitable host material of easily causing energy transfer to provide a device holding high color purity luminescence and having higher efficiency.

Specific examples of the substituents in the above-mentioned general formulae [1] and [2] are shown below.

Examples of the substituted or unsubstituted linear or cyclic alkyl group include methyl group, ethyl group, n-propyl group, n-butyl group, n-hexyl group, n-decyl group, iso-propyl group, iso-butyl group, tert-butyl group, tert-octyl group, trifluoromethyl group, cyclohexyl group, cyclohexylmethyl group, but, of course, are not limited to these.

Examples of the substituted or unsubstituted aralkyl group include benzyl group, phenethyl group, but, of course, are not limited to these.

Examples of the substituted or unsubstituted aryl group include phenyl group, 4-methylphenyl group, 4-methoxyphenyl group, 4-ethylphenyl group, 4-fluorophenyl group, 3,5-dimethylphenyl group, triphenylamino group, biphenyl group, terphenyl group, naphthyl group, anthracenyl group, phenanthrenyl group, pyrenyl group, tetracenyl group, pentacenyl group, fluorenyl group, triphenylenyl group, perylenyl group, but, of course, are not limited to these.

Examples of the substituted or unsubstituted heterocyclic ring group include pyrrolyl group, pyridyl group, bipyridyl group, methylpyridyl group, terpyrrolyl group, thienyl group, terthienyl group, propyl thienyl group, furyl group, quinolyl group, carbazolyl group, oxazolyl group, oxadiazolyl group, thiazolyl group, thiadiazolyl group, but, of course, are not limited to these.

Examples of the substituted or unsubstituted alkylene group include methylene group, ethylene group, propylene group, iso-propylene group, butylene group, tert-butylene group, hexylene group, heptylene group, cyclohexylene group, cyclohexylmethylene group, but, of course, are not limited to these.

Examples of the substituted or unsubstituted aralkylene group include benzylene group, phenylethylene group, phenethylene group, but, of course, are not limited to these.

Examples of the substituted or unsubstituted arylene group include phenylene group, biphenylene group, 2,3,5,6-tetrafluorophenylene group, 2,5-dimethylphenylene group, naphtylene group, anthracenylene group, phenanthrenylene group, tetracenylene group, pentacenylene group, perylenylene group, but, of course, are not limited to these.

Examples of the substituted or unsubstituted divalent heterocyclic ring group include furanylene group, pyrrolylene group, pyridinylene group, terpyridinylene group, thiophenylene group, terthiophenylene group, oxazolylene group, thiazolylene group, carbazolylene, but, of course, are not limited to these.

Examples of the substituted or unsubstituted alkenyl group include vinyl group, allyl group (2-propenyl group), 1-propenyl group, iso-propenyl group, 2-butenyl group, but, of course, are not limited to these.

Examples of the substituted or unsubstituted amino group include amino group, methylamino group, ethylamino group, dimethylamino group, diethylamino group, methylethylamino group, benzylamino group, methylbenzylamino group, dibenzylamino group, anilino group, diphenylamino group, phenyltolylamino group, ditolylamino group, dianisolylamino group, but, of course, are not limited to these.

Examples of the substituted or unsubstituted carbonyl group include acetyl group, propionyl group, isobutyryl group, methacryloyl group, benzoyl group, naphtoyl group, anthranyl group, toluoyl group, but, of course, are not limited to these.

Examples of the substituted or unsubstituted alkoxy group include methoxy group, ethoxy group, propoxy group, 2-ethyl-octyloxy group, phenoxy group, 4-butylphenoxy group, benzyloxy group, but, of course, are not limited to these.

Examples of the substituted or unsubstituted sulfide group include methylsulfide group, ethylsulfide group, phenylsulfide group, 4-methylphenylsulfide group, but, of course, are not limited to these.

Examples of the substituent group which the above-mentioned substituent groups may have include alkyl groups such as methyl group, ethyl group, n-propyl group, iso-propyl group, ter-butyl group, octyl group, benzyl group and phenethyl group, an aralkyl group, alkoxy groups such as methoxy group, ethoxy group, propoxy group, 2-ethyl-octyloxy group, phenoxy group, 4-butylphenoxy group and benzyloxy group, aryl groups such as phenyl group, 4-methylphenyl group, 4-ethylphenyl group, 3-chlorophenyl group, 3,5-dimethylphenyl group, triphenylamino group, biphenyl group, terphenyl group, naphthyl group, anthryl group, phenanthryl group and pyrenyl group, a heterocyclic ring group such as pyridyl group, bipyridyl group, methylpyridyl group, thienyl group, terthienyl group, propylthienyl group, furyl group, quinolyl group, carbazolyl group and N-ethylcarbazolyl group, a halogen group, cyano group, and nitro group, but, of course, are not limited to these.

Typical examples of the compound represented by the general formulae [1] and [2] are shown below but are not limited to these compounds.

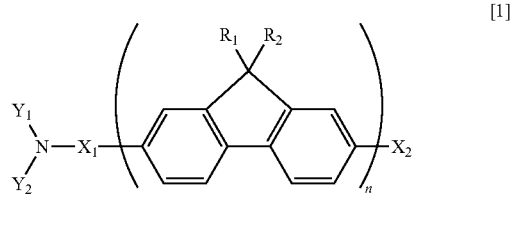

[1]

TABLE 1

|   | n | R1, R2 | X1 | X2 | Y1 | Y2 |
|---|---|--------|----|----|----|----|
| 1 | 1 | Me | Direct bond | Ph | Ph | Ph |
| 2 | 1 | Me | Direct bond | Ph | ―⟨Ph⟩―Me | ―⟨Ph⟩―Me |
| 3 | 1 | Me | Direct bond | Ph | Ph | naphthyl |
| 4 | 1 | Me | Direct bond | Ph | Ph | naphthyl |
| 5 | 1 | Me | Direct bond | Ph | Ph | 9,9-dimethylfluorenyl |

TABLE 1-continued
| | n | R1, R2 | X1 | X2 | Y1 | Y2 |
|---|---|---|---|---|---|---|
| 6 | 1 | Me | Direct bond | Ph | Ph | 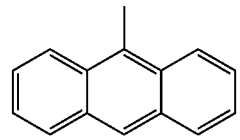 |
| 7 | 1 | Me | Direct bond | Ph | Ph | 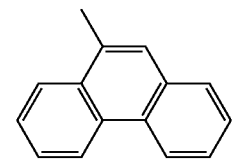 |
| 8 | 1 | Me | Direct bond | Ph | Ph | 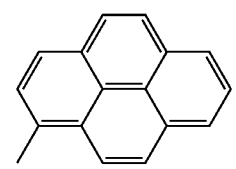 |
| 9 | 1 | Me | Direct bond | 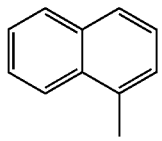 | 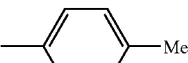 | 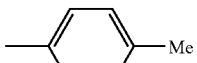 |
| 10 | 1 | Me | Direct bond | 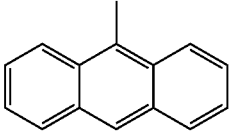 | 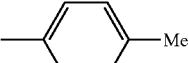 | 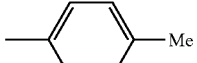 |
| 11 | 1 | Me | Direct bond | 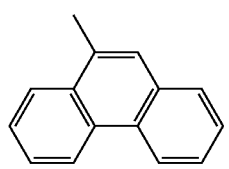 | 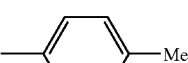 | 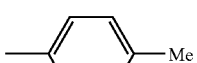 |
| 12 | 1 | Me | Direct bond | 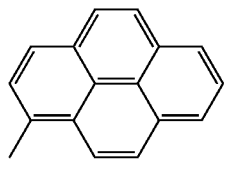 | 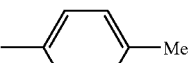 | 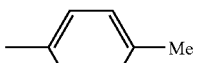 |
| 13 | 1 | Me | 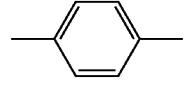 | H | Ph | Ph |
| 14 | 1 | Me | 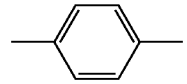 | H | 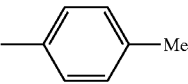 | 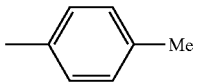 |
| 15 | 1 | Me | 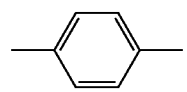 | H | Ph | 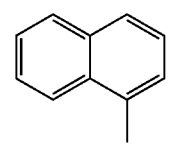 |

TABLE 1-continued

| | n | R1, R2 | X1 | X2 | Y1 | Y2 |
|---|---|---|---|---|---|---|
| 16 | 1 | Me | -C6H4- (para) | H | Ph | 9-methylanthracen-10-yl |
| 17 | 1 | Me | -C6H4- (para) | H | Ph | methylphenanthrenyl |
| 18 | 1 | Me | -C6H4- (para) | H | Ph | methylpyrenyl |
| 19 | 1 | Me | -C6H4- (para) | Ph | Ph | Ph |
| 20 | 1 | Me | -C6H4- (para) | Ph | -C6H4-Me (para) | -C6H4-Me (para) |

TABLE 2

| | n | R1, R2 | X1 | X2 | Y1 | Y2 |
|---|---|---|---|---|---|---|
| 21 | 1 | Me | -C6H4- (para) | Ph | Ph | 2-naphthyl |
| 22 | 1 | Me | -C6H4- (para) | Ph | Ph | 9,9-dimethylfluoren-2-yl |
| 23 | 1 | Me | -C6H4- (para) | 1-naphthyl | -C6H4-Me (para) | -C6H4-Me (para) |
| 24 | 1 | Me | -C6H4- (para) | 9-methylanthracen-10-yl | -C6H4-Me (para) | -C6H4-Me (para) |
| 25 | 1 | Me | -C6H4- (para) | 9-methylanthracen-10-yl | Ph | methylpyrenyl |

TABLE 2-continued

| n | R1, R2 | X1 | X2 | Y1 | Y2 |
|---|---|---|---|---|---|
| 26 | 1 | Me | 1,4-phenylene | 9-phenanthrenyl | 4-methylphenyl | 4-methylphenyl |
| 27 | 1 | Me | 1,4-phenylene | 1-pyrenyl | 4-methylphenyl | 4-methylphenyl |
| 28 | 1 | Me | 1,4-phenylene | 1-pyrenyl | Ph | 1-pyrenyl |
| 29 | 1 | Me | 2,5-dimethyl-1,4-phenylene | H | 4-methylphenyl | 4-methylphenyl |
| 30 | 1 | Me | tetrafluoro-1,4-phenylene | H | 4-methylphenyl | 4-methylphenyl |
| 31 | 1 | Me | tetrafluoro-1,4-phenylene | 9-anthracenyl | 4-methylphenyl | 4-methylphenyl |
| 32 | 1 | Me | 4,4'-oxydiphenylene | H | 4-methylphenyl | 4-methylphenyl |
| 33 | 1 | Me | 1,4-naphthylene | H | 4-methylphenyl | 4-methylphenyl |
| 34 | 1 | Me | 9,10-anthracenylene | H | 4-methylphenyl | 4-methylphenyl |

TABLE 2-continued

| n | R1, R2 | X1 | X2 | Y1 | Y2 |
|---|---|---|---|---|---|
| 35 | 1 | Me | 9,10-dimethylanthracen-diyl | 9-methylanthracen-diyl | -C6H4-Me | -C6H4-Me |
| 36 | 1 | Me | dimethyl-perylenediyl | H | -C6H4-Me | -C6H4-Me |

TABLE 3

| n | R1, R2 | X1 | X2 | Y1 | Y2 |
|---|---|---|---|---|---|
| 37 | 1 | Me | dimethyl-perylenediyl | H | -C6H4-Me | -C6H4-Me |
| 38 | 1 | n-Bu | -C6H4- | H | -C6H4-Me | -C6H4-Me |
| 39 | 1 | n-Bu | -C6H4- | 9-methylanthracen-diyl | -C6H4-Me | -C6H4-Me |
| 40 | 1 | Ph | -C6H4- | H | -C6H4-Me | -C6H4-Me |
| 41 | 1 | Ph | -C6H4- | 9-methylanthracen-diyl | -C6H4-Me | -C6H4-Me |
| 42 | 2 | Me | Direct bond | H | Ph | Ph |
| 43 | 2 | Me | Direct bond | H | -C6H4-Me | -C6H4-Me |
| 44 | 2 | Me | Direct bond | H | -C6H4-Si(Me)2-Ph | -C6H4-Si(Me)2-Ph |
| 45 | 2 | Me | Direct bond | H | Ph | 1-naphthyl |

TABLE 3-continued
| n | R1, R2 | X1 | X2 | Y1 | Y2 |
|---|---|---|---|---|---|
| 46 | 2 | Me | Direct bond | H | Ph | 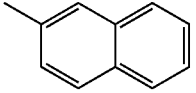 |
| 47 | 2 | Me | Direct bond | H | Ph | 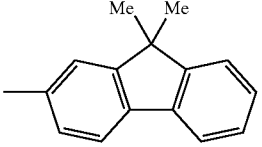 |
| 48 | 2 | Me | Direct bond | H | Ph | 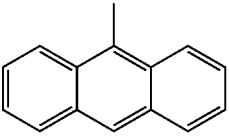 |
| 49 | 2 | Me | Direct bond | H | Ph | 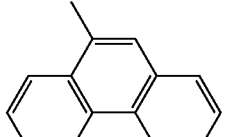 |
| 50 | 2 | Me | Direct bond | H | Ph | 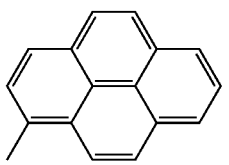 |
| 51 | 2 | Me | Direct bond | Ph | 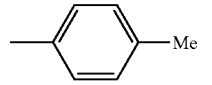 | 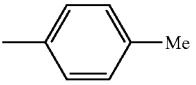 |
| 52 | 2 | Me | Direct bond | Ph | Ph | 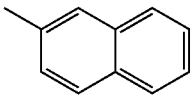 |
| 53 | 2 | Me | Direct bond | Ph | Ph | 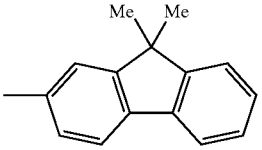 |
| 54 | 2 | Me | Direct bond | Ph | Ph | 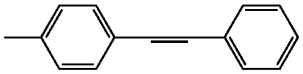 |
| 55 | 2 | Me | Direct bond | 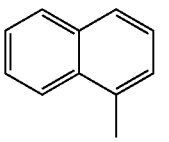 | 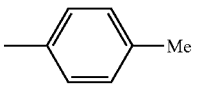 | 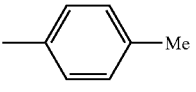 |
| 56 | 2 | Me | Direct bond | 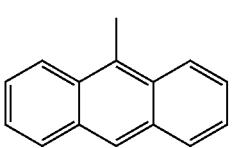 | 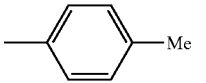 | 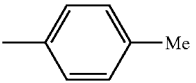 |

TABLE 4
| | n | R1, R2 | X1 | X2 | Y1 | Y2 |
|---|---|---|---|---|---|---|
| 57 | 2 | Me | Direct bond | 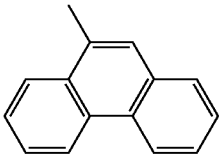 | 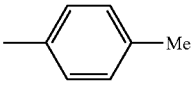 |  |
| 58 | 2 | Me | Direct bond | 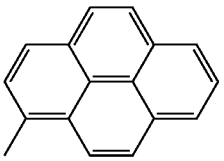 | 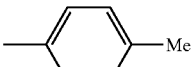 | 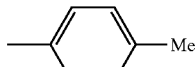 |
| 59 | 2 | Me | 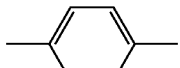 | H | Ph | Ph |
| 60 | 2 | Me |  | H | 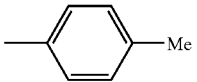 | 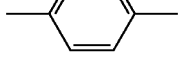 |
| 61 | 2 | Me | 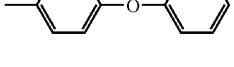 | H | 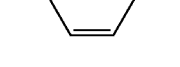 | 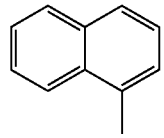 |
| 62 | 2 | Me | 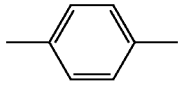 | H | Ph | 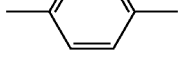 |
| 63 | 2 | Me | 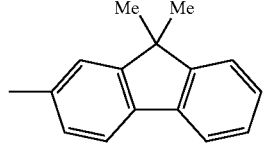 | H | Ph |  |
| 64 | 2 | Me | 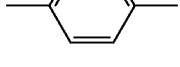 | H | Ph | 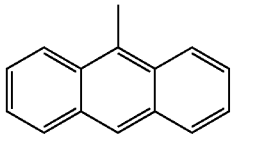 |
| 65 | 2 | Me | 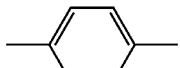 | H | Ph |  |
| 66 | 2 | Me |  | H | Ph |  |
| 67 | 2 | Me |  | H | Ph |  |

TABLE 4-continued
| | n | R1, R2 | X1 | X2 | Y1 | Y2 |
|---|---|---|---|---|---|---|
| 68 | 2 | Me |  | H | Ph | 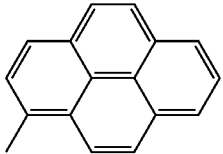 |
| 69 | 2 | Me | 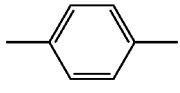 | Ph | Ph | Ph |
| 70 | 2 | Me | 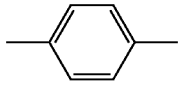 | Ph | 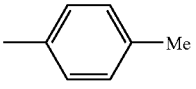 | 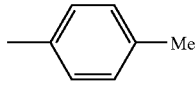 |
| 71 | 2 | Me | 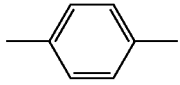 | Ph | Ph | 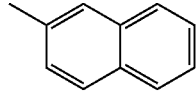 |
| 72 | 2 | Me | 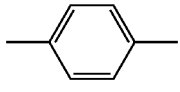 | Ph | Ph | 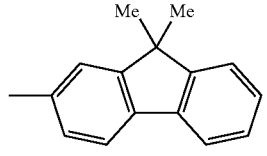 |
| 73 | 2 | Me | 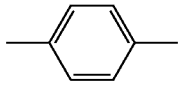 | Ph | Ph | 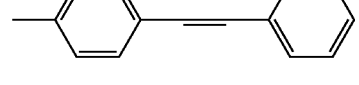 |
| 74 | 2 | Me | 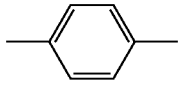 | 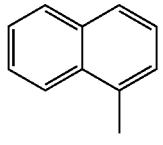 | 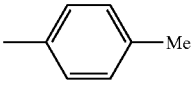 | 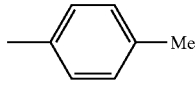 |
| 75 | 2 | Me |  | 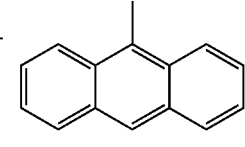 | 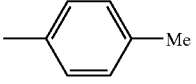 | 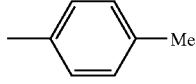 |
| 76 | 2 | Me | 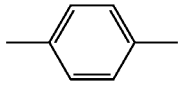 | 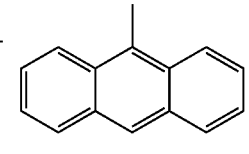 | Ph | 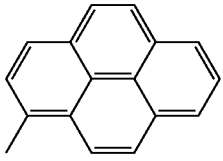 |
TABLE 5
| | n | R1, R2 | X1 | X2 | Y1 | Y2 |
|---|---|---|---|---|---|---|
| 77 | 2 | Me | 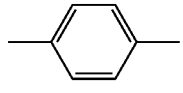 | 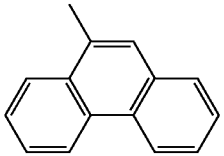 | 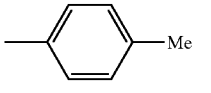 | 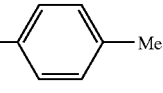 |

TABLE 5-continued

| | n | R1, R2 | X1 | X2 | Y1 | Y2 |
|---|---|---|---|---|---|---|
| 78 | 2 | Me | ⟨phenylene⟩ | ⟨pyrene⟩ | ⟨C6H4-Me⟩ | ⟨C6H4-Me⟩ |
| 79 | 2 | Me | ⟨phenylene⟩ | ⟨pyrene⟩ | Ph | ⟨pyrene⟩ |
| 80 | 2 | Me | ⟨trimethylphenylene⟩ | H | ⟨C6H4-Me⟩ | ⟨C6H4-Me⟩ |
| 81 | 2 | Me | ⟨tetrafluorophenylene⟩ | H | ⟨C6H4-Me⟩ | ⟨C6H4-Me⟩ |
| 82 | 2 | Me | ⟨tetrafluorophenylene⟩ | ⟨methylanthracene⟩ | ⟨C6H4-Me⟩ | ⟨C6H4-Me⟩ |
| 83 | 2 | Me | ⟨diphenyl ether⟩ | H | ⟨C6H4-Me⟩ | ⟨C6H4-Me⟩ |
| 84 | 2 | Me | ⟨naphthalene⟩ | H | ⟨C6H4-Me⟩ | ⟨C6H4-Me⟩ |
| 85 | 2 | Me | ⟨9,10-dimethylanthracene⟩ | H | ⟨C6H4-Me⟩ | ⟨C6H4-Me⟩ |
| 86 | 2 | Me | ⟨9,10-dimethylanthracene⟩ | ⟨methylanthracene⟩ | ⟨C6H4-Me⟩ | ⟨C6H4-Me⟩ |

TABLE 5-continued
| n | R1, R2 | X1 | X2 | Y1 | Y2 |
|---|---|---|---|---|---|
| 87 | 2 | Me | 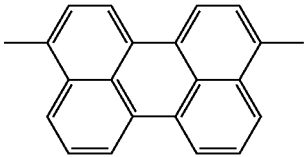 | H | 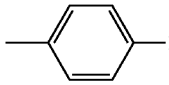 | 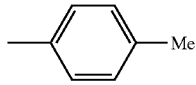 |
| 88 | 2 | Me | 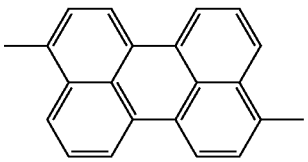 | H | 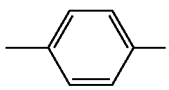 | 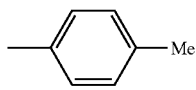 |
| 89 | 2 | n-Bu | 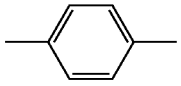 | H | 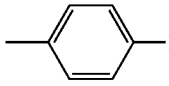 |  |
| 90 | 2 | n-Bu | 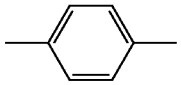 | 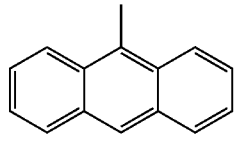 | 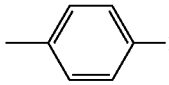 | 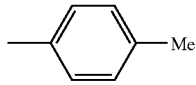 |
| 91 | 3 | Me | Direct bond | H | Ph | Ph |
| 92 | 3 | Me | Direct bond | H | 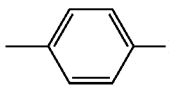 | 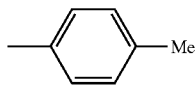 |
| 93 | 3 | Me | Direct bond | H | Ph | 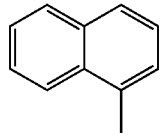 |
| 94 | 3 | Me | Direct bond | H | Ph | 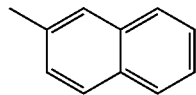 |
TABLE 6
| n | R1, R2 | X1 | X2 | Y1 | Y2 |
|---|---|---|---|---|---|
| 95 | 3 | Me | Direct bond | H | Ph | 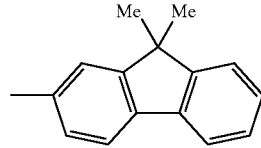 |
| 96 | 3 | Me | Direct bond | H | Ph | 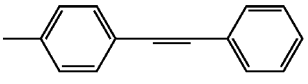 |
| 97 | 3 | Me | Direct bond | H | Ph | 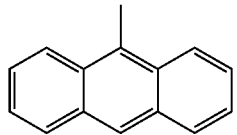 |

TABLE 6-continued
| | n | R1, R2 | X1 | X2 | Y1 | Y2 |
|---|---|---|---|---|---|---|
| 98 | 3 | Me | Direct bond | H | Ph | 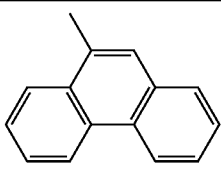 |
| 99 | 3 | Me | Direct bond | H | Ph | 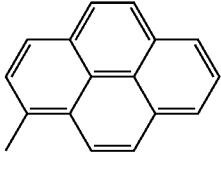 |
| 100 | 3 | Me | Direct bond | H | 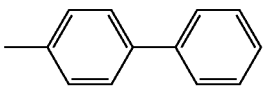 | 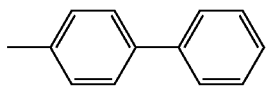 |
| 101 | 3 | Me | Direct bond | H | 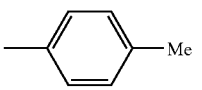 | 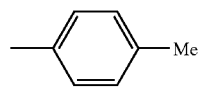 |
| 102 | 3 | Me | Direct bond | Ph | Ph | 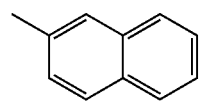 |
| 103 | 3 | Me | Direct bond | Ph | Ph | 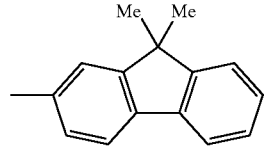 |
| 104 | 3 | Me | Direct bond | Ph | Ph | 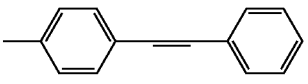 |
| 105 | 3 | Me | Direct bond | 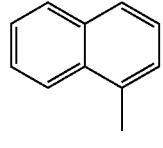 | 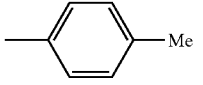 | 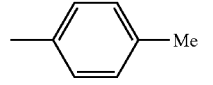 |
| 106 | 3 | Me | Direct bond | 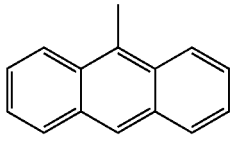 | 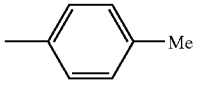 | 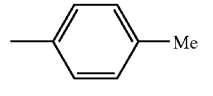 |
| 107 | 3 | Me | Direct bond | 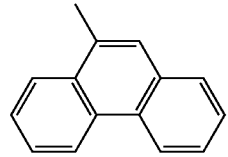 | 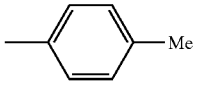 | 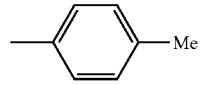 |
| 108 | 3 | Me | Direct bond | 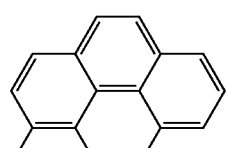 | 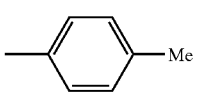 | 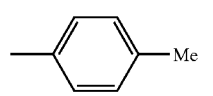 |

TABLE 6-continued

| | n | R1, R2 | X1 | X2 | Y1 | Y2 |
|---|---|---|---|---|---|---|
| 109 | 3 | Me | 1,4-phenylene | H | 4-methylphenyl | 4-methylphenyl |
| 110 | 3 | Me | 1,4-phenylene | H | Ph | 2-naphthyl |
| 111 | 3 | Me | 1,4-phenylene | H | Ph | 9,9-dimethylfluoren-2-yl |
| 112 | 3 | Me | 1,4-phenylene | H | Ph | 4-(phenylethynyl)phenyl |
| 113 | 3 | Me | 1,4-phenylene | H | Ph | anthracen-9-yl |
| 114 | 3 | Me | 1,4-phenylene | H | Ph | pyren-1-yl |

TABLE 7

| | n | R1, R2 | X1 | X2 | Y1 | Y2 |
|---|---|---|---|---|---|---|
| 115 | 3 | Me | 1,4-phenylene | Ph | 4-methylphenyl | 4-methylphenyl |
| 116 | 3 | Me | 1,4-phenylene | naphthalen-1-yl | 4-methylphenyl | 4-methylphenyl |
| 117 | 3 | Me | 1,4-phenylene | anthracen-9-yl | 4-methylphenyl | 4-methylphenyl |
| 118 | 3 | Me | 1,4-phenylene | anthracen-9-yl | Ph | pyren-1-yl |

TABLE 7-continued

| | n | R1, R2 | X1 | X2 | Y1 | Y2 |
|---|---|---|---|---|---|---|
| 119 | 3 | Me | -C6H4- (para) | methylpyrene | -C6H4-Me | -C6H4-Me |
| 120 | 3 | Me | -C6H4- (para) | methylpyrene | Ph | methylpyrene |
| 121 | 3 | Me | trimethylphenyl | H | -C6H4-Me | -C6H4-Me |
| 122 | 3 | Me | tetrafluorophenyl | H | -C6H4-Me | -C6H4-Me |
| 123 | 3 | Me | tetrafluorophenyl | methylanthracene | -C6H4-Me | -C6H4-Me |
| 124 | 3 | Me | -C6H4-S-C6H4- | H | -C6H4-Me | -C6H4-Me |
| 125 | 3 | Me | 1,4-naphthyl | H | -C6H4-Me | -C6H4-Me |
| 126 | 3 | Me | dimethylanthracene (9,10) | H | -C6H4-Me | -C6H4-Me |
| 127 | 3 | Me | dimethylanthracene (9,10) | methylanthracene | -C6H4-Me | -C6H4-Me |

TABLE 7-continued
| n | R1, R2 | X1 | X2 | Y1 | Y2 |
|---|---|---|---|---|---|
| 128 | 3 | Me | 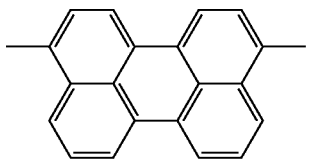 | H | 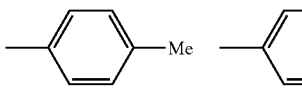 | 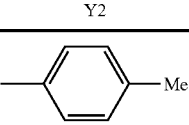 |
| 129 | 3 | Me | 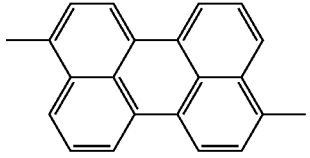 | H | 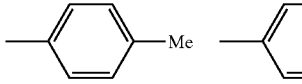 | 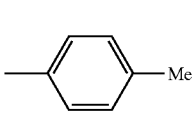 |
| 130 | 3 | n-Bu | 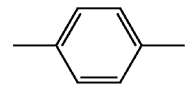 | H | 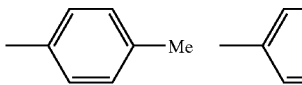 | 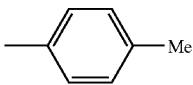 |
| 131 | 3 | n-Bu | 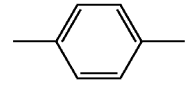 | 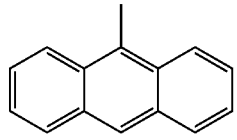 | 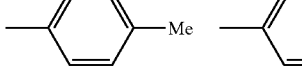 | 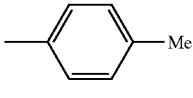 |
TABLE 8
| n | R1, R2 | X1 | X2 | Y1 | Y2 |
|---|---|---|---|---|---|
| 132 | 3 | Me | Direct bond | H | Ph | Ph |
| 133 | 3 | Me | Direct bond | H | 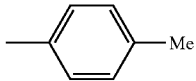 | 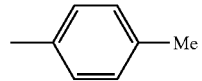 |
| 134 | 3 | Me | Direct bond | H | Ph | 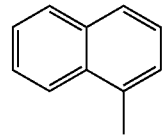 |
| 135 | 3 | Me | Direct bond | H | Ph | 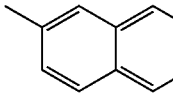 |
| 136 | 3 | Me | Direct bond | H | Ph | 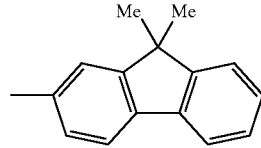 |
| 137 | 3 | Me | Direct bond | H | Ph |  |
| 138 | 3 | Me | Direct bond | H | Ph | 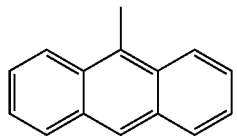 |

TABLE 8-continued
| | n | R1, R2 | X1 | X2 | Y1 | Y2 |
|---|---|---|---|---|---|---|
| 139 | 3 | Me | Direct bond | H | Ph | 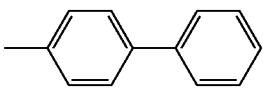 |
| 140 | 3 | Me | Direct bond | H | Ph | 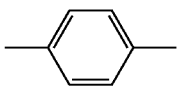 |
| 141 | 3 | Me | Direct bond | H | 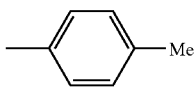 | 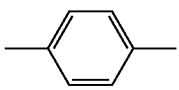 |
| 142 | 4 | Me |  | H | 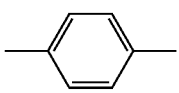 | 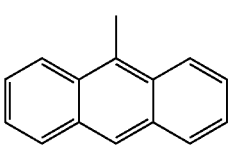 |
| 143 | 4 | Me | 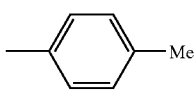 | H | Ph |  |
| 144 | 4 | Me | 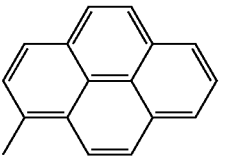 | H | Ph | 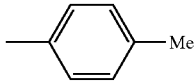 |
| 145 | 4 | Me |  | 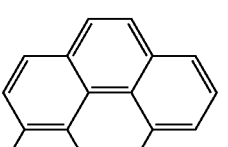 | 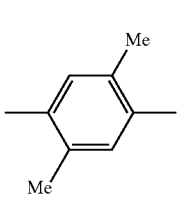 | 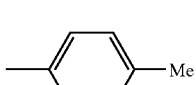 |
| 146 | 4 | Me |  |  |  |  |
| 147 | 4 | Me |  |  | Ph |  |
| 148 | 4 | Me |  | H |  |  |

TABLE 8-continued
| n | R1, R2 | X1 | X2 | Y1 | Y2 |
|---|---|---|---|---|---|
| 149 | 4 | Me | (tetrafluorophenyl) | H | —C₆H₄—Me (p) | —C₆H₄—Me (p) |
| 150 | 4 | Me | (1,4-naphthylene) | H | —C₆H₄—Me (p) | —C₆H₄—Me (p) |
TABLE 9
| n | R1, R2 | X1 | X2 | Y1 | Y2 |
|---|---|---|---|---|---|
| 151 | 4 | Me | (9,10-dimethylanthracene-diyl) | H | —C₆H₄—Me (p) | —C₆H₄—Me (p) |
| 152 | 4 | Me | (dimethylperylene-diyl) | H | —C₆H₄—Me (p) | —C₆H₄—Me (p) |
| 153 | 4 | Me | (dimethylperylene-diyl) | H | —C₆H₄—Me (p) | —C₆H₄—Me (p) |
| 154 | 4 | n-Bu | (p-phenylene) | H | —C₆H₄—Me (p) | —C₆H₄—Me (p) |
| 155 | 4 | n-Bu | (p-phenylene) | (9-methylanthracenyl) | —C₆H₄—Me (p) | —C₆H₄—Me (p) |
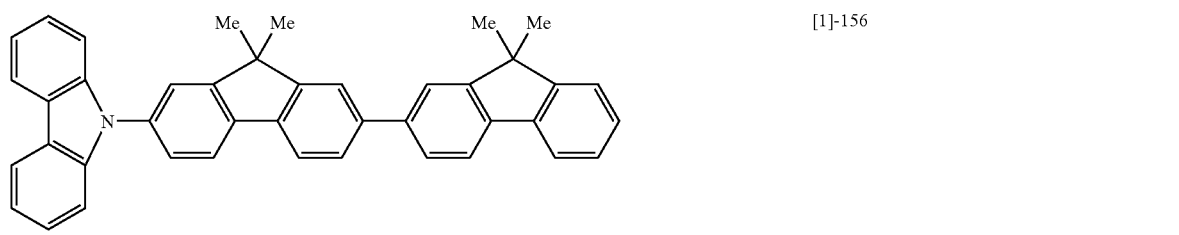
[1]-156

TABLE 9-continued
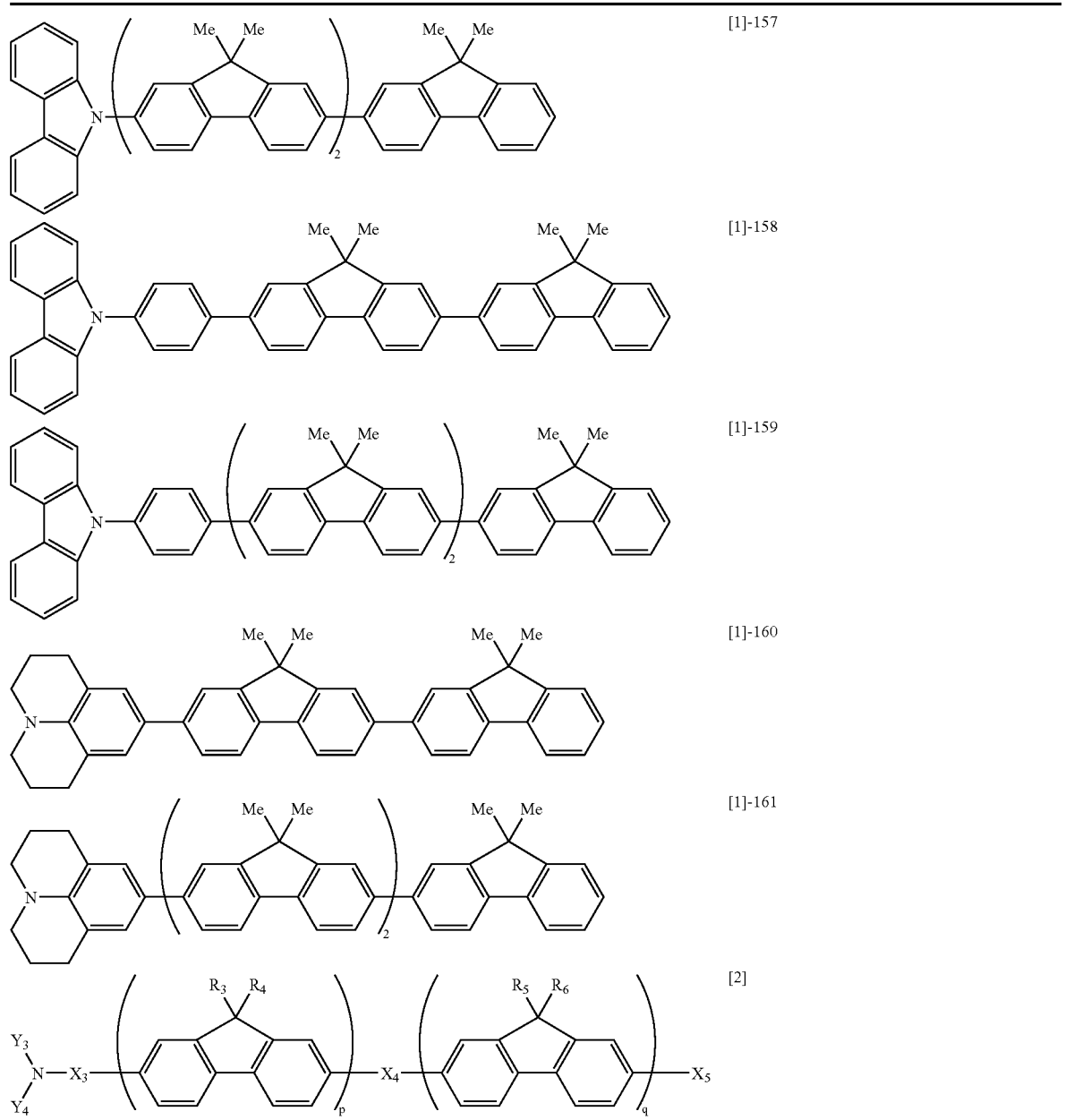
TABLE 10
| p, q | R3, R4 | R5, R6 | X3 | X4 | X5 | Y3 | Y4 |
|---|---|---|---|---|---|---|---|
| 1 | 1, 1 | Me | Me | Single bond | ⌬(p-phenylene) | H | Me | Ph |
| 2 | 1, 1 | Me | Me | Single bond | ⌬(p-phenylene) | H | Ph | Ph |
| 3 | 1, 1 | Me | Me | Single bond | ⌬(p-phenylene) | H | ⌬-Me (p-tolyl) | ⌬-Me (p-tolyl) |

TABLE 10-continued
| | p, q | R3, R4 | R5, R6 | X3 | X4 | X5 | Y3 | Y4 |
|---|---|---|---|---|---|---|---|---|
| 4 | 1, 1 | Me | n-Bu | Single bond | 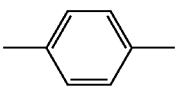 | H | 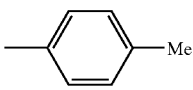 | 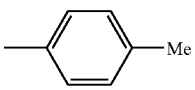 |
| 5 | 1, 1 | n-Bu | n-Bu | Single bond |  | H | 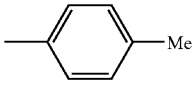 | 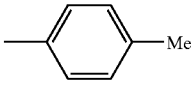 |
| 6 | 1, 1 | Me | Me | Single bond |  | H | 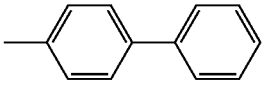 | 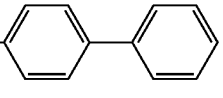 |
| 7 | 1, 1 | Me | Me | Single bond | 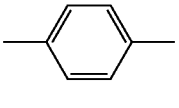 | H | 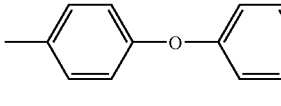 | 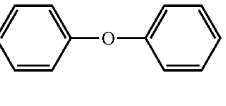 |
| 8 | 1, 1 | Me | Me | Single bond | 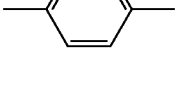 | H | Ph | 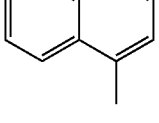 |
| 9 | 1, 1 | Me | Me | Single bond | 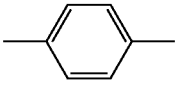 | H | Ph | 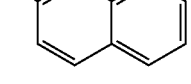 |
| 10 | 1, 1 | Me | Me | Single bond | 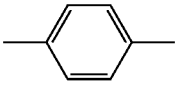 | H | Ph | 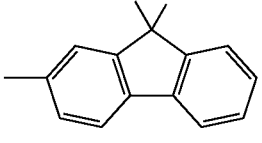 |
| 11 | 1, 1 | Me | Me | Single bond | 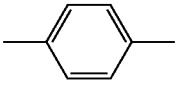 | H | Ph | 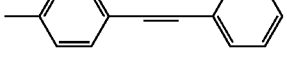 |
| 12 | 1, 1 | Me | Me | Single bond | 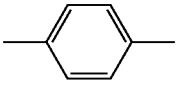 | H | Ph | 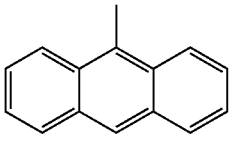 |
| 13 | 1, 1 | Me | Me | Single bond | 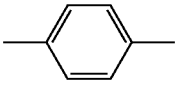 | H | Ph | 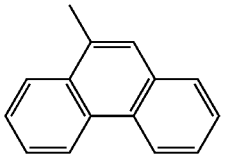 |
| 14 | 1, 1 | Me | Me | Single bond |  | H | Ph | 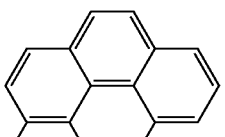 |

TABLE 10-continued
| | p, q | R3, R4 | R5, R6 | X3 | X4 | X5 | Y3 | Y4 |
|---|---|---|---|---|---|---|---|---|
| 15 | 1, 1 | Me | Me | Single bond | 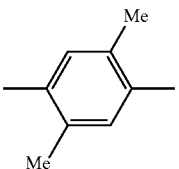 | H | 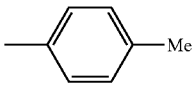 | 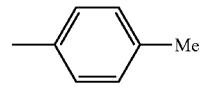 |
| 16 | 1, 1 | Me | Me | Single bond | 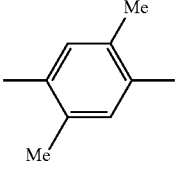 | H | Ph | 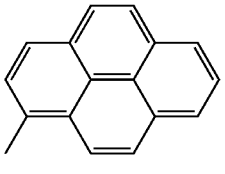 |
| 17 | 1, 1 | Me | Me | Single bond | 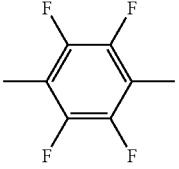 | H | 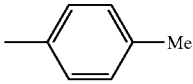 |  |
| 18 | 1, 1 | Me | Me | Single bond | 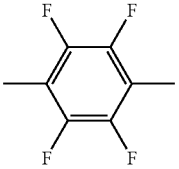 | H | Ph | 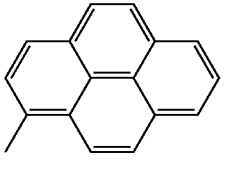 |
| 19 | 1, 1 | Me | Me | Single bond | 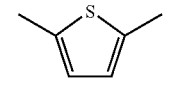 | H | 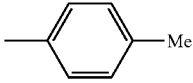 |  |
| 20 | 1, 1 | Me | Me | Single bond | 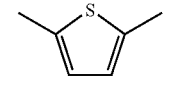 | H | Ph | 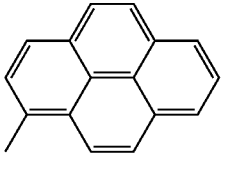 |
| 21 | 1, 1 | Me | Me | Single bond | 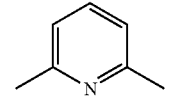 | H | 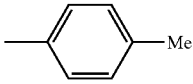 |  |
TABLE 11
| | p, q | R3, R4 | R5, R6 | X3 | X4 |
|---|---|---|---|---|---|
| 22 | 1, 1 | Me | Me | Single bond | 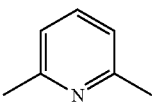 |
| 23 | 1, 1 | Me | Me | Single bond | 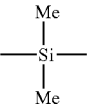 |

TABLE 11-continued
| 24 | 1, 1 | Me | Me | Single bond | 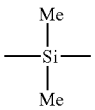 |
| 25 | 1, 1 | Me | Me | Single bond | 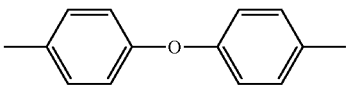 |
| 26 | 1, 1 | Me | Me | Single bond | 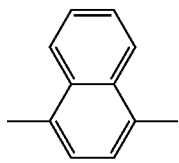 |
| 27 | 1, 1 | Me | Me | Single bond | 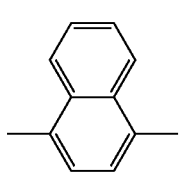 |
| 28 | 1, 1 | Me | Me | Single bond | 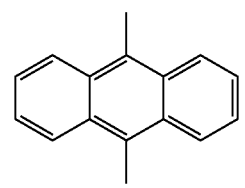 |
| 29 | 1, 1 | Me | Me | Single bond | 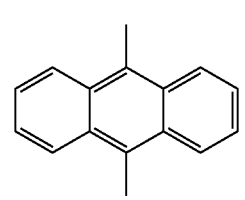 |
| 30 | 1, 1 | Me | Me | Single bond | 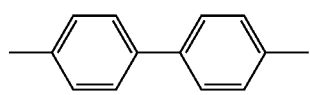 |
| 31 | 1, 1 | Me | Me | Single bond | 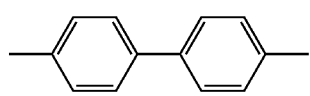 |
| 32 | 1, 1 | Me | Me | Single bond | 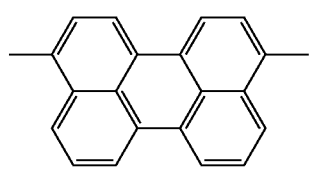 |
| 33 | 1, 1 | Me | Me | Single bond | 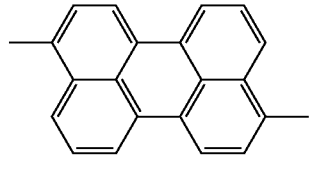 |
| 34 | 1, 2 | Me | Me | Single bond |  |

TABLE 11-continued
| | | | | | | |
|---|---|---|---|---|---|---|
| 35 | 1, 2 | Me | Me | Single bond |  | |
| 36 | 1, 2 | Me | Me | Single bond |  | |
| 37 | 1, 2 | Me | Me | Single bond |  | |
| 38 | 1, 2 | Me | Me | Single bond | 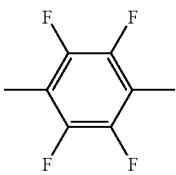 | |
| 39 | 1, 2 | Me | Me | Single bond | 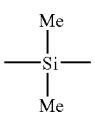 | |
| 40 | 1, 1 | Me | Me | 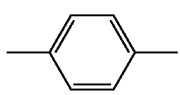 |  | |
| 41 | 1, 1 | Me | Me | 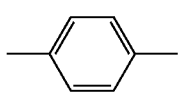 |  | |
| 42 | 1, 1 | Me | Me | 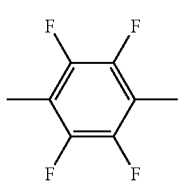 |  | |
| | X5 | Y3 | Y4 |
|---|---|---|---|
| 22 | H | Ph | 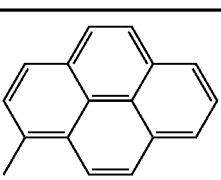 |
| 23 | H | 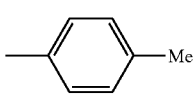 | 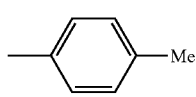 |
| 24 | H | Ph | 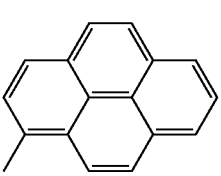 |
| 25 | H | 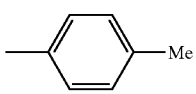 | 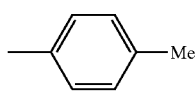 |

TABLE 11-continued
| 26 | H | 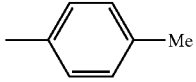 | 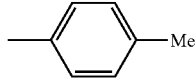 |
| 27 | H | Ph | 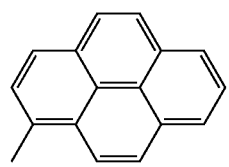 |
| 28 | H | 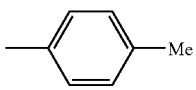 | 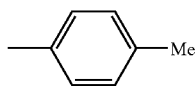 |
| 29 | H | Ph | 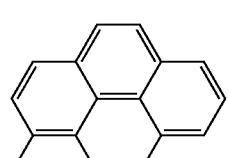 |
| 30 | H | 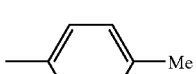 | 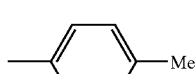 |
| 31 | H | Ph | 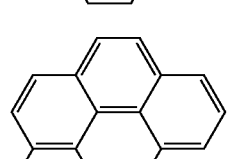 |
| 32 | H | 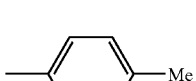 |  |
| 33 | H |  |  |
| 34 | H | 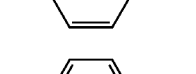 | 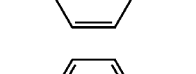 |
| 35 | H | Ph | 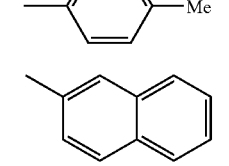 |
| 36 | H | Ph | 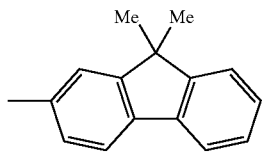 |
| 37 | H | Ph | 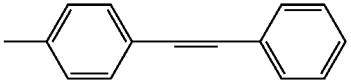 |
| 38 | H | 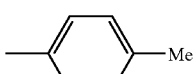 | 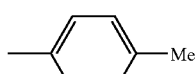 |

TABLE 11-continued
| | | X (left) | X (right) |
|---|---|---|---|
| 39 | H | 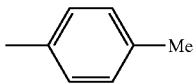 | 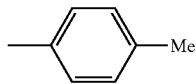 |
| 40 | H | 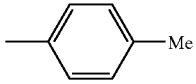 | 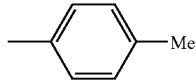 |
| 41 | H | 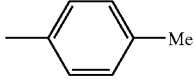 | 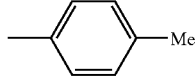 |
| 42 | H | 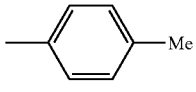 | 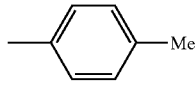 |
TABLE 12
| | p, q | R3, R4 | R5, R6 | X3 | X4 |
|---|---|---|---|---|---|
| 43 | 1, 1 | Me | Me | 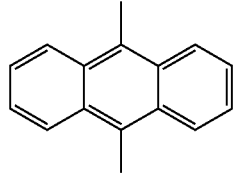 | 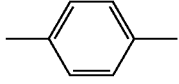 |
| 44 | 1, 1 | Me | n-Bu | 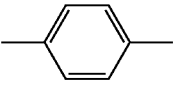 | 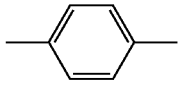 |
| 45 | 1, 1 | n-Bu | n-Bu | 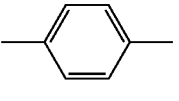 | 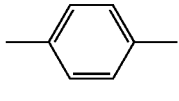 |
| 46 | 1, 1 | Me | Me | 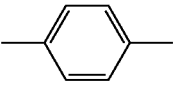 | 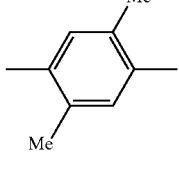 |
| 47 | 1, 1 | Me | Me | 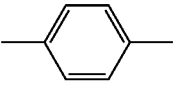 | 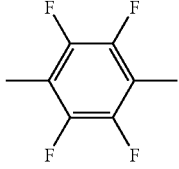 |
| 48 | 1, 1 | Me | Me | 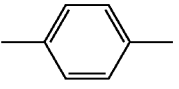 | 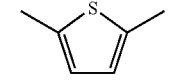 |
| 49 | 1, 1 | Me | Me | 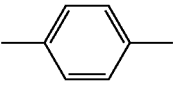 | 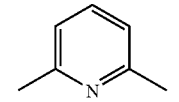 |
| 50 | 1, 1 | Me | Me |  | 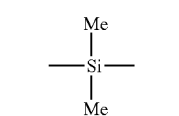 |

TABLE 12-continued
| | | | | | |
|---|---|---|---|---|---|
| 51 | 1, 1 | Me | Me | 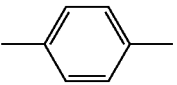 | 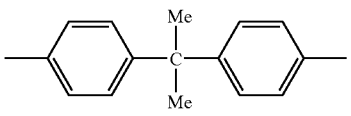 |
| 52 | 1, 1 | Me | Me |  | 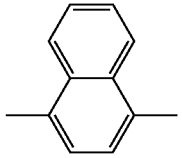 |
| 53 | 1, 1 | Me | Me | 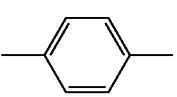 | 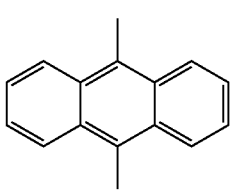 |
| 54 | 1, 1 | Me | Me | 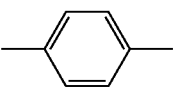 | 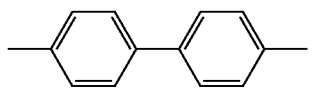 |
| 55 | 1, 1 | Me | Me | 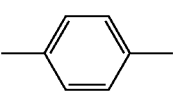 | 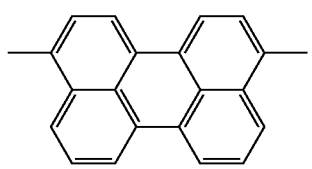 |
| 56 | 1, 1 | Me | Me | 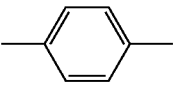 | 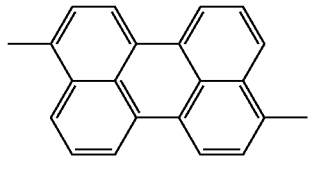 |
| 57 | 1, 2 | Me | Me | 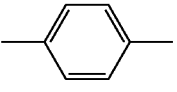 | 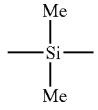 |
| 58 | 1, 2 | Me | Me | 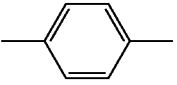 | 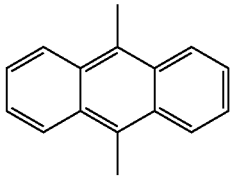 |
| 59 | 1, 1 | Me | Me | Single bond | 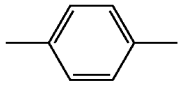 |
| 60 | 1, 1 | Me | Me | Single bond | 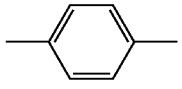 |
| 61 | 1, 1 | Me | Me | Single bond | 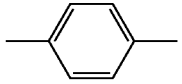 |

TABLE 12-continued
| 62 | 1, 1 | Me | Me | Single bond |  | |
|---|---|---|---|---|---|---|
| | | | | X5 | Y3 | Y4 |
| | 43 | | | H | 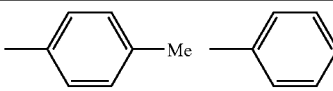 |  |
| | 44 | | | H | 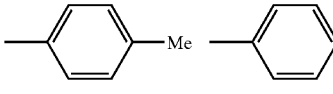 |  |
| | 45 | | | H | 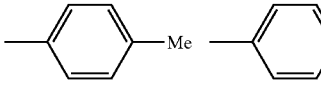 |  |
| | 46 | | | H | 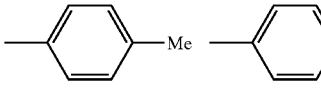 |  |
| | 47 | | | H | 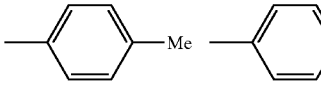 |  |
| | 48 | | | H | 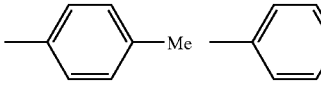 |  |
| | 49 | | | H | 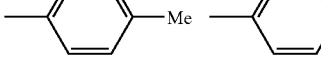 |  |
| | 50 | | | H | 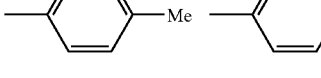 |  |
| | 51 | | | H | 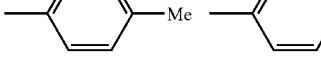 |  |
| | 52 | | | H | 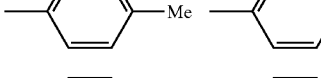 |  |
| | 53 | | | H | 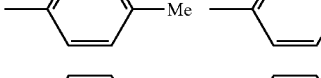 |  |
| | 54 | | | H | 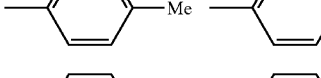 |  |
| | 55 | | | H | 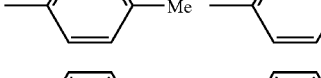 |  |
| | 56 | | | H | 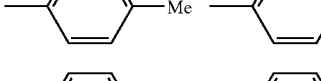 |  |
| | 57 | | | H | 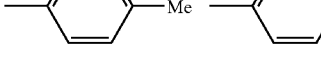 |  |

TABLE 12-continued
| | | | | |
|---|---|---|---|---|
| 58 | H | 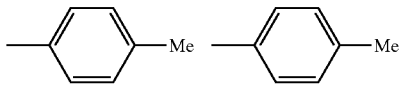 | 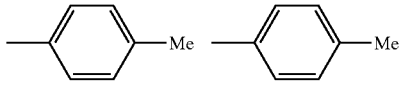 | |
| 59 | Ph | 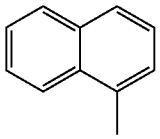 | 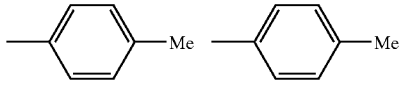 | |
| 60 | 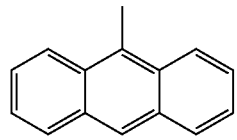 | 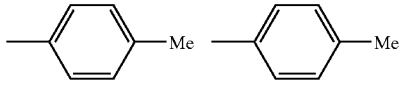 | 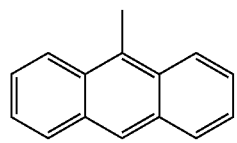 | |
| 61 | 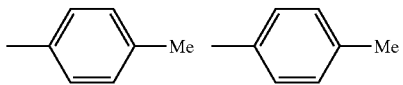 |  | 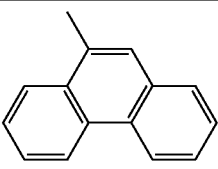 | |
| 62 | 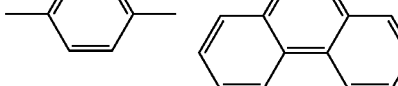 | 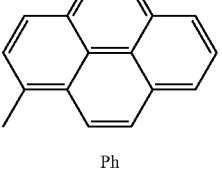 | 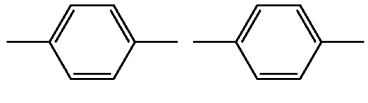 | |
TABLE 13
| | p, q | R3, R4 | R5, R6 | X3 | X4 | X5 |
|---|---|---|---|---|---|---|
| 63 | 1, 1 | Me | Me | Single bond | 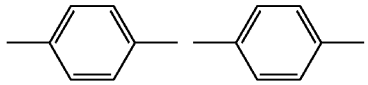 | 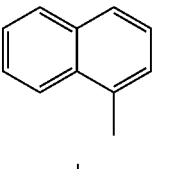 |
| 64 | 1, 1 | Me | Me | Single bond | 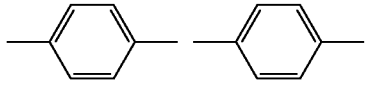 | 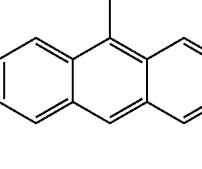 |
| 65 | 1, 1 | Me | Me |  |  | Ph |
| 66 | 1, 1 | Me | Me |  |  |  |
| 67 | 1, 1 | Me | Me |  |  |  |

TABLE 13-continued
| 68 | 1, 1 | Me | Me | 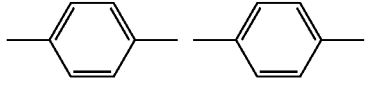 | 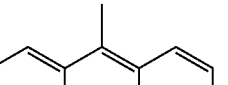 | 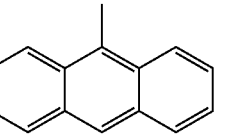 |
| 69 | 1, 1 | Me | Me | 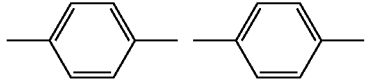 | 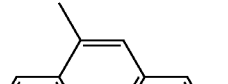 | 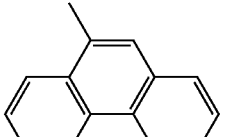 |
| 70 | 1, 1 | Me | Me | 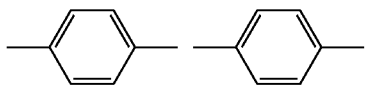 | 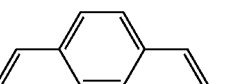 | 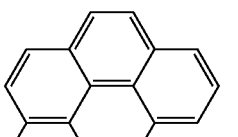 |
| 71 | 2, 2 | Me | Me | Single bond | 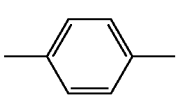 | H |
| 72 | 2, 2 | Me | Me | Single bond | 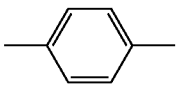 | H |
| 73 | 2, 2 | Me | Me | Single bond | 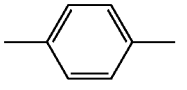 | H |
| 74 | 2, 2 | Me | n-Bu | Single bond | 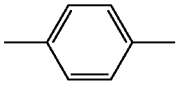 | H |
| 75 | 2, 2 | n-Bu | n-Bu | Single bond | 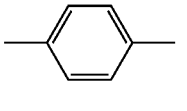 | H |
| 76 | 2, 2 | Me | Me | Single bond | 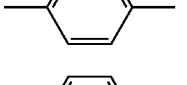 | H |
| 77 | 2, 2 | Me | Me | Single bond | 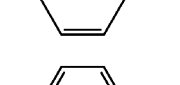 | H |
| 78 | 2, 2 | Me | Me | Single bond |  | H |
| 79 | 2, 2 | Me | Me | Single bond | 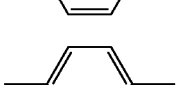 | H |
| 80 | 2, 2 | Me | Me | Single bond | 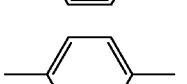 | H |
| 81 | 2, 2 | Me | Me | Single bond |  | H |

TABLE 13-continued
| | | | | | | |
|---|---|---|---|---|---|---|
| 82 | 2, 2 | Me | Me | Single bond | 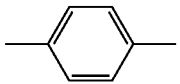 | H |
| 83 | 2, 2 | Me | Me | Single bond | 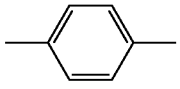 | H |
| 84 | 2, 2 | Me | Me | Single bond | 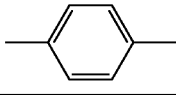 | H |
| | Y3 | Y4 |
|---|---|---|
| 63 | 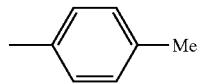 | 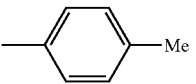 |
| 64 | 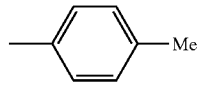 | 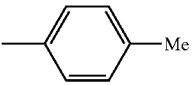 |
| 65 | 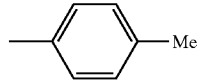 | 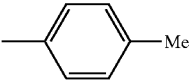 |
| 66 | 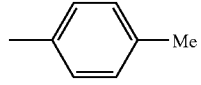 | 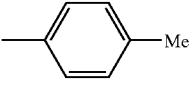 |
| 67 | 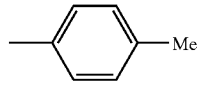 | 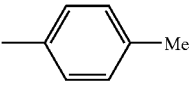 |
| 68 | 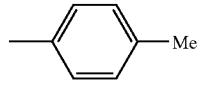 | 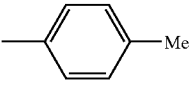 |
| 69 | 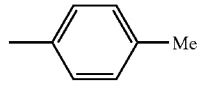 | 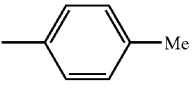 |
| 70 | 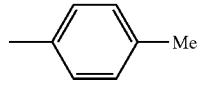 | 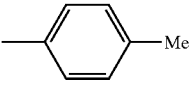 |
| 71 | Me | Ph |
| 72 | Ph | Ph |
| 73 | 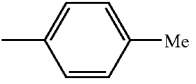 | 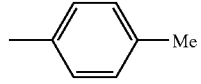 |
| 74 | 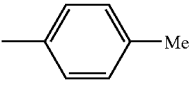 | 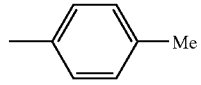 |
| 75 | 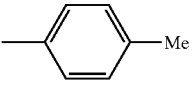 | 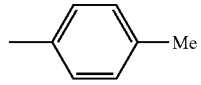 |
| 76 | 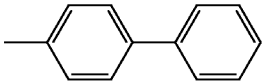 | 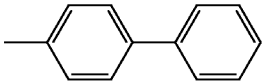 |

TABLE 13-continued

| 77 | 4-methylphenyl-O-phenyl | 4-methylphenyl-O-phenyl |
| 78 | Ph | 1-methylnaphthalene |
| 79 | Ph | 2-methylnaphthalene |
| 80 | Ph | 2-methyl-9,9-dimethylfluorene |
| 81 | Ph | 4-methyl-tolan (diphenylacetylene) |
| 82 | Ph | 9-methylanthracene |
| 83 | Ph | 9-methylphenanthrene |
| 84 | Ph | 1-methylpyrene |

[2]-85

[2]-86

TABLE 13-continued

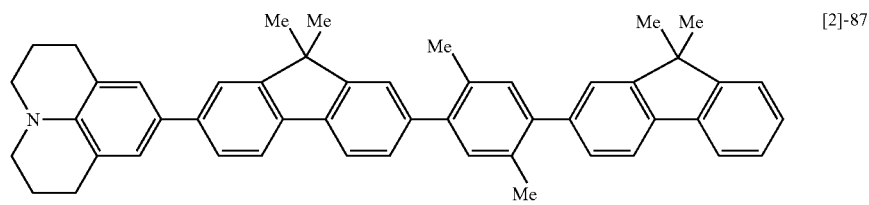
[2]-87

Next, the organic light-emitting device of the present invention will be described in detail.

The organic light-emitting device of the present invention is an organic light-emitting device comprising: a pair of electrodes which consist of an anode and a cathode, and one or more layers which are interposed between the electrodes and contain an organic compound, wherein at least one layer of the layers containing an organic compound contains at least one of the monoaminofluorene compounds represented by the above-mentioned general formula [1] or [2].

Moreover, it is preferable that the layer containing the compound represented by the above-mentioned general formula [1] or [2] contains at least one of the compounds represented by following general formulae [3] to [7], and it is more preferable that the layer containing the compound represented by the above-mentioned general formula [1] or [2] is a light-emitting layer.

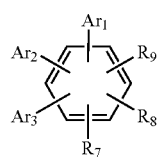
[3]

wherein $Ar_1$ to $Ar_3$ may be the same or different and are groups selected from the group consisting of substituted or unsubstituted aryl and heterocyclic ring groups, and either one of them may be a hydrogen atom, a substituted or unsubstituted alkyl group, or a substituted or unsubstituted aralkyl group; and $R_7$ to $R_9$ are groups selected from the group consisting of a hydrogen atom, a halogen group, substituted or unsubstituted alkyl and aralkyl groups, a substituted amino group and a cyano group.

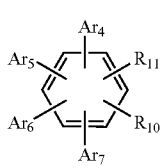
[4]

wherein $Ar_4$ to $Ar_7$ may be the same or different and are groups selected from the group consisting of substituted or unsubstituted aryl and heterocyclic ring groups; and $R_{10}$ and $R_{11}$ are groups selected from the group consisting of a hydrogen atom, a halogen group, substituted or unsubstituted alkyl and aralkyl groups, a substituted amino group and a cyano group.

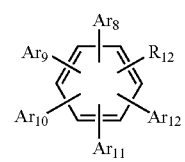
[5]

wherein $Ar_8$ to $Ar_{12}$ may be the same or different and are groups selected from the group consisting of substituted or unsubstituted aryl and heterocyclic ring groups; and $R_{12}$ is a group selected from the group consisting of a hydrogen atom, a halogen group, substituted or unsubstituted alkyl, aralkyl, aryl and heterocyclic ring groups, a substituted amino group and a cyano group.

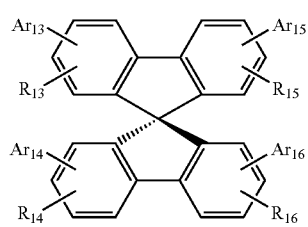
[6]

wherein $Ar_{13}$ to $Ar_{16}$ may be the same or different and are groups selected from the group consisting of substituted or unsubstituted aryl and heterocyclic ring groups, and up to any three of them may be a hydrogen atom, a halogen group, a substituted or unsubstituted alkyl group and a substituted or unsubstituted aralkyl group; and $R_{13}$ to $R_{16}$ are groups selected from the group consisting of a hydrogen atom, a halogen group, substituted or unsubstituted alkyl, aralkyl, aryl and heterocyclic ring groups, a substituted amino group and a cyano group.

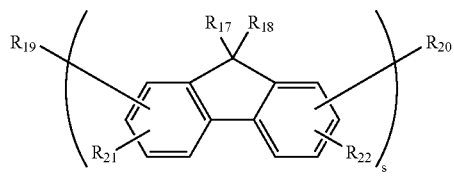

[7]

wherein $R_{17}$ and $R_{18}$ are groups selected from the group consisting of a hydrogen atom and substituted or unsubstituted alkyl, aralkyl and aryl groups, and $R_{17}$'s and $R_{18}$'s bound to different fluorene moieties may be the same or different and $R_{17}$ and $R_{18}$ bound to the same fluorene moiety may be the same or different; $R_{19}$ to $R_{22}$ are groups selected from the group consisting of a hydrogen atom, a halogen group, substituted or unsubstituted alkyl and aralkyl and alkoxy groups, a substituted silyl group and a cyano group; and s is an integer of 2 to 5.

Although the compounds represented by general formulae [3] to [7] can be used for the purpose of both the dopant material and host material in a light-emitting layer respectively to obtain a device with high color purity, high luminescence efficiency and longer operating life, a device holding high color purity luminescence and having even higher luminescence efficiency can be obtained with the combination of a compound represented by the general formula [1] or [2] as a dopant material with a suitable host material which easily causes energy transfer, for example, the compounds represented by general formulae [3] to [7]. The dopant concentration in the host material is preferably from 0.01% to 50% by weight, more preferably from 0.5% to 10% by weight.

Specific examples of the substituents in general formulae [3] to [7] are the same as those referred to in the above-mentioned general formulae [1] and [2]. Typical examples of the compound represented by general formulae [3] to [7] are given below but the present invention is not limited to these.

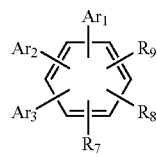

[3]

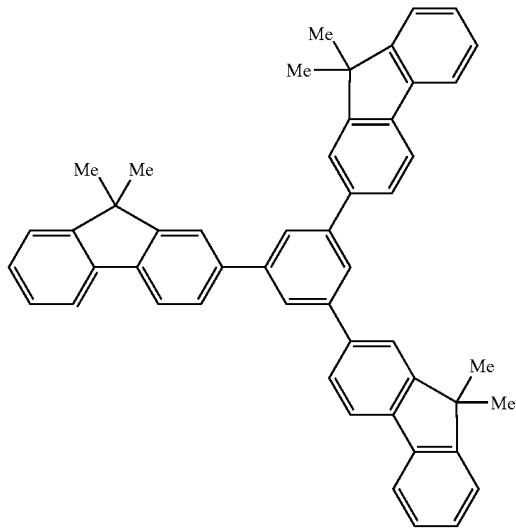

[3]-1

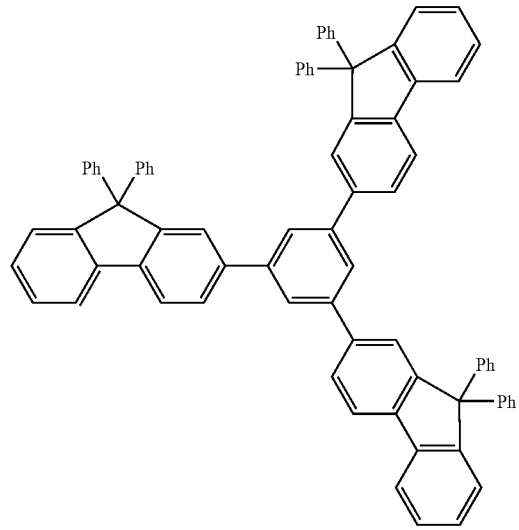

[3]-2

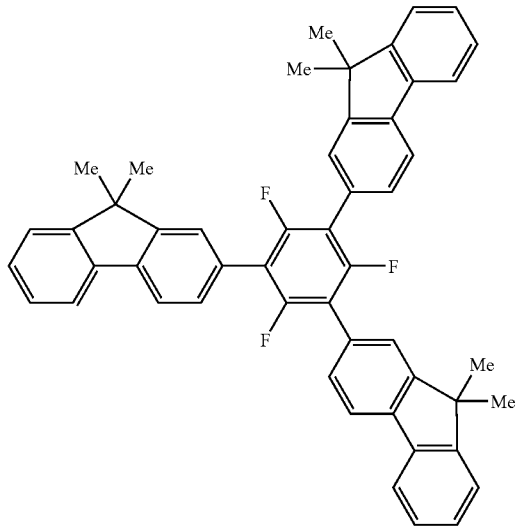

[3]-3

-continued
[3]-4
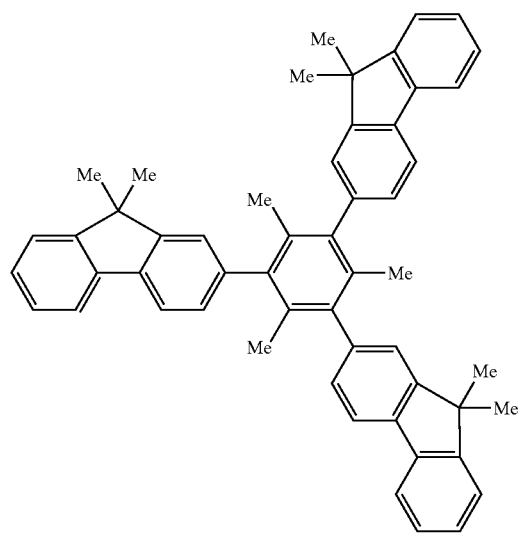
[3]-5
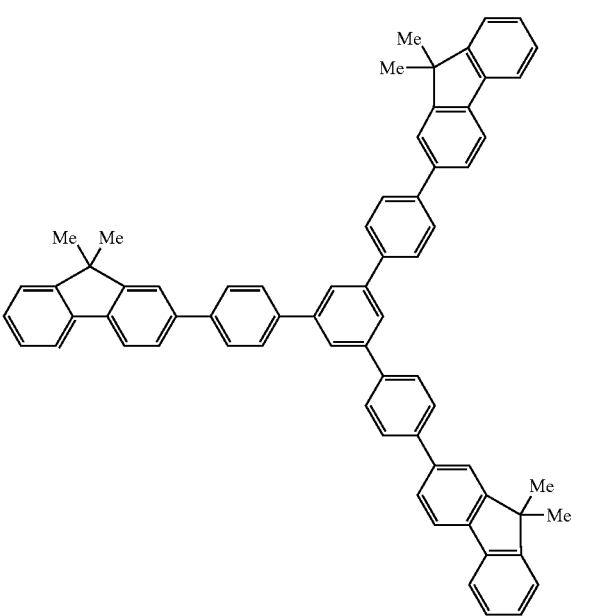
[3]-6
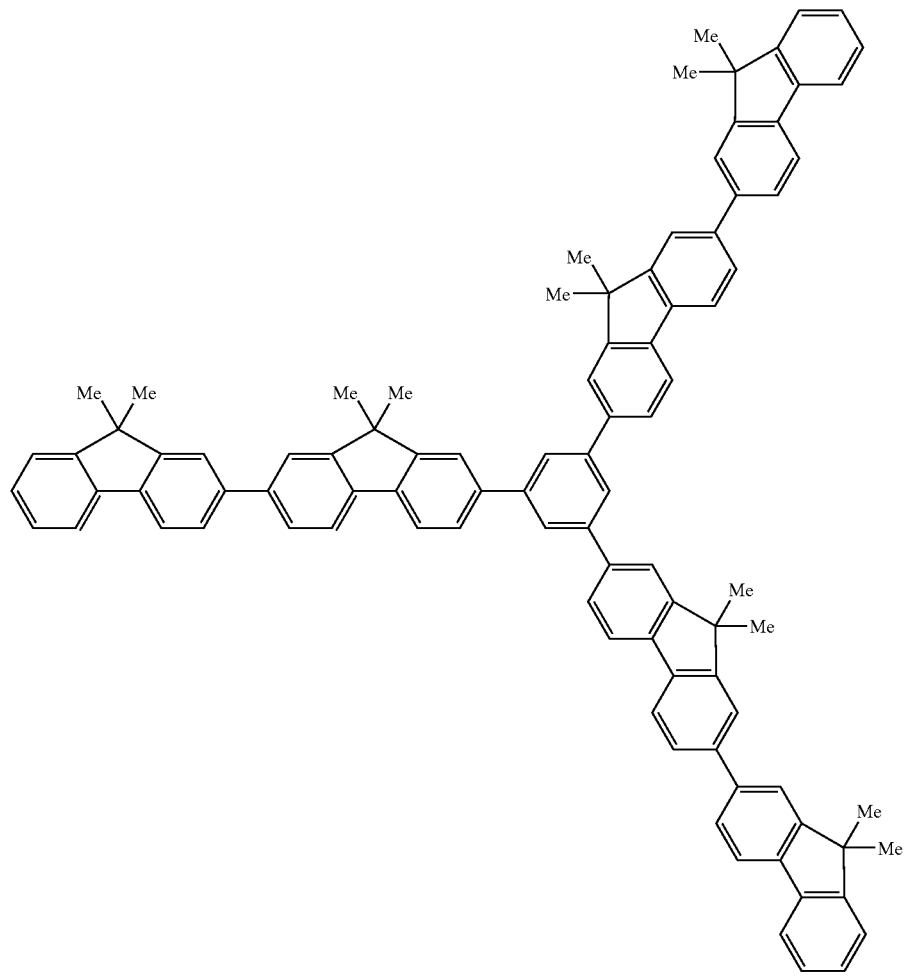

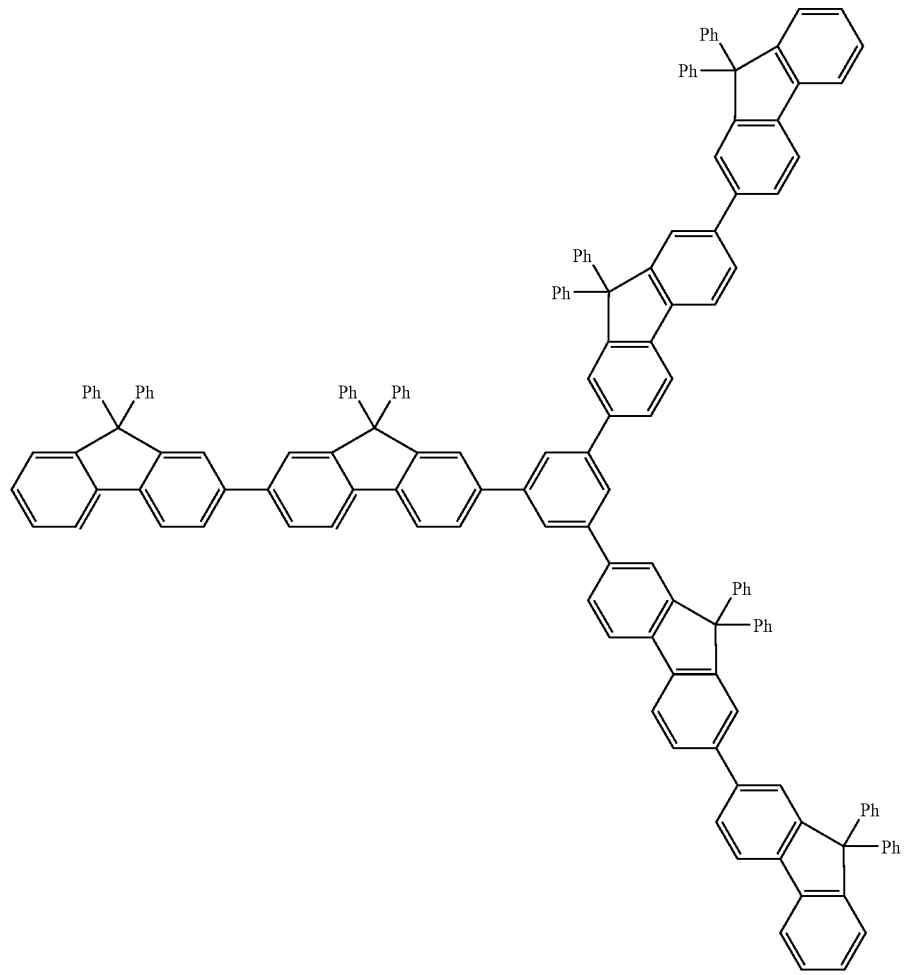
[3]-7
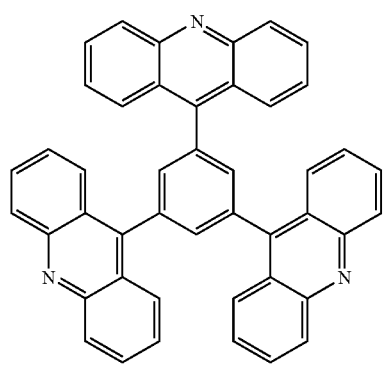
[3]-8
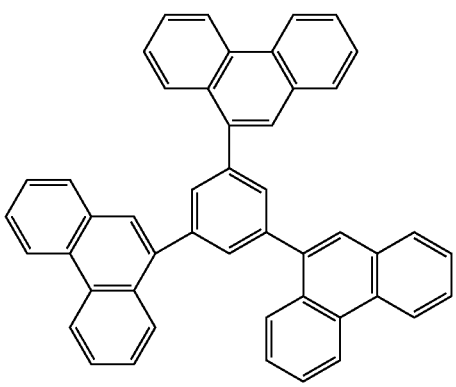
[3]-9

[3]-10
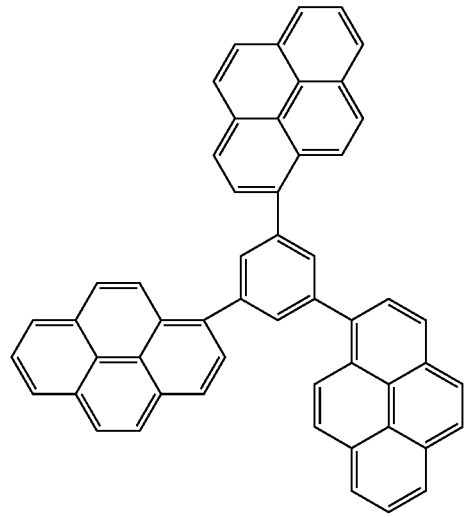
[3]-11
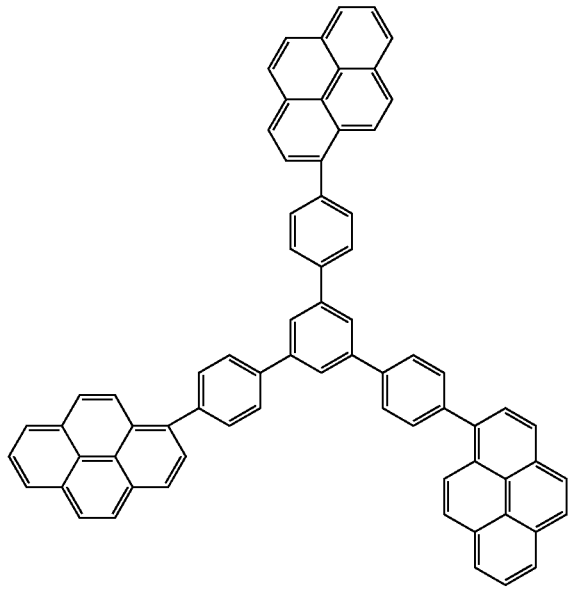
[3]-12
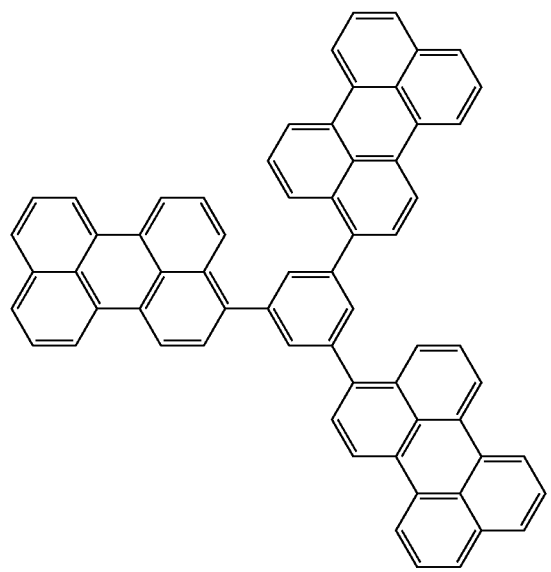
[3]-13
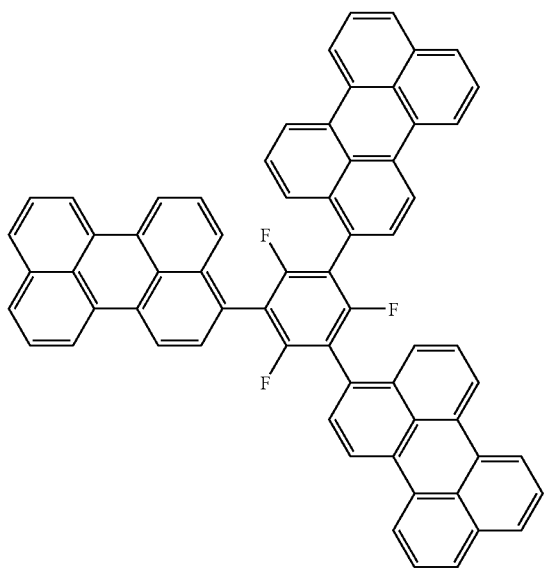

[3]-14
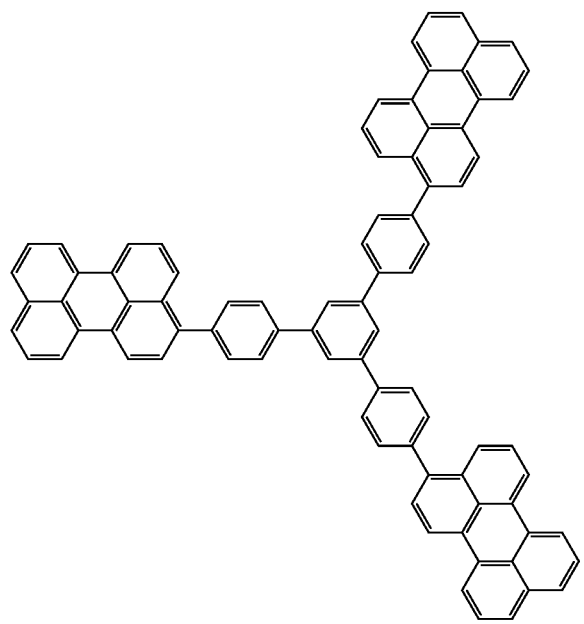
[3]-15
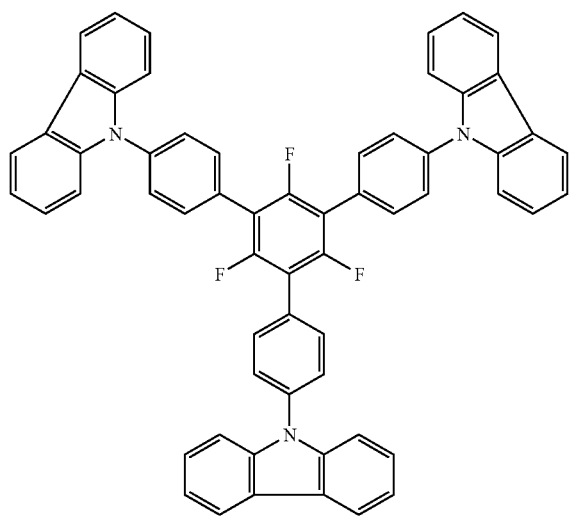
[4]
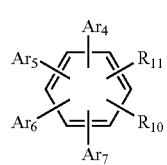
[4]-1
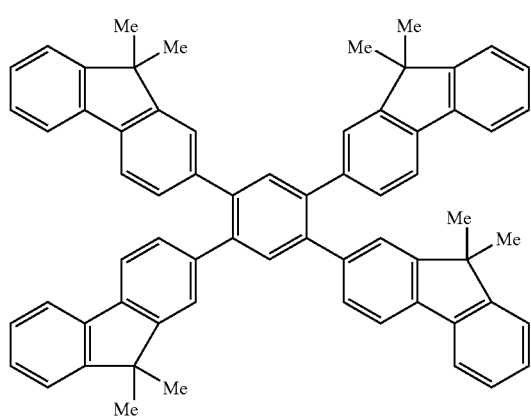
[4]-2
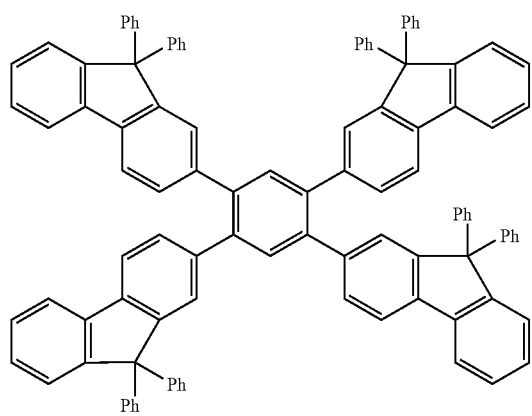
[4]-3
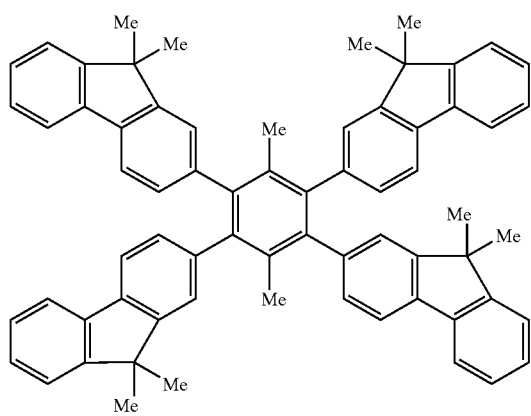

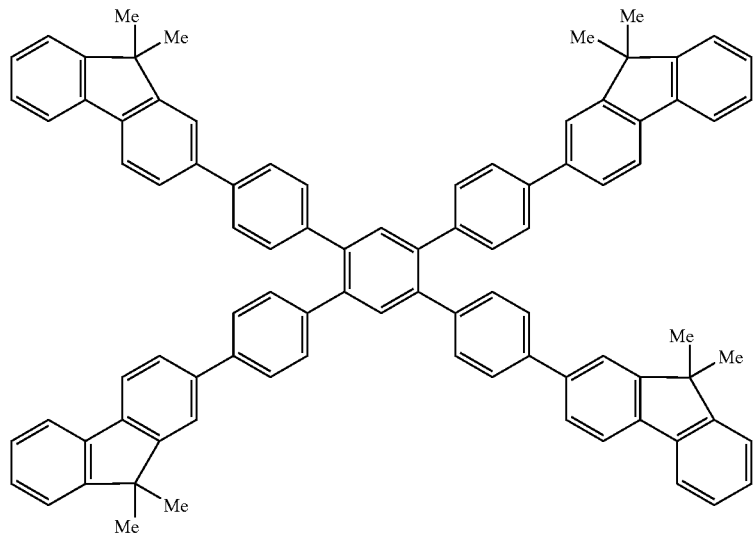
[4]-4
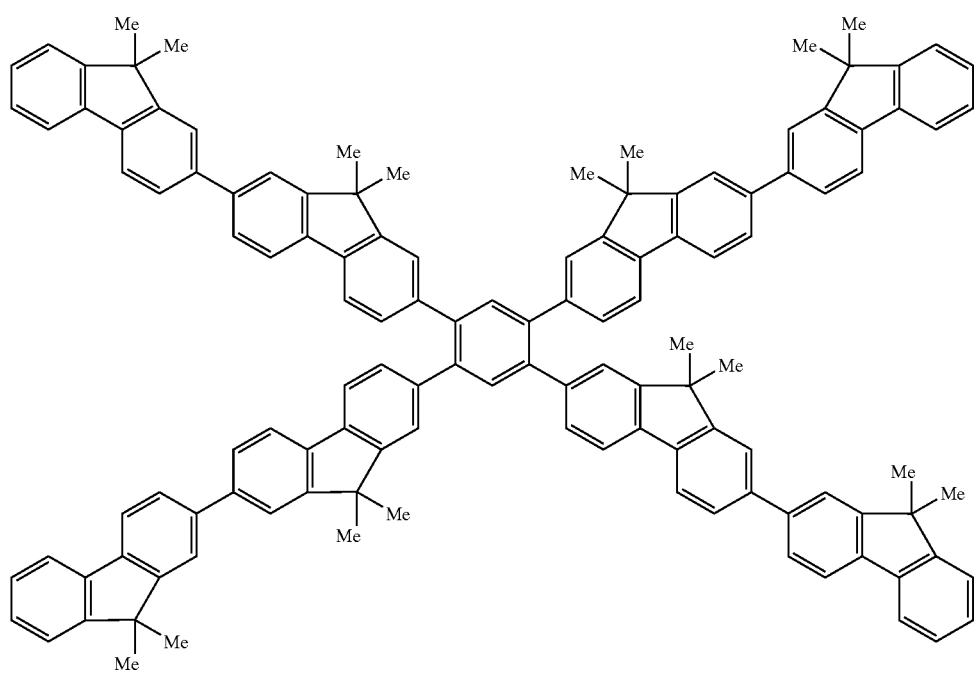
[4]-5

-continued
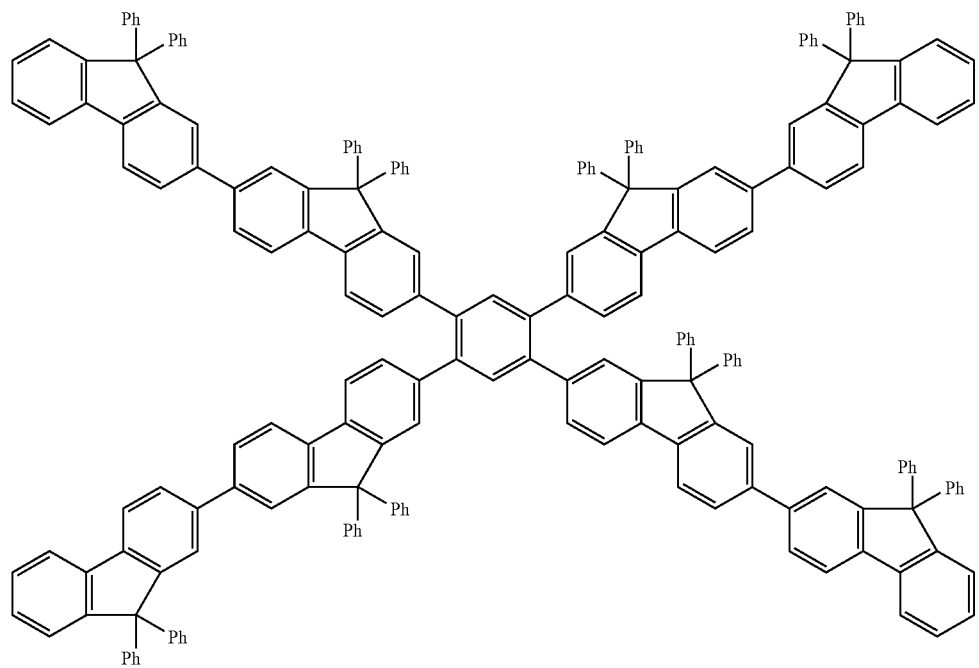
[4]-6
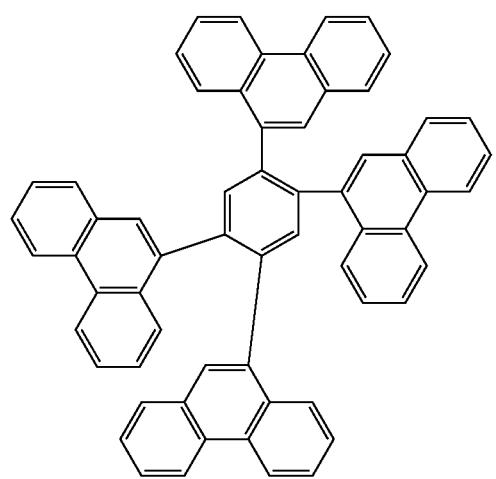
[4]-7
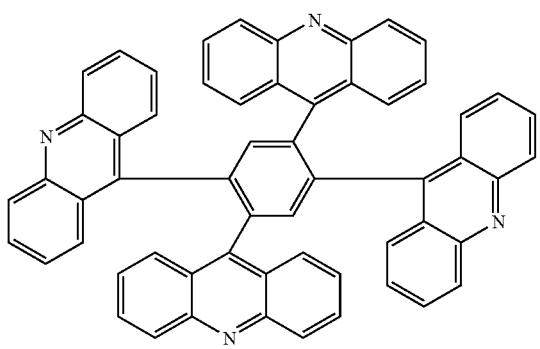
[4]-8

[4]-9
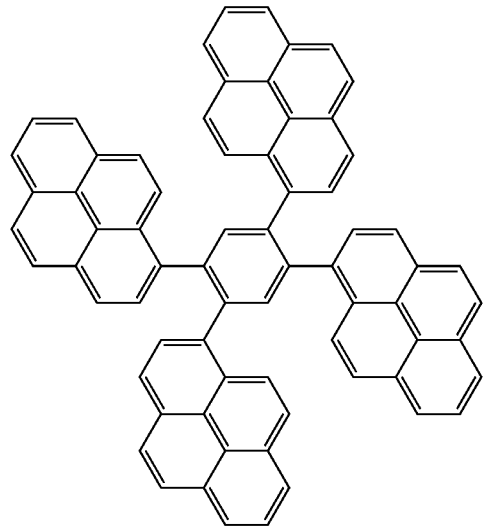
[4]-10
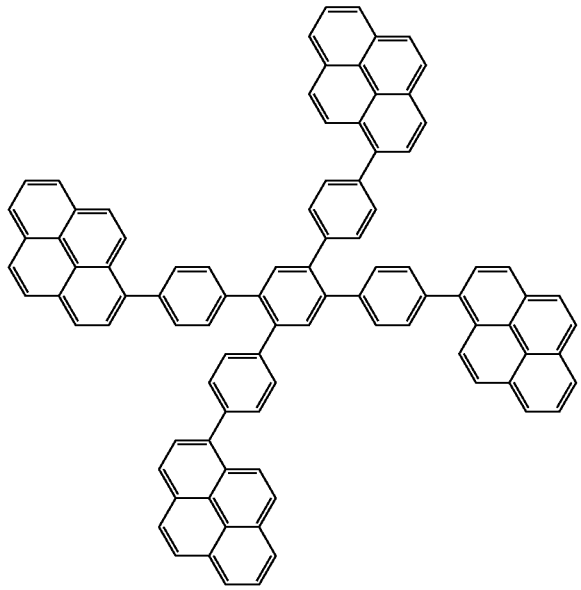
[4]-11
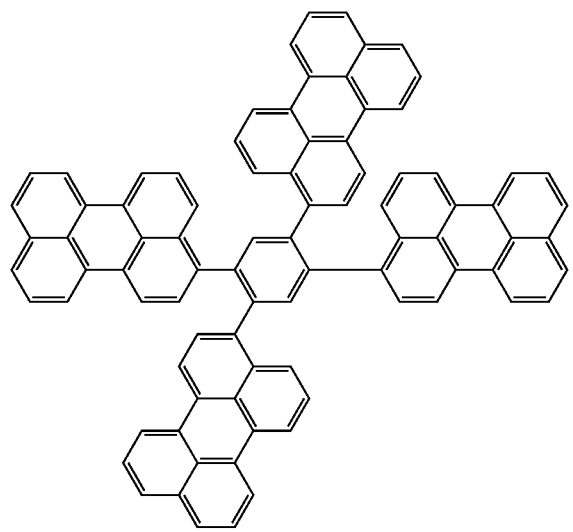
[4]-12
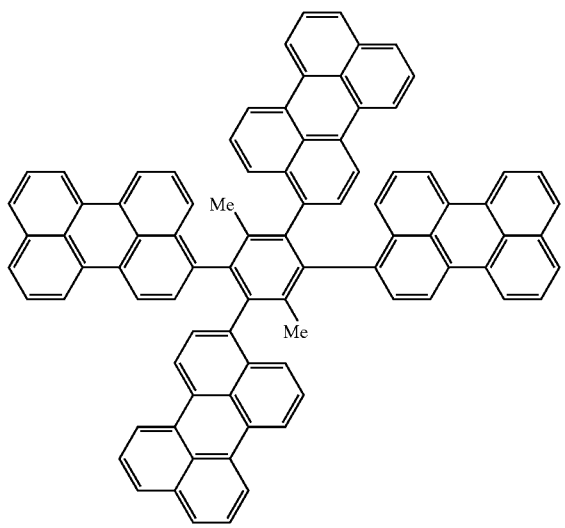

[4]-13
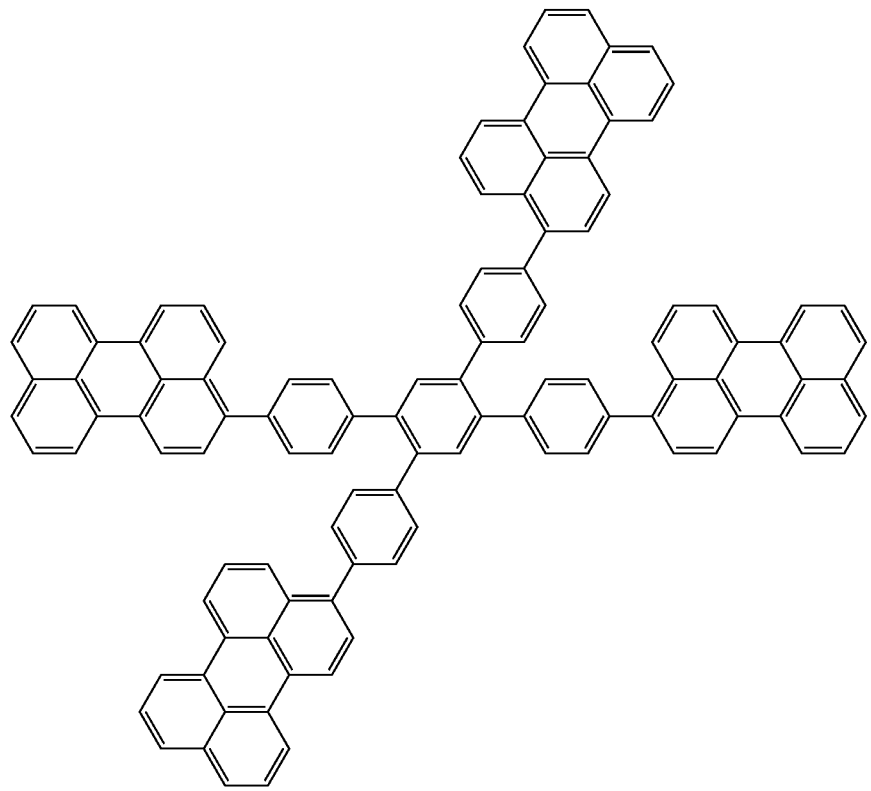
[4]-14
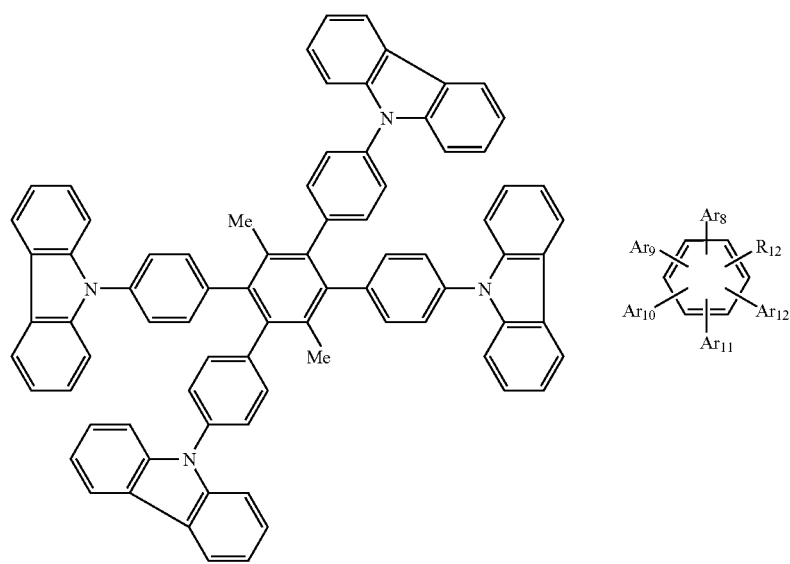
[5]

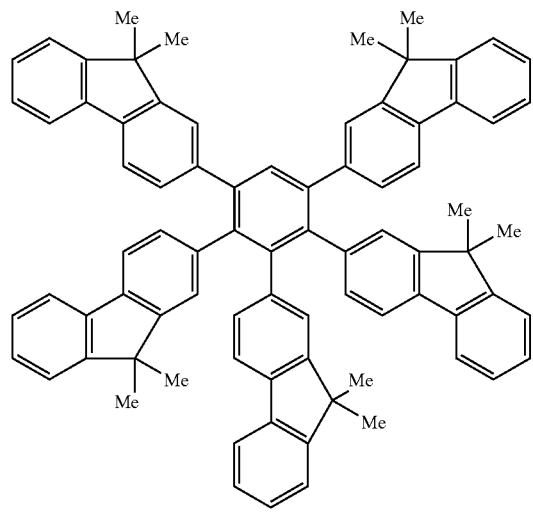
[5]-1
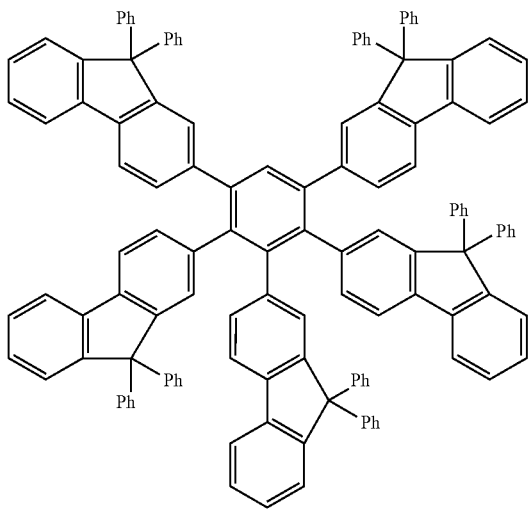
[5]-2
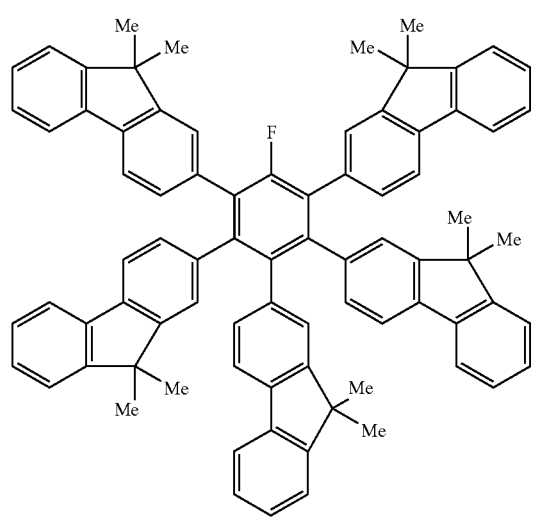
[5]-3

-continued
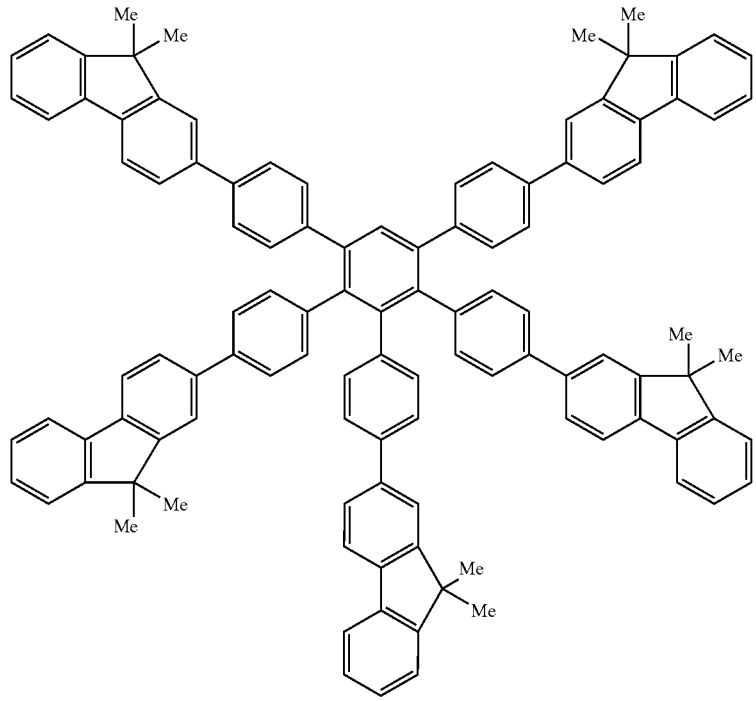
[5]-4
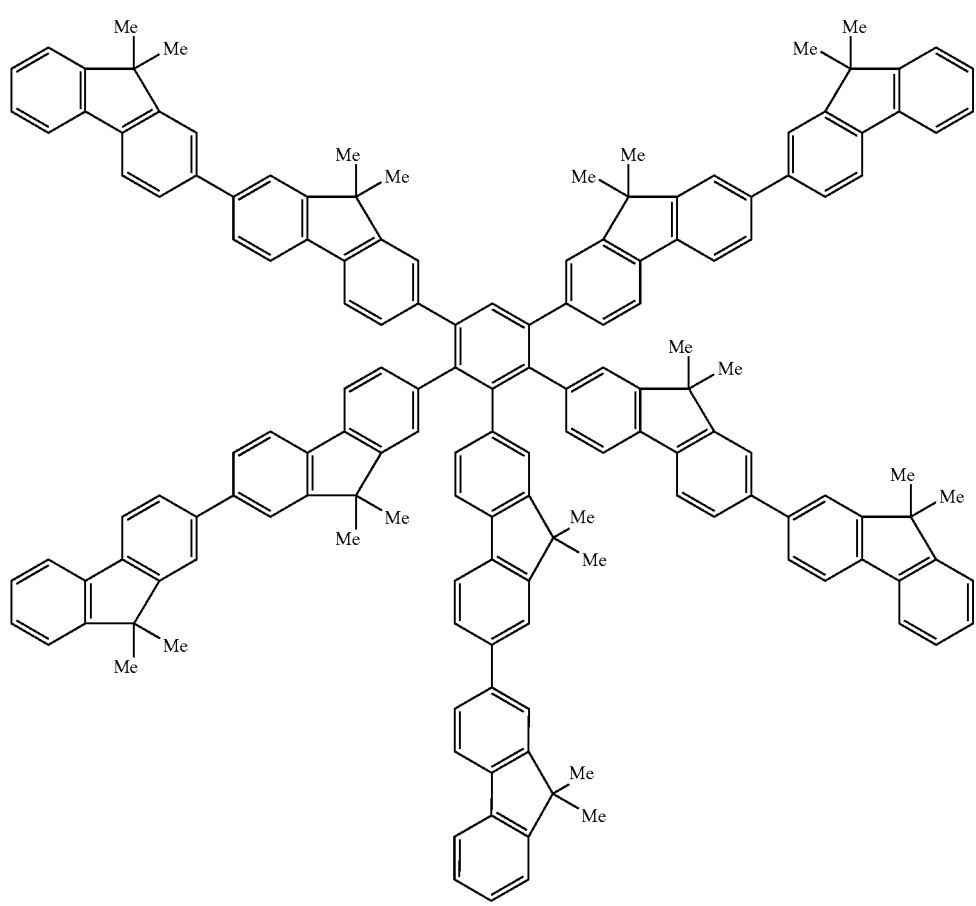
[5]-5

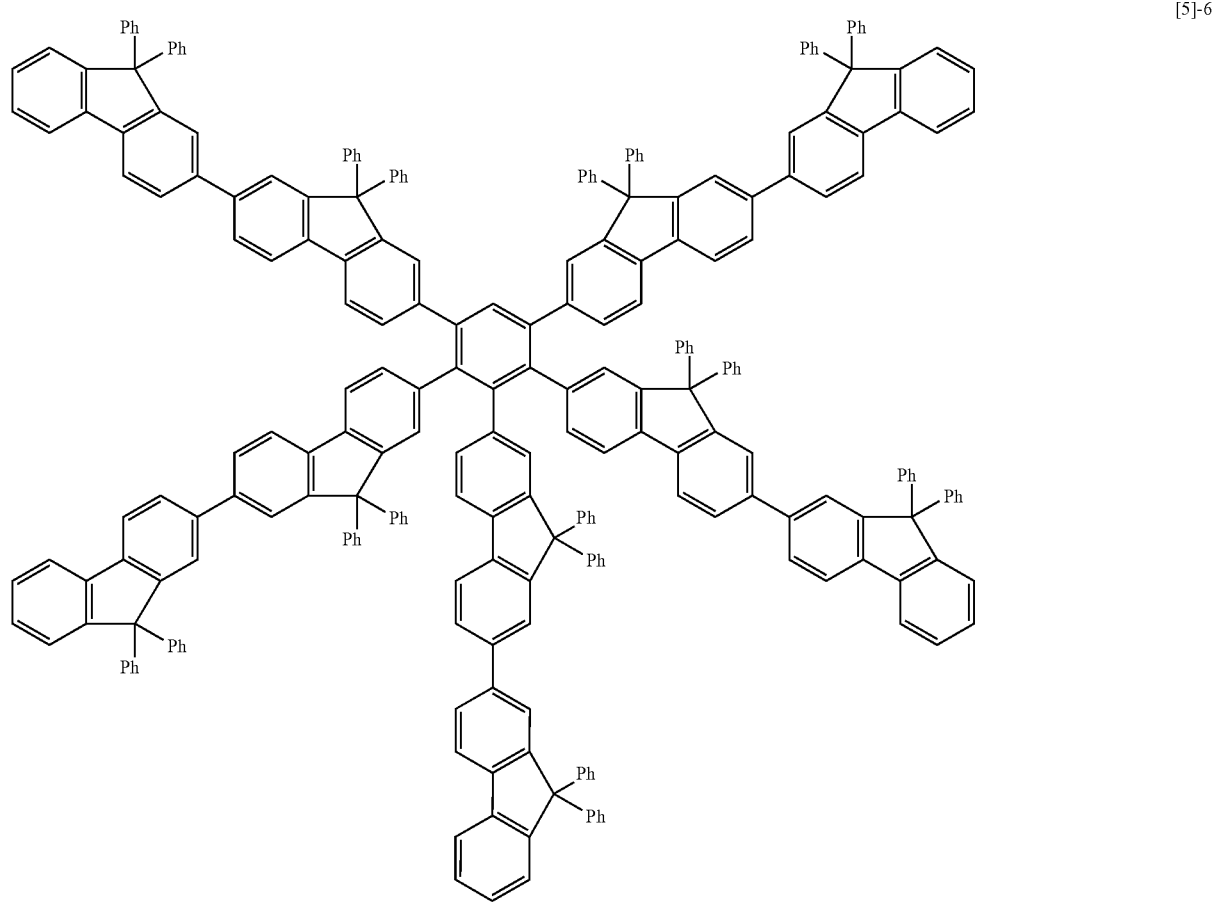
[5]-6
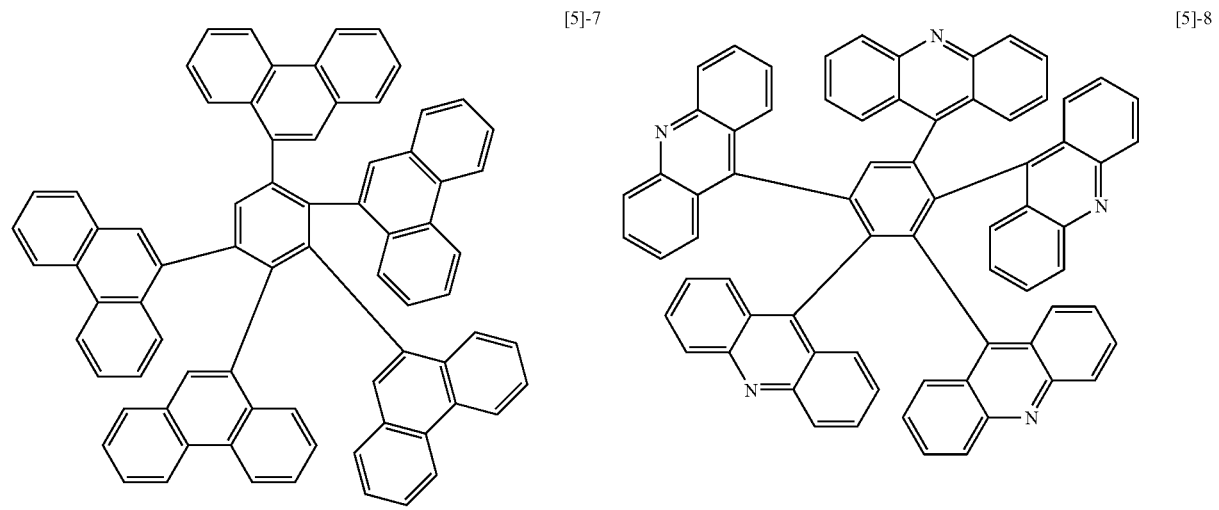
[5]-7 [5]-8

[5]-9
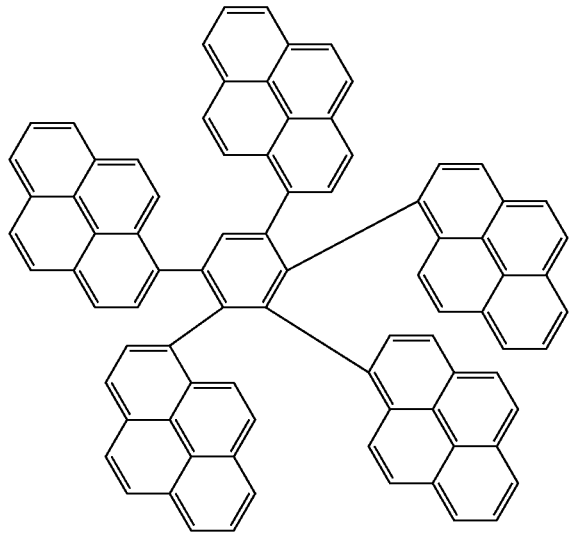
[5]-10
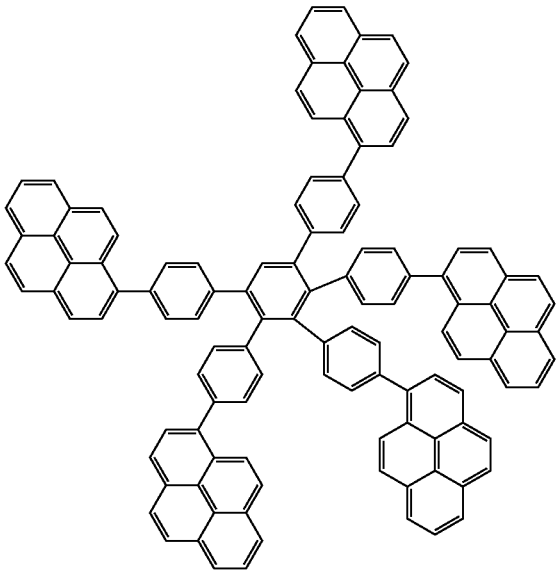
[5]-11
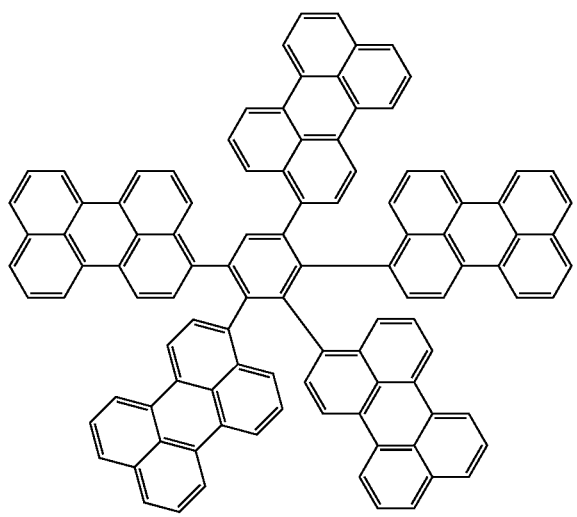
[5]-12
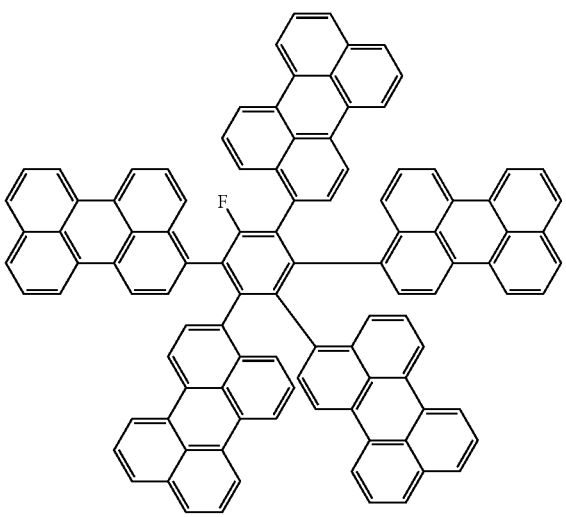

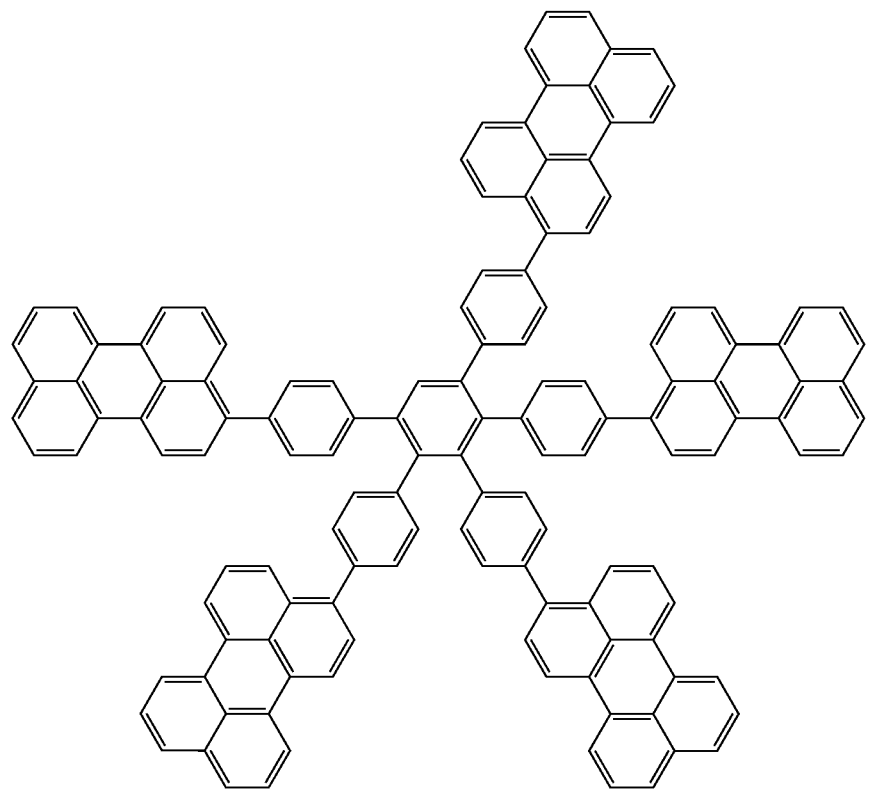
[5]-13
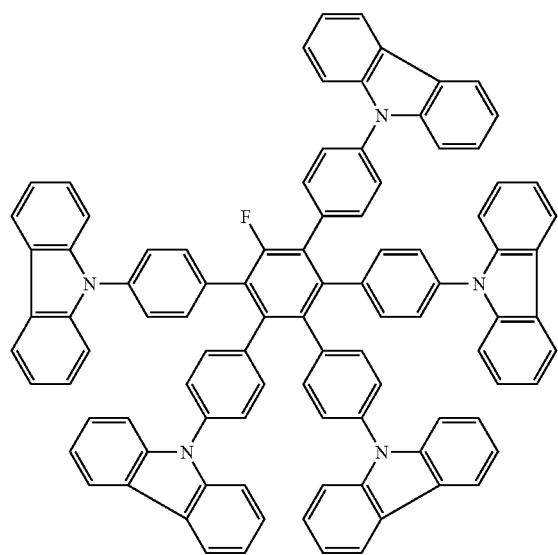
[5]-14
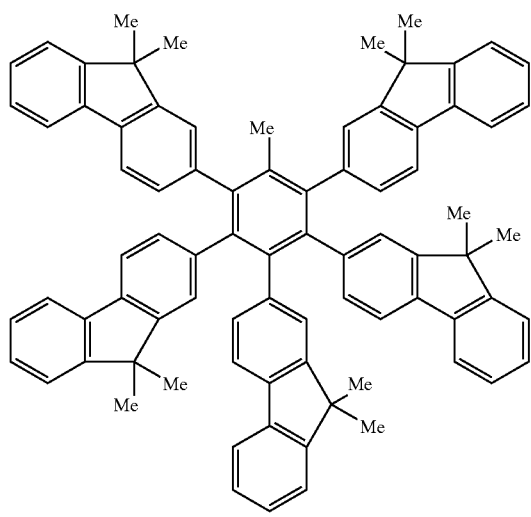
[5]-15

-continued
[5]-16
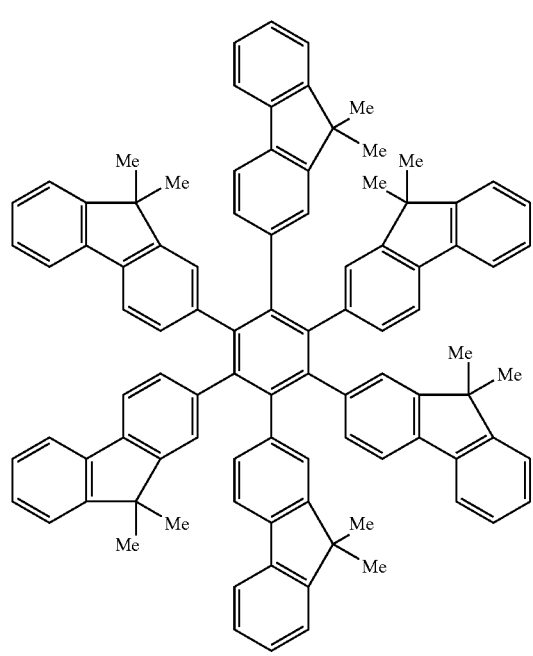
[5]-17
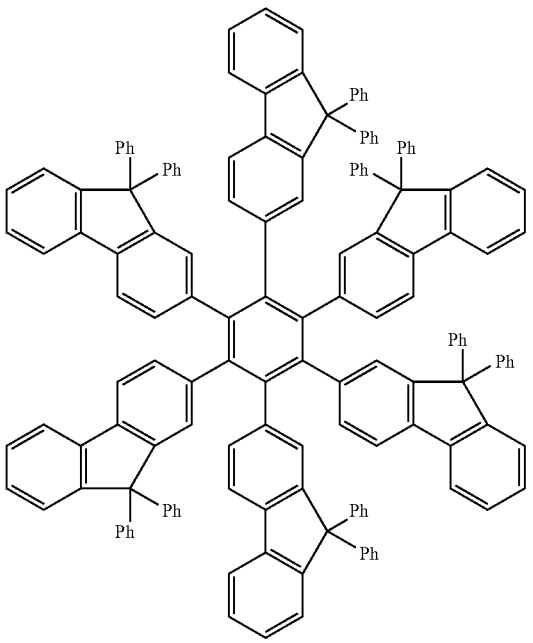
[5]-18
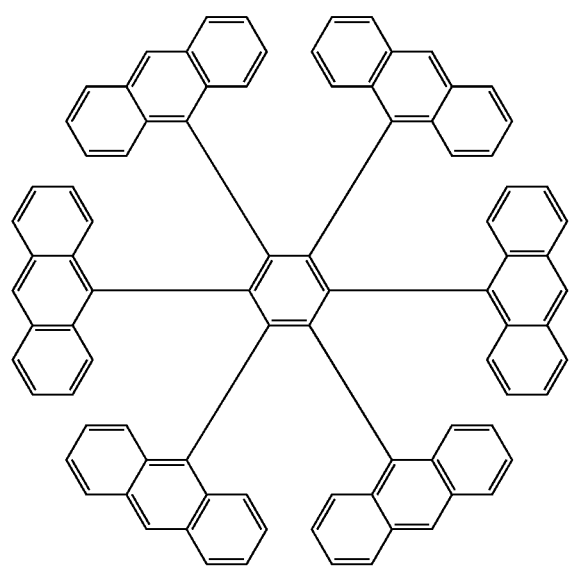
[5]-19
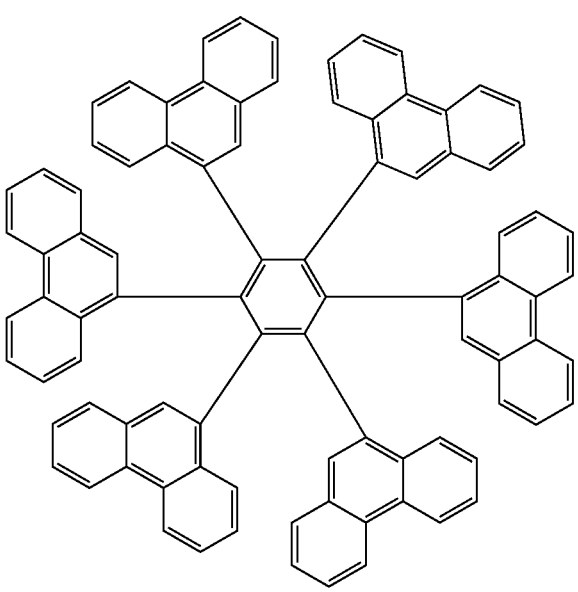

[5]-20
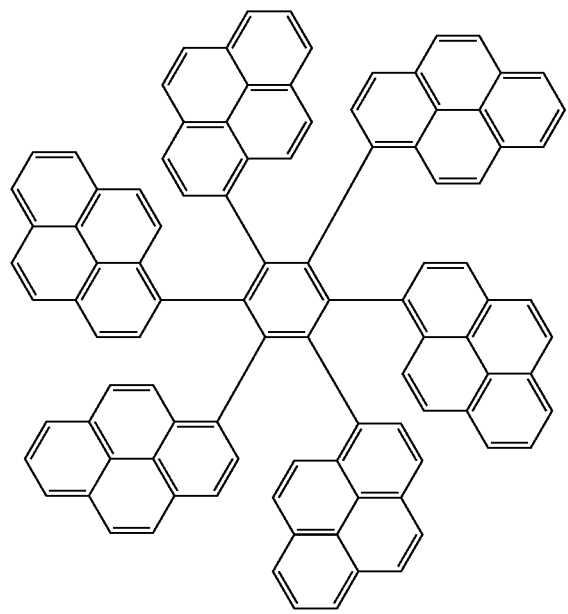
[5]-21
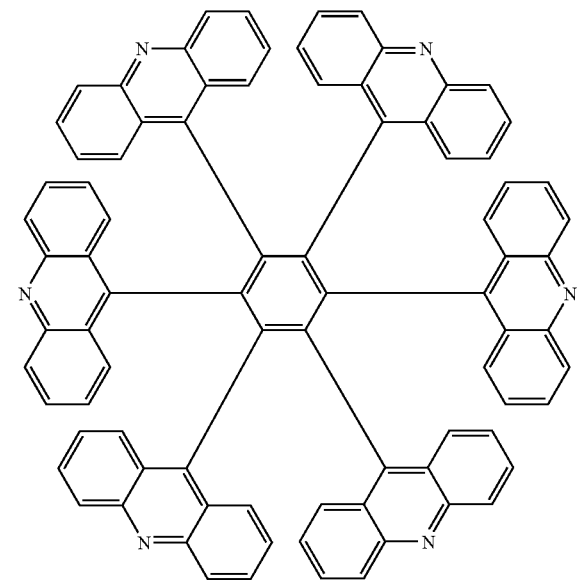
[6]
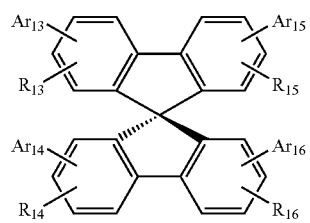
[6]-1
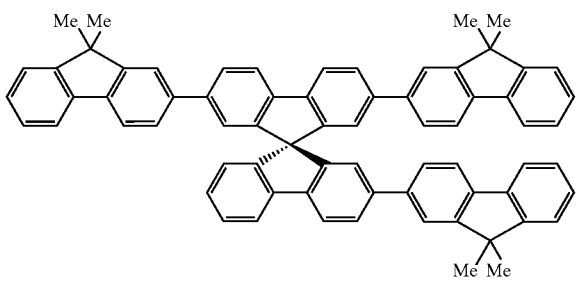
[6]-2
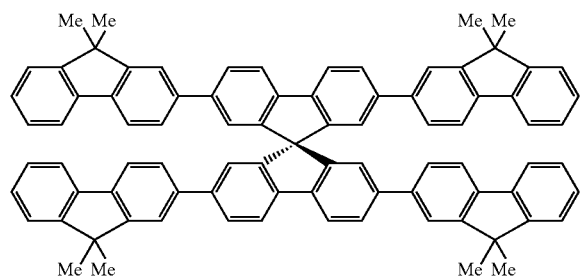
[6]-3
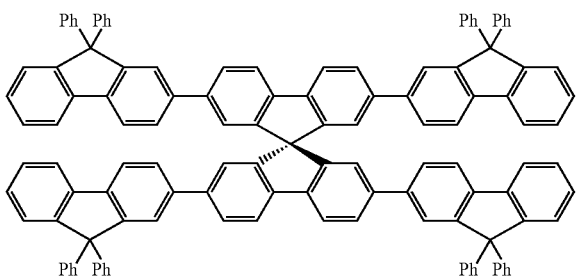
[6]-4
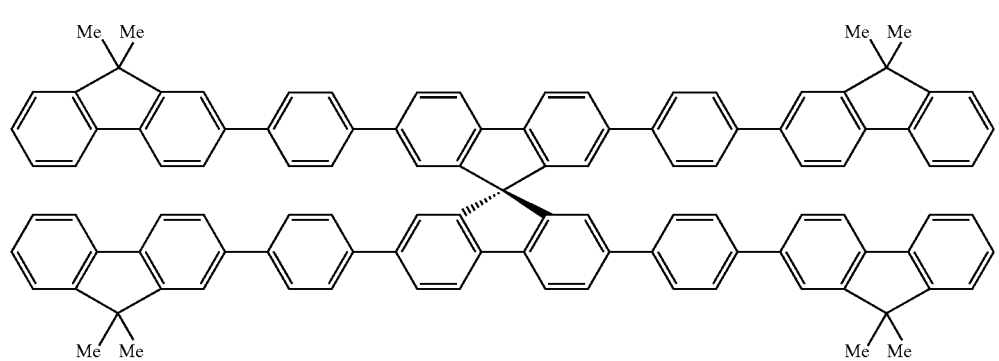

-continued
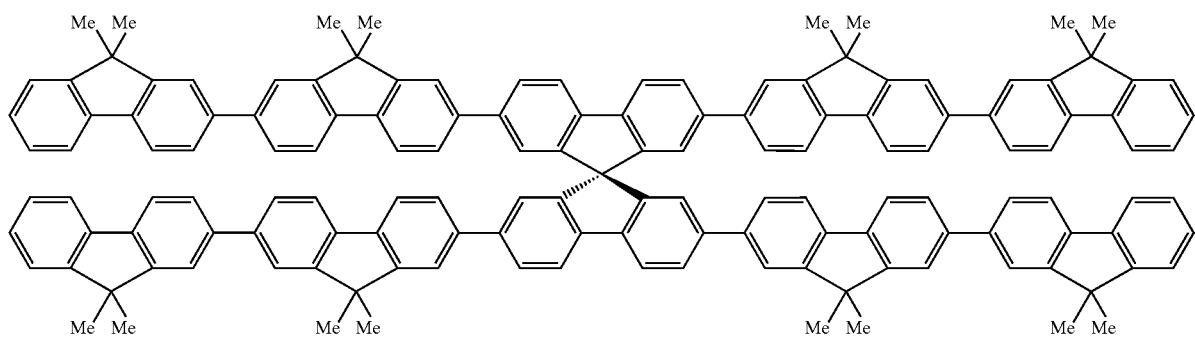
[6]-5
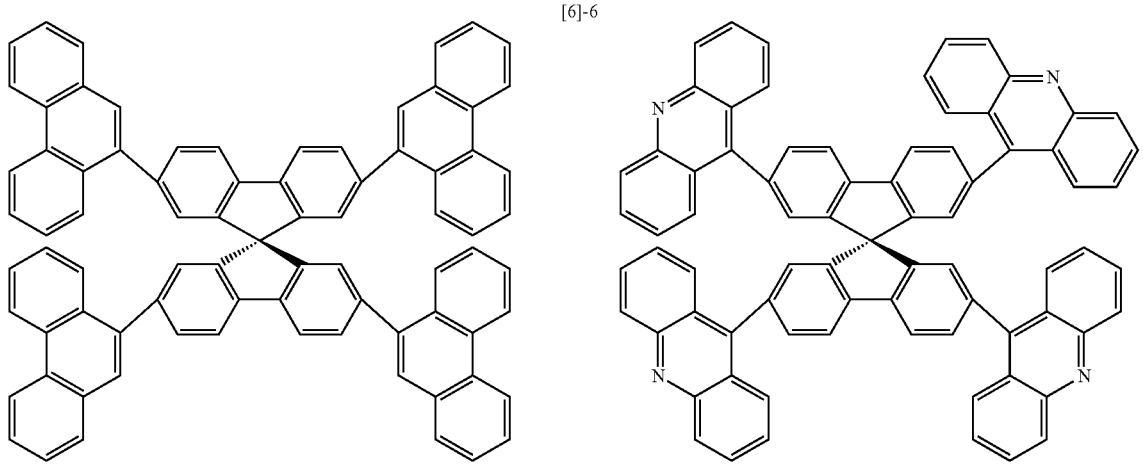
[6]-6
[6]-7
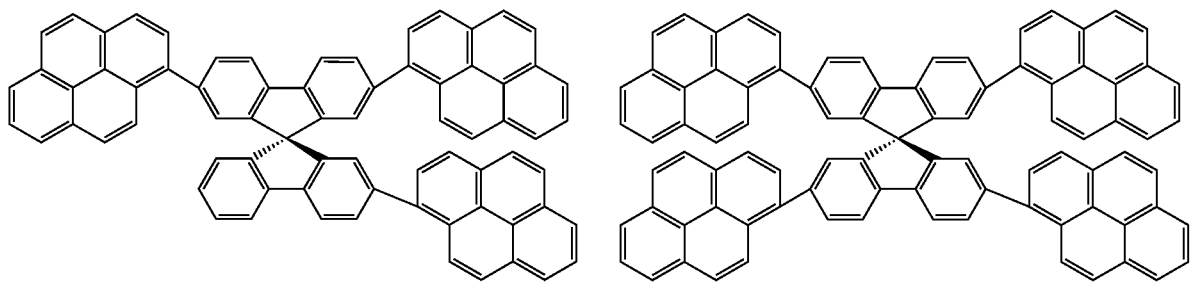
[6]-8
[6]-9
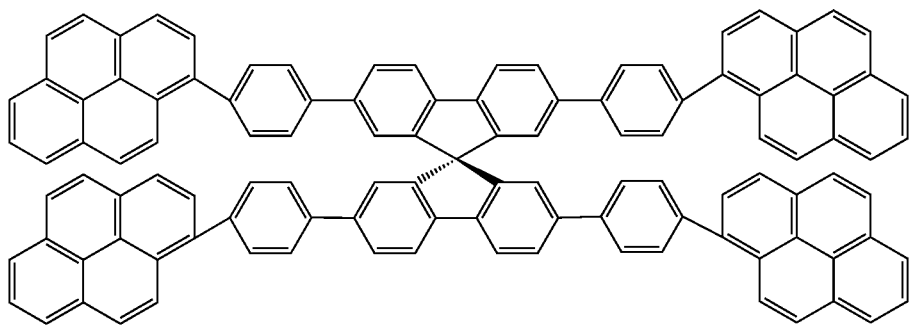
[6]-10

-continued
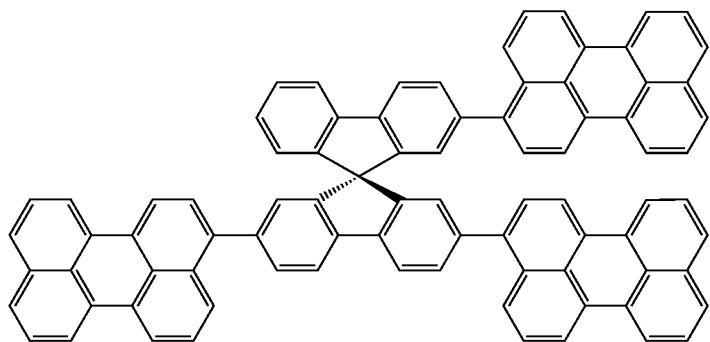
[6]-11
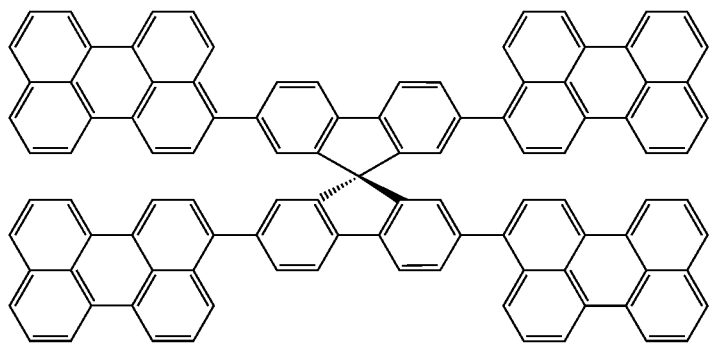
[6]-12
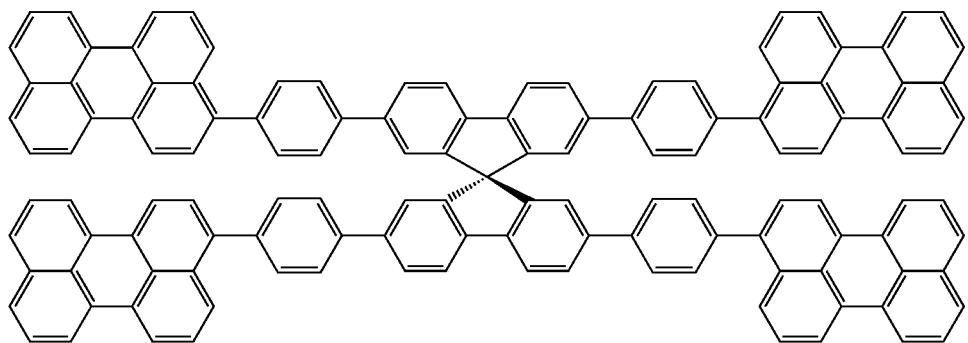
[6]-13
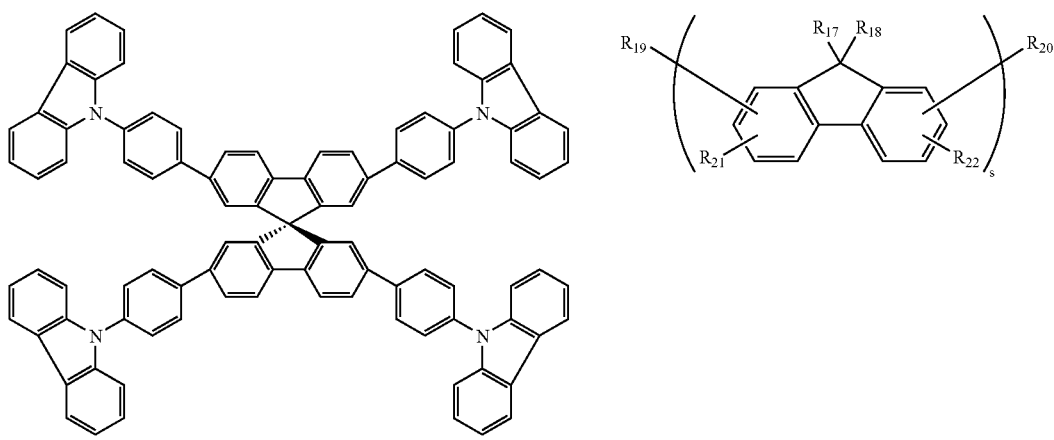
[6]-14 [7]

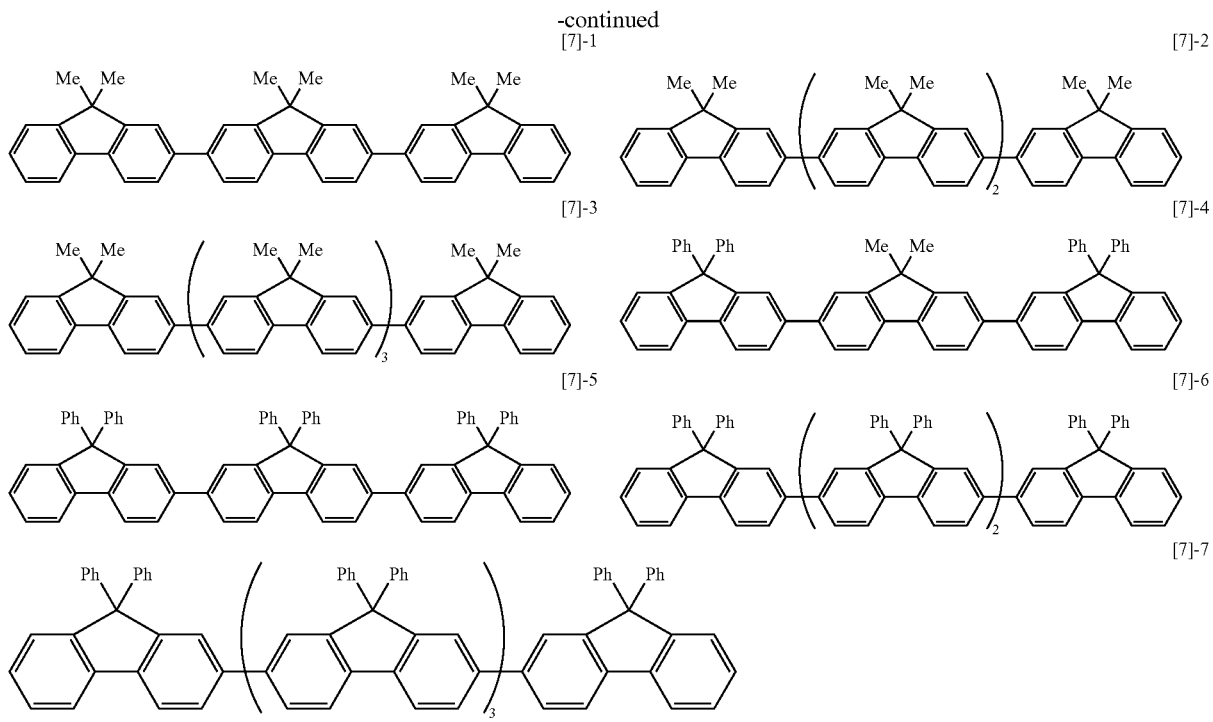

The preferable examples of the organic light-emitting device of the present invention are shown in FIGS. 1 to 6.

FIG. 1 is a cross-sectional view showing an example of the organic light-emitting device according to the present invention. FIG. 1 shows a structure in which an anode 2, a light-emitting layer 3 and a cathode 4 are formed on a substrate 1 in this order. The light-emitting device used here is useful in the case where it has all the properties of hole-transporting ability, electron-transporting ability and the light-emitting ability by itself, or in the case where compounds having each of these properties respectively are mixed and used.

Figure 2:
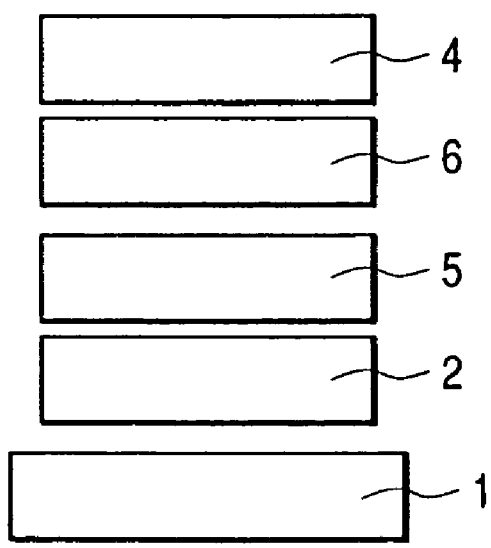
FIG. 2 is a cross-sectional view showing another example of the organic light-emitting device according to the present invention.

FIG. 2 is a cross-sectional view showing another example of the organic light-emitting device according to the present invention. FIG. 2 shows a structure in which an anode 2, a hole-transporting layer 5, an electron-transporting layer 6 and a cathode 4 are formed on a substrate 1 in this order. This structure is useful in the case where a light-emitting material having either one or both of hole-transporting ability and electron-transporting ability is used for the respective layer in combination with a hole-transporting or electron-transporting compound which has no light-emitting properties. A light-emitting layer 3 consists of either the hole-transporting layer 5 or the electron-transporting layer 6 in this case.

Figure 3:
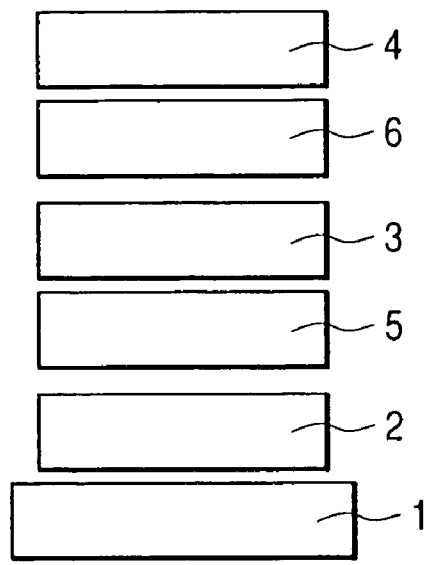
FIG. 3 is a cross-sectional view showing another example of the organic light-emitting device according to the present invention.

FIG. 3 is a cross-sectional view showing another example of the organic light-emitting device of the present invention. FIG. 3 shows a structure in which an anode 2, a hole-transporting layer 5, a light-emitting layer 3, an electron-transporting layer 6 and a cathode 4 are formed on a substrate 1 in this order. Since this structure separates the functions of carrier transport and luminescence, it can be used in a suitable combination with compounds having hole-transporting ability, electron-transporting ability and light-emitting ability, thus extremely enhancing the flexibility of selection of materials and enabling various compounds which differ in luminescence wavelength to be used, thereby enabling diversification of luminescence hue. Furthermore, it also becomes possible to effectively confine each of the carriers or excitons in the light-emitting layer 3 positioned in the middle, and to aim at improvement in luminescence efficiency.

Figure 4:
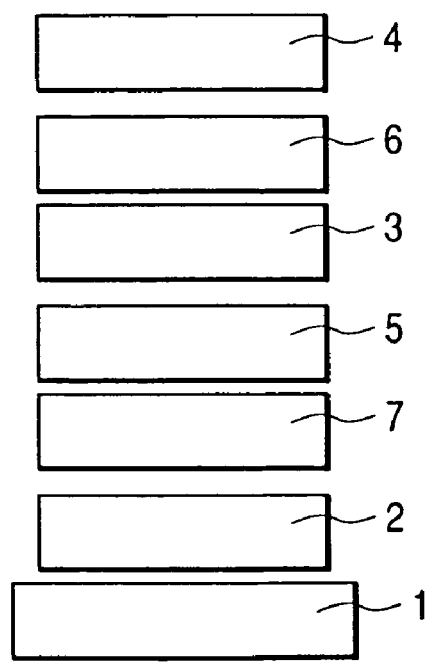
FIG. 4 is a cross-sectional view showing another example of the organic light-emitting device according to the present invention.

FIG. 4 is a cross-sectional view showing another example of the organic light-emitting device of the present invention. FIG. 4 shows a structure in which a hole injecting layer 7 is inserted in the side of an anode 2 as compared with that of FIG. 3 and that has an effect in improving the close contact of the anode 2 and a hole-transporting layer 5 or improving hole injecting properties and is effective for reduction in voltage.

Figure 5:
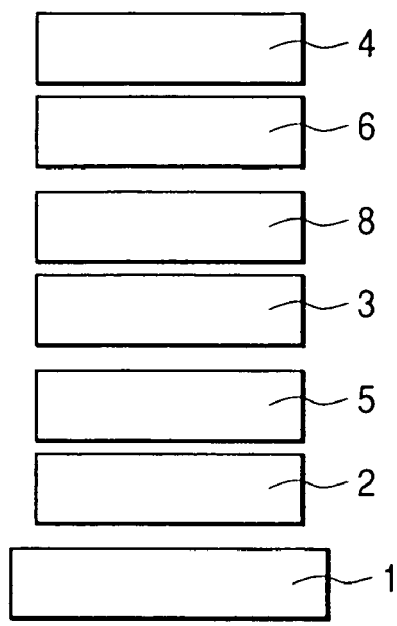
FIG. 5 is a cross-sectional view showing another example of the organic light-emitting device according to the present invention.
Figure 6:
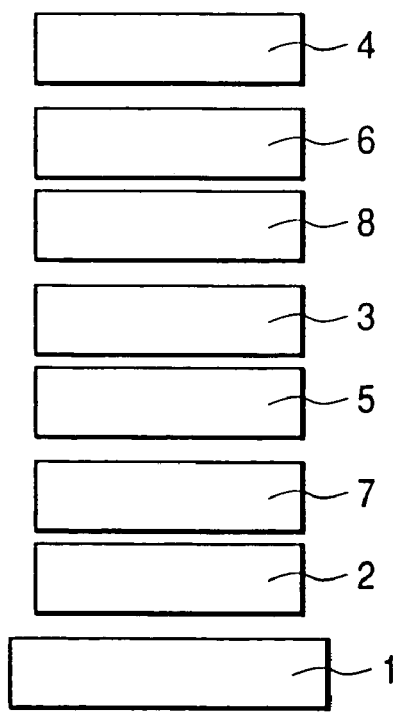
FIG. 6 is a cross-sectional view showing another example of the organic light-emitting device according to the present invention.

FIGS. 5 and 6 are cross-sectional views showing other examples of the organic light-emitting device of the present invention. FIGS. 5 and 6 show structures in which a layer inhibiting holes or excitons from escaping to the side of a cathode 4 (hole blocking layer 8) is inserted between a light-emitting layer 3 and an electron-transporting layer 6, in comparison with the structures of FIGS. 3 and 4. By using a compound having a very high ionization potential as the hole blocking layer 8, these structures are effective for improving the luminescence efficiency.

However, FIGS. 1 to 6 merely show very fundamental device structures, and the construction of the organic light-emitting device using the compound of the present invention is not limited to these. For example, various layer configurations can be taken including providing an insulating layer on the interface between the electrode and the organic layer, providing an adhesive layer or interference layer, or making a hole-transporting layer consisting of two layers different in ionization potential.

The monoaminofluorene compound represented by the general formula [1] or [2] used for the present invention can be used in any embodiment of FIGS. 1 to 6.

Especially the organic layer using the compound of the present invention is useful as a light-emitting layer, an electron-transporting layer or a hole-transporting layer, and the layer formed by the vacuum evaporation method, the solution applying method or the like is excellent in stability with the passage of time since crystallization thereof cannot readily take place.

Although the present invention uses the monoaminofluorene compound represented by the general formula [1] or [2] particularly as a component of a light-emitting layer, it can also be used, if needed, together with a hole-transporting compound, a luminescent compound or an electron-transporting compound known in the art.

Examples of these compounds are given below.

Hole-transporting Compound

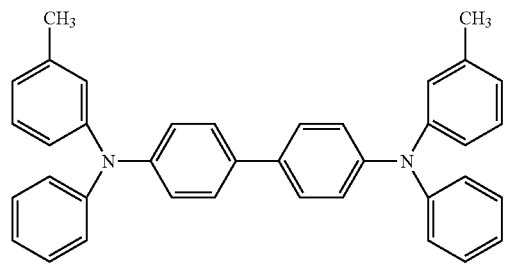

TPD

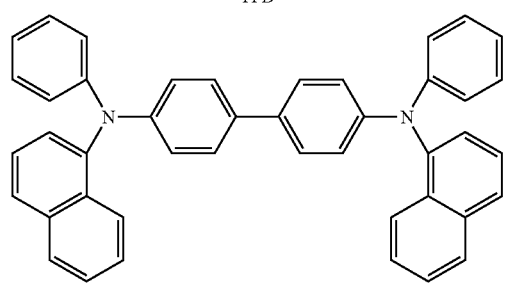

α-NPD

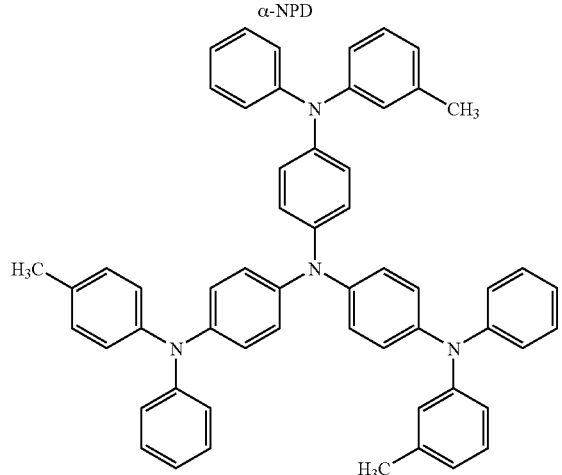

m-MTDATA

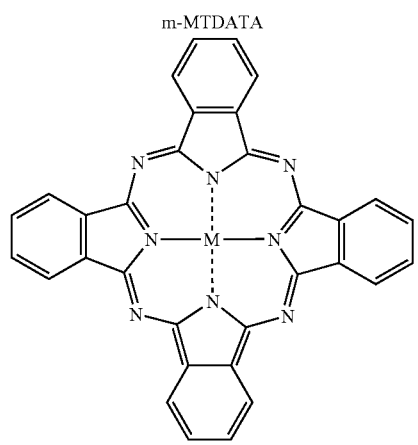

Pc-M
M: Cu, Mg, AlCl, TiO, SiCl$_2$, Zn, Sn, MnCl, GaCl, etc

-continued

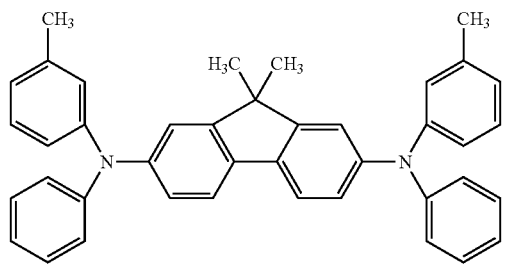

DTDPFL

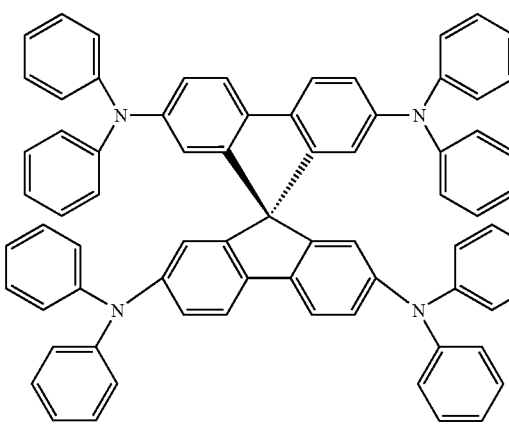

spiro-TPD

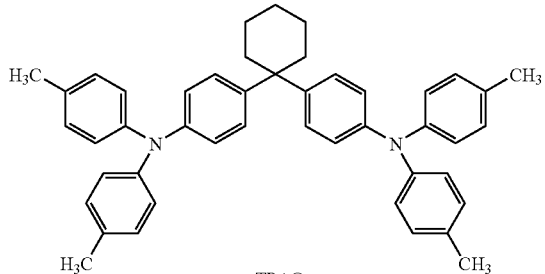

TPAC

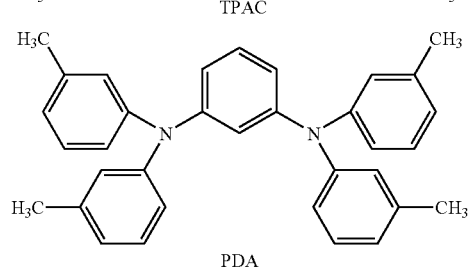

PDA

Electron-transporting Light-emitting Material

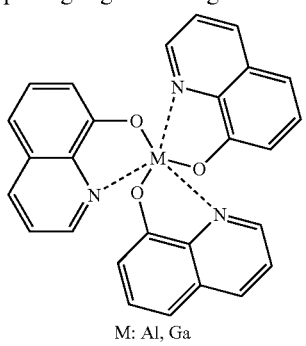

M: Al, Ga

-continued
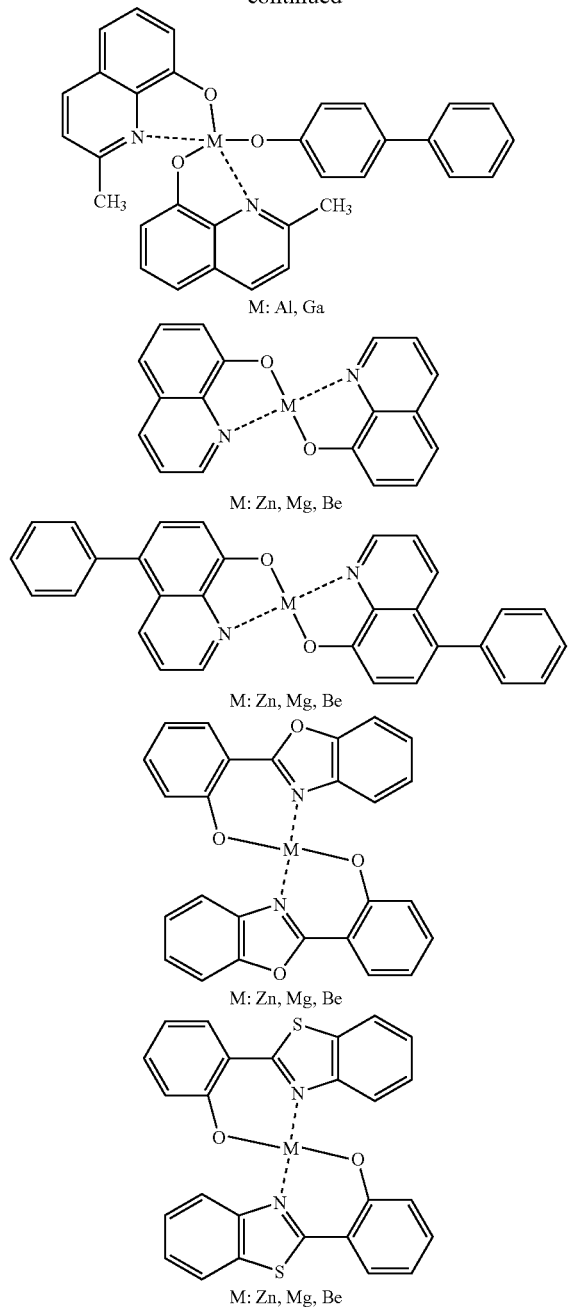
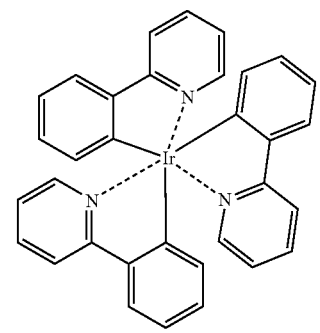
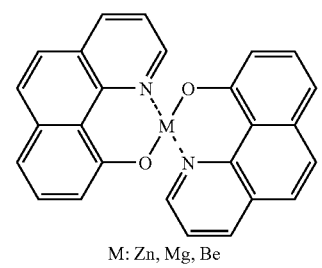
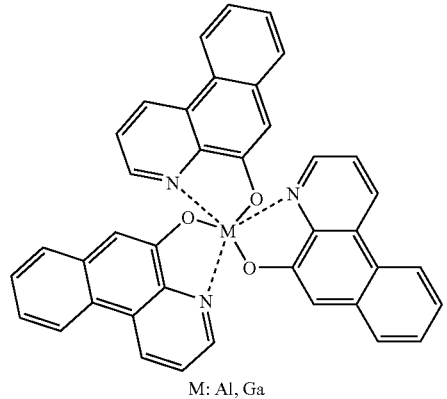
Light-emitting Material
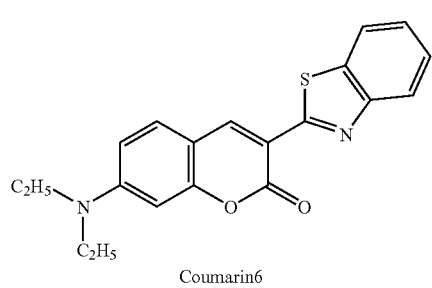
Coumarin6
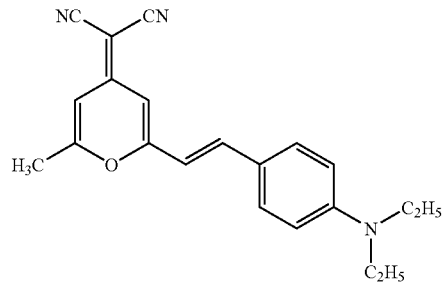
DCM-1

-continued
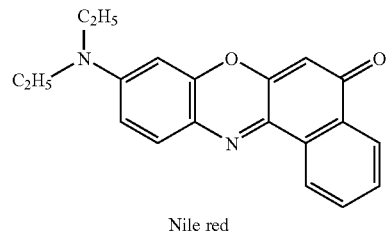
Nile red
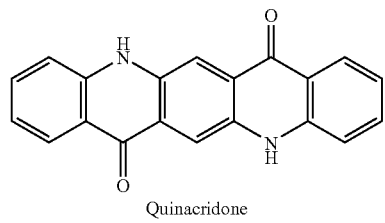
Quinacridone
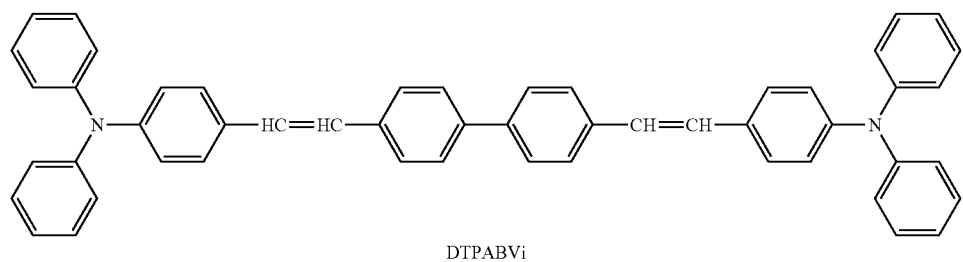
DTPABVi
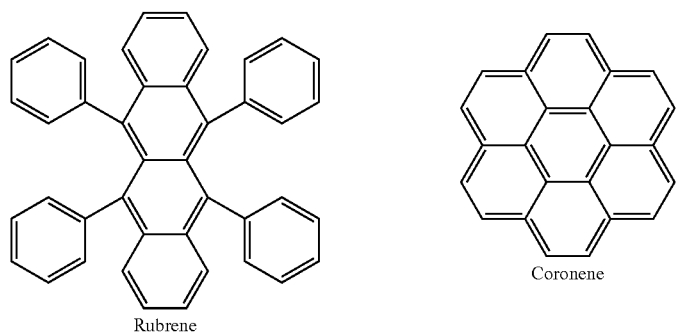
Rubrene
Coronene
Matrix Material of Light-emitting Layer and Electron-transporting Material
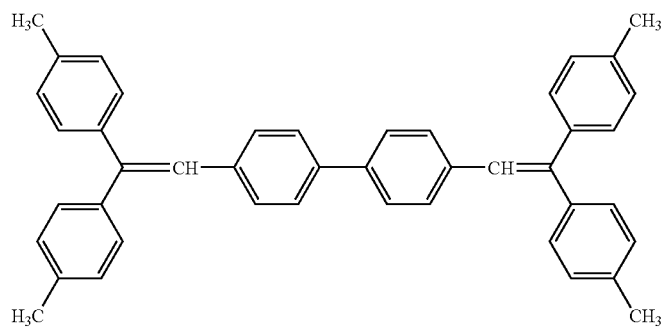

-continued
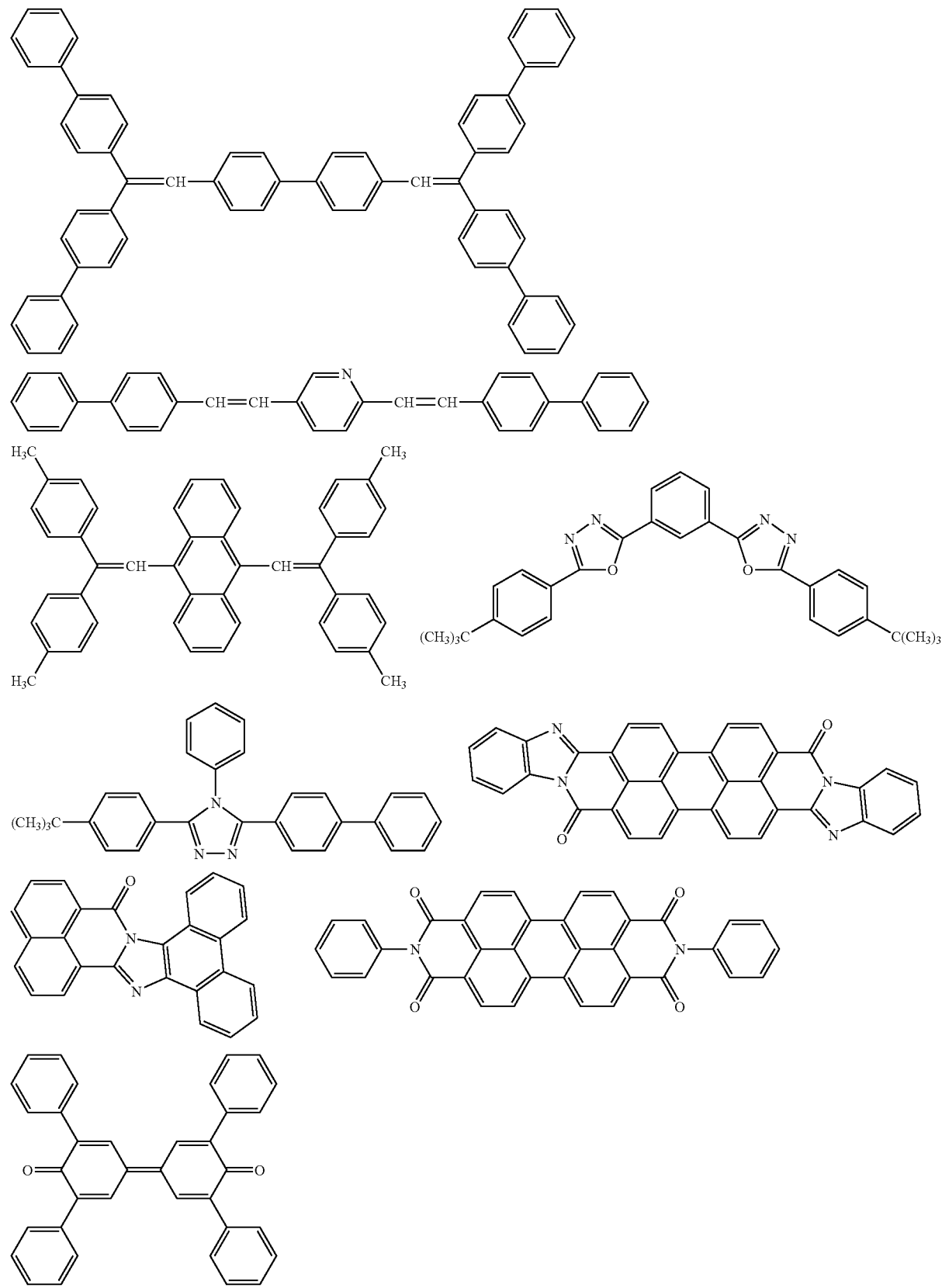

Hole-transporting Polymer Material
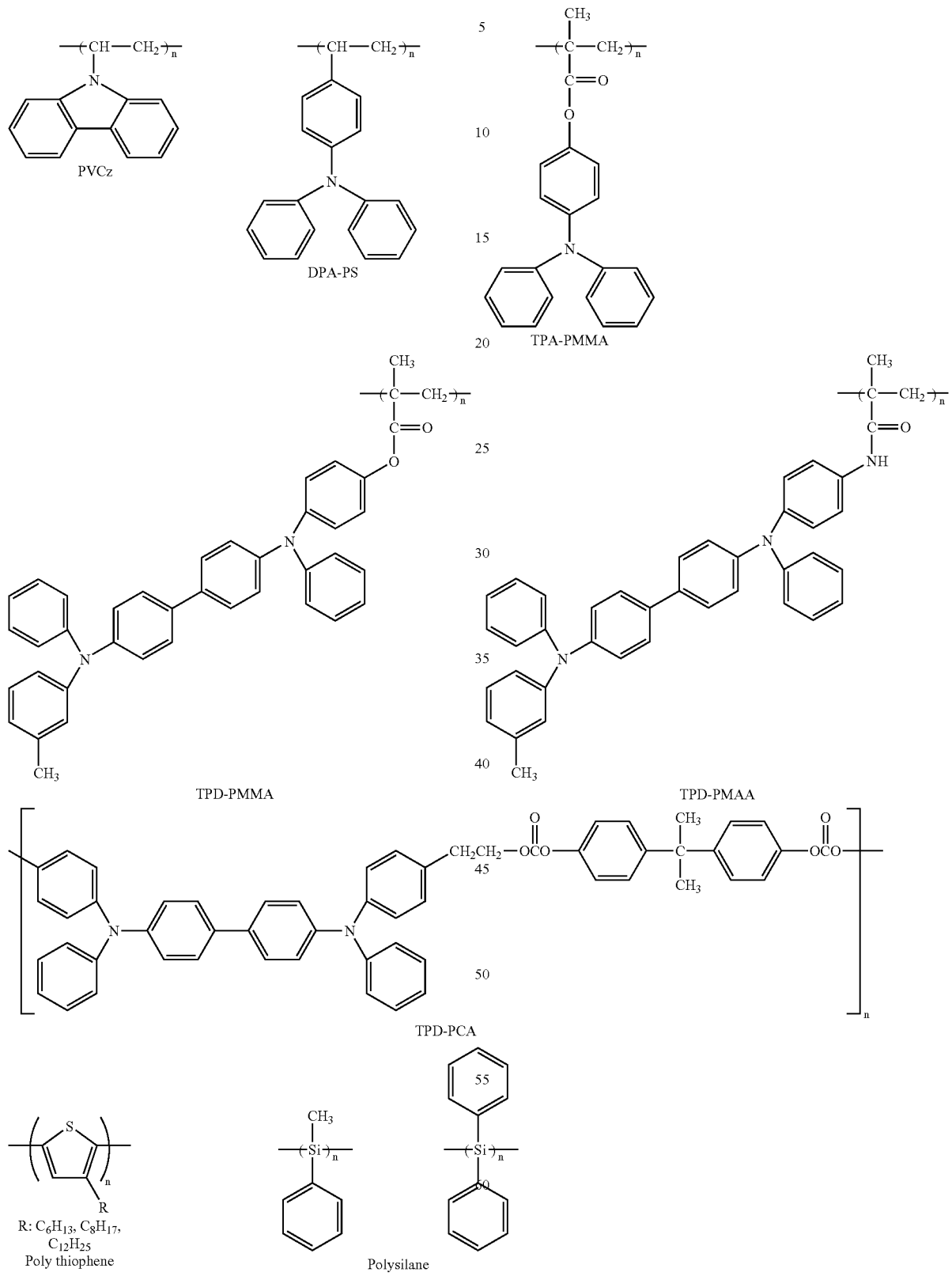

Light-emitting and Electron-transporting Polymer Material

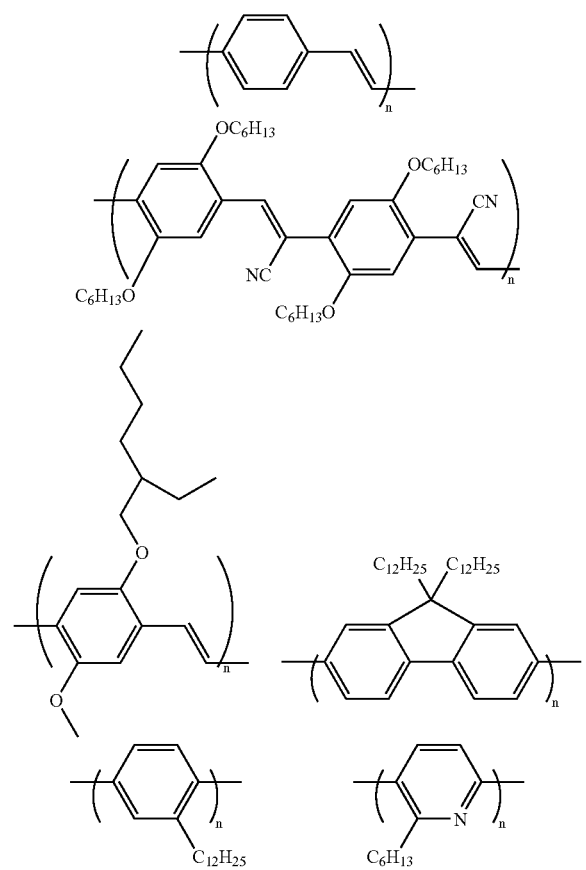

In the organic light-emitting device of the present invention, the layer containing the monoaminofluorene compound represented by the general formula [1] or [2] and the layer consisting of other organic compounds can be generally formed into a thin film by the vacuum evaporation method or by the applying method by dissolving the compounds in a suitable solvent. When film forming is conducted especially by the applying method, the film can also be formed in combination with a suitable binding resin.

The above-mentioned binding resin can be selected from a wide range of binding resins and examples thereof include poly(vinyl carbazole) resin, polycarbonate resin, polyester resin, polyallylate resin, polystyrene resin, acrylic resin, methacrylic resin, butyral resin, poly(vinyl acetal) resin, diallyl phthalate resin, phenol resin, epoxy resin, silicone resin, polysulphone resin, urea resin, etc. but are not limited to these. These resins may be used alone or mixed as a copolymerized polymer of one or more types of them.

As an anode material, those having as high a work function as possible is suitable, and for example, a metal element such as gold, platinum, nickel, palladium, cobalt, selenium, and vanadium, or alloys thereof, and metal oxides such as tin oxide, zinc oxide, indium tin oxide (ITO) and indium zinc oxide can be used. Conductive polymers such as polyaniline, polypyrrole, polythiophene and polyphenylenesulfide can also be used. These electrode substances may be used alone and two or more of them can also be used in combination.

On the other hand, as a cathode material, those having a low work function is suitable and a metal element such as lithium, sodium, potassium, calcium, magnesium, aluminum, indium, silver, lead, tin and chromium or alloys of two or more thereof can be used. Use of a metal oxide such as indium tin oxide (ITO) is also possible. The cathode may be in a single layer structure or can take a multilayer structure.

Substrate used in the present invention is not limited, but a non-transparent plate such as metal substrate and ceramics substrate, a transparent plate such as glass, quartz, and a plastic sheet can be used. It is also possible to use a color filter film, a fluorescent color conversion filter film, a dielectric reflective film, etc. on the substrate to control the color of the emitted light.

In addition, a protection layer or seal layer can also be provided on the formed device in order to prevent contact with oxygen, moisture, etc. The protection layer may include inorganic material films such as a diamond thin film, a metal oxide film and a metal nitride film, polymer films such as those of a fluororesin, polyparaxylene, polyethylene, silicone resin and polystyrene resin as well as light curable resin, etc. Moreover, the device may be covered with glass, a gas impermeable film, metal, etc., and the device itself may be packaged in a suitable sealing resin.

Hereainfter, the present invention will be described by non-limiting examples still more specifically.

EXAMPLE 1

Preparation Process of Example Compound No. [1]-43

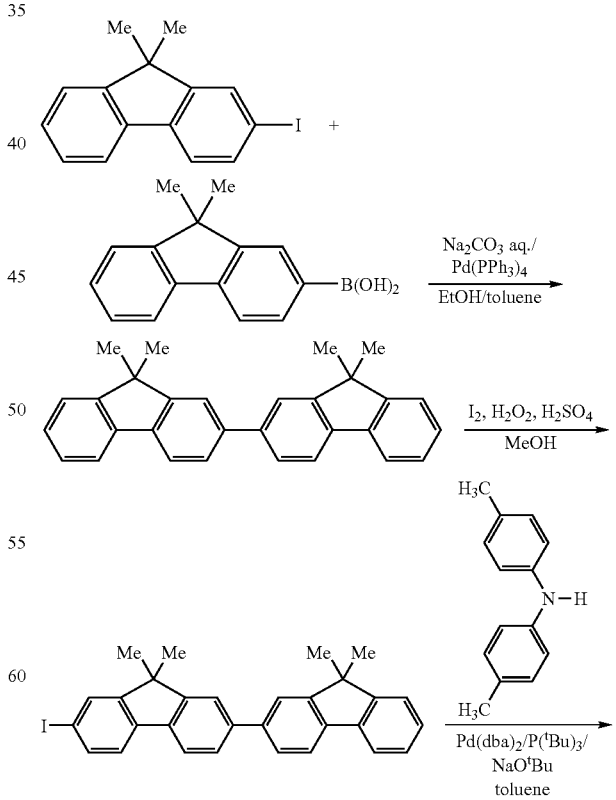

115

-continued

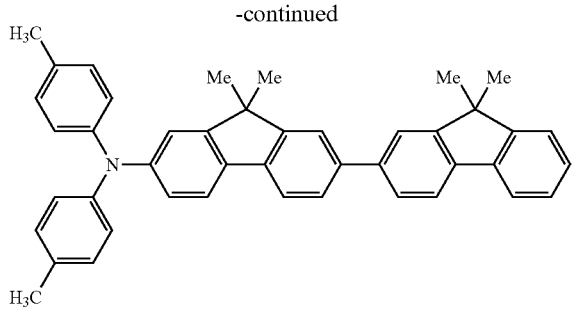

[1]-43

2 g (6.25 mmol) of 2-iodo-9,9-dimethylfluorene and 1.5 g (4.12 mmol) of 2-(dihydroxyboranyl)-9,9-dimethylfluorene were dissolved in the mixed solvent (80 ml of degassed toluene and 40 ml of ethanol) and agitated under nitrogen flow, and 41 ml of sodium carbonate solution which was prepared by dissolving 9 g of anhydrous sodium carbonate in 45 ml of water was added dropwise thereto. After agitating for 30 minutes, 238 mg (0.206 mmol) of tetrakis(triphenylphosphine) palladium was added. Heating with agitation was carried out on the oil bath heated at 80° C. for about 5 hours. After cooling the reaction solution to room temperature, 50 ml of water and 50 ml of ethyl acetate were added, the aqueous layer and the organic layer were separated, the aqueous layer was further extracted with toluene and ethyl acetate, and the extract combined with the above organic layer was dried over magnesium sulfate. The solvent was evaporated, the residual substance was refined by silica gel column chromatography (toluene:hexane=1:2), and 1.5 g of bis(9,9-dimethylfluorene) was obtained.

116

4.2 g (10.9 mmol) of bis(9,9-dimethylfluorene), 1.38 g (5.43 mmol) of iodine and 0.5 g of 50% sulfuric acid were dissolved in 80 ml of methanol and agitated with heating on the oil bath heated at 60° C., and about 1 g of 35% by weight aqueous hydrogen peroxide was added dropwise thereto. After cooling the reaction solution to room temperature, 30 ml of water was added and the deposited crude crystal was separated by filtration. The crude crystal was refined by silica gel column chromatography (toluene:hexane=1:2), and 5.0 g of monoiodide of bis(9,9-dimethylfluorene) was obtained.

113 mg (0.2 mmol) of palladium bis(benzylideneacetone) and 120 mg (0.6 mmol) of tri-tert-butylphosphine were dissolved in 40 ml of toluene under nitrogen flow, and agitated at room temperature for 15 minutes. 1.02 g (2 mmol) of monoiodide of bis(9,9-dimethylfluorene) dissolved in 50 ml of toluene was added dropwise thereto, and agitated for 30 minutes. 0.59 g (3 mmol) of bis(4-methylphenyl)amine dissolved in 50 ml of toluene was also added dropwise thereto, and subsequently 0.43 g (4.5 mmol) of sodium tert-butoxide was added. Heating with agitation was carried out on the oil bath heated at 120° C. for about 8 hours. After cooling the reaction solution to room temperature, 50 ml of water was added, the aqueous layer and the organic layer were separated, the aqueous layer was further extracted with toluene and ethyl acetate, and the extract combined with the above organic layer was dried over magnesium sulfate. The solvent was evaporated, the residual substance was refined by silica gel column chromatography (toluene:hexane=1:2), and 0.93 g of example compound [1]-43 was obtained.

EXAMPLE 2

Preparation Process of Example Compound No. [1]-60

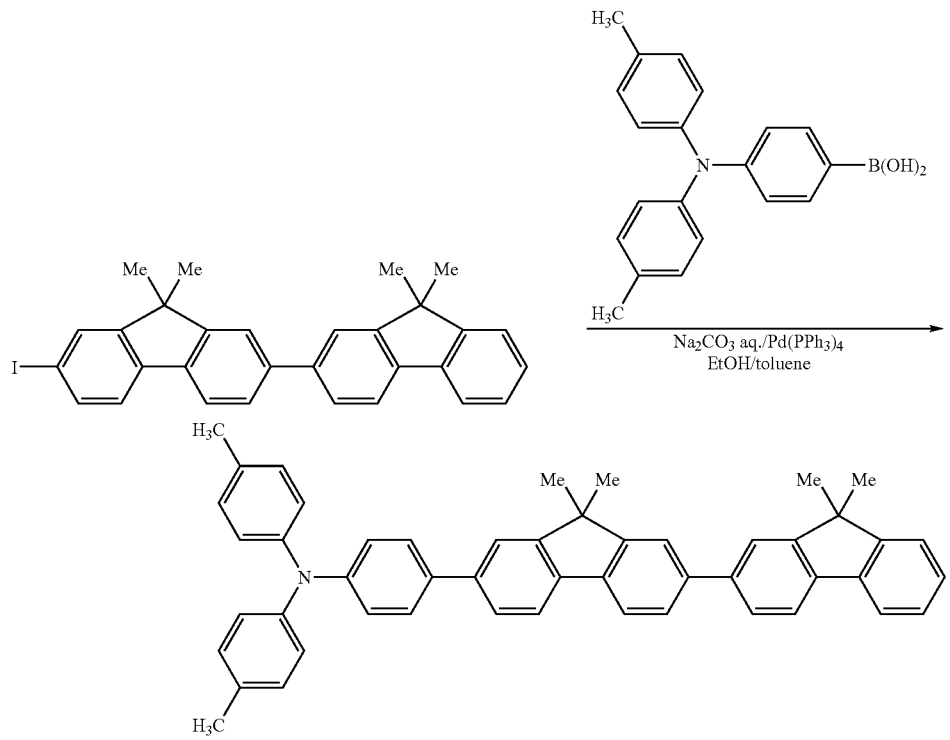

[1]-60

1.02 g (2 mmol) of monoiodide of bis(9,9-dimethylfluorene) and 0.97 g (3 mmol) of bis(4-methylphenyl)aminobenzene-4-boronic acid were dissolved and agitated under nitrogen flow in the mixed solvent (140 ml of degassed toluene and 70 ml of ethanol), and 30 ml of sodium carbonate solution which was prepared by dissolving 6 g of anhydrous sodium carbonate in 30 ml of water was added dropwise thereto. After agitating for 30 minutes, 174 mg (0.15 mmol) of tetrakis(triphenylphosphine)palladium was added. Heating with agitation was carried out on the oil bath heated at 80° C. for about 5 hours. After cooling the reaction solution to room temperature, 70 ml of water and 70 ml of ethyl acetate were added, the aqueous layer and the organic layer were separated, the aqueous layer was further extracted with toluene and ethyl acetate, and the extract combined with the above organic layer was dried over magnesium sulfate. The solvent was evaporated, the residual substance was refined by silica gel column chromatography (toluene:hexane=1:2), and 1 g of example compound [1]-60 was obtained.

EXAMPLE 3

Preparation Process of Example Compound No. [2]-40

6.94 g (21.7 mmol) of 2-iodo-9,9-dimethylfluorene and 1 g (7.25 mmol) of 1,4-phenylenebis(boronic acid) were dissolved and agitated under nitrogen flow in the mixed solvent (120 ml of degassed toluene and 60 ml of ethanol), and 145 ml of sodium carbonate solution which was prepared by dissolving 30 g of anhydrous sodium carbonate in 150 ml of water was added dropwise thereto. After agitating for 30 minutes, 840 mg (0.727 mmol) of tetrakis(triphenylphosphine) palladium was added. Heating with agitation was carried out on the oil bath heated at 80° C. for about 3 hours. After cooling the reaction solution to room temperature, 50 ml of water and 50 ml of ethyl acetate were added, the aqueous layer and the organic layer were separated, the aqueous layer was further extracted with toluene and ethyl acetate, and the extract combined with the above organic layer was dried over magnesium sulfate. The solvent was evaporated, the residual substance was refined by silica gel column chromatography (toluene:hexane=1:2), and 3.02 g of 1,4-phenylenebis(9,9-dimethylfluorene) was obtained.

5.04 g (10.9 mmol) of 1,4-phenylenebis(9,9-dimethylfluorene), 1.38 g (5.43 mmol) of iodine and 0.5 g of 50% sulfuric acid were dissolved in 120 ml of methanol. Heating with

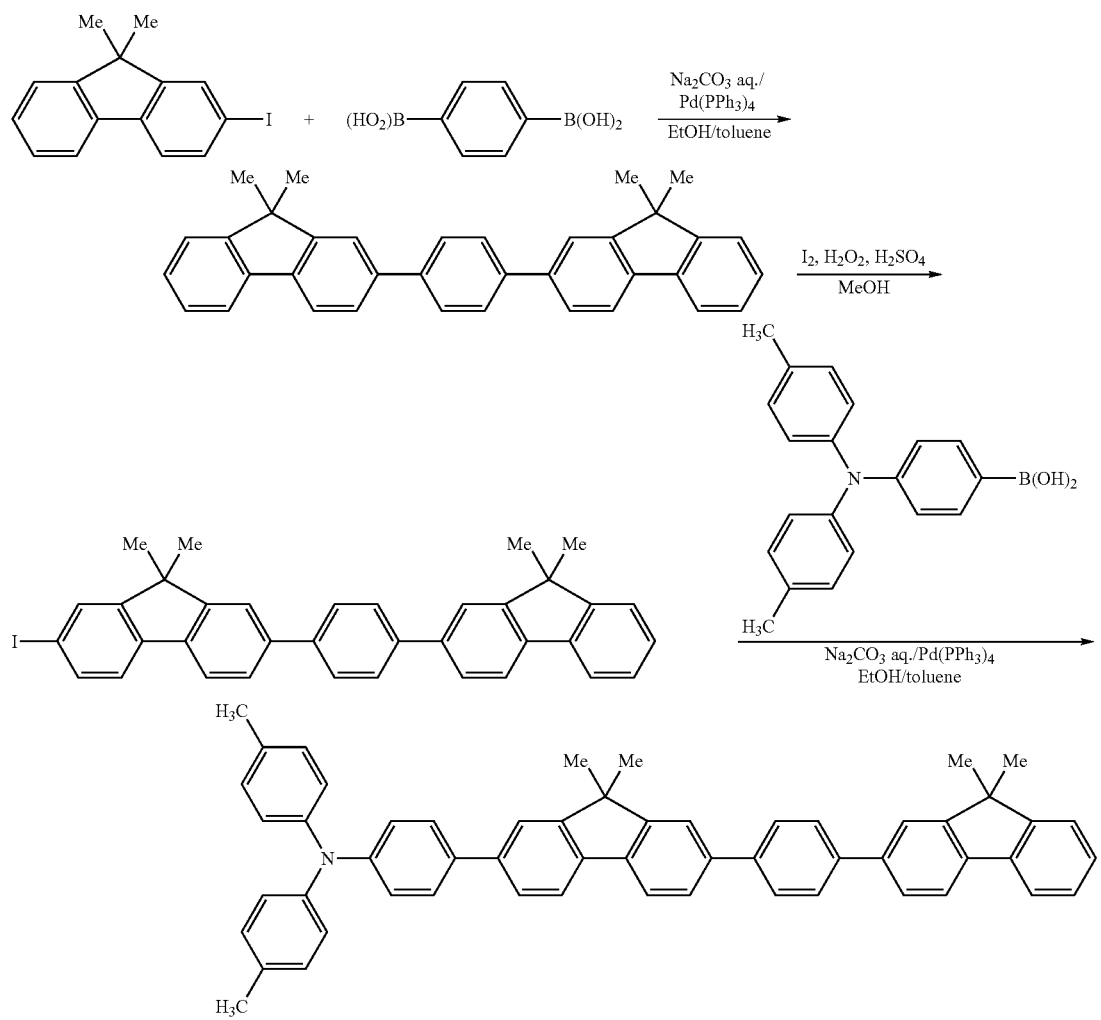

[2]-40 agitation was carried out on the oil bath heated at 60° C., and about 1 g of 35 wt % aqueous hydrogen peroxide was added dropwise thereto. After cooling the reaction solution to room temperature, 30 ml of water was added and the deposited crude crystal was separated by filtration. The crude crystal was refined by silica gel column chromatography (toluene:hexane=1:2), and 5.9 g of monoiodide of 1,4-phenylenebis(9,9-dimethylfluorene) was obtained.

1.18 g (2 mmol) of monoiodide of 1,4-phenylenebis(9,9-dimethylfluorene) and 0.97 g (3 mmol) of bis(4-methylphenyl)aminobenzene-4-boronic acid were dissolved and agitated under nitrogen flow in the mixed solvent (100 ml of degassed toluene and 50 ml of ethanol), and 30 ml of sodium carbonate solution which was prepared by dissolving 6 g of anhydrous sodium carbonate in 30 ml of water was added dropwise thereto. After agitating for 30 minutes, 174 mg (0.15 mmol) of tetrakis(triphenylphosphine)palladium was added. Heating with agitation was carried out on the oil bath heated at 80° C. for about 5 hours. After cooling the reaction solution to room temperature, 60 ml of water and 60 ml of ethyl acetate were added, the aqueous layer and the organic layer were separated, the aqueous layer was further extracted with toluene and ethyl acetate, and the extract combined with the above organic layer was dried over magnesium sulfate. The solvent was evaporated, the residual substance was refined by silica gel column chromatography (toluene:hexane=1:2), and 1.09 g of example compound [2]-40 was obtained.

EXAMPLE 4

The organic light-emitting device of the structure shown in FIG. 3 was prepared by the process shown below.

A glass substrate as the substrate 1 on which a film of indium tin oxide (ITO) having a film thickness of 120 nm as the anode 2 was formed by sputtering method was used as a transparent conductive support substrate. This substrate was subjected to ultrasonic washing in acetone and isopropyl alcohol (IPA) subsequently, boil-washed in IPA and dried. It was further subjected to UV/ozone washing and used as a transparent conductive support substrate.

The compound shown by the following structural formula was used as a hole-transporting material and a chloroform solution thereof was adjusted so that the concentration thereof was 0.5% by weight.

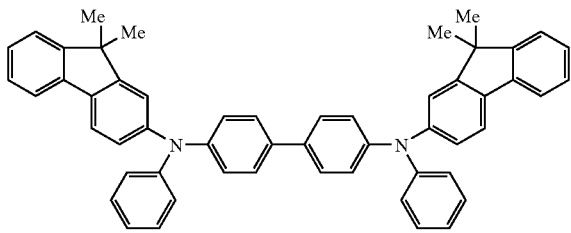

This solution was dropped on the above ITO electrode (anode 2), and spin coating was performed first by rotation at 500 RPM for 10 seconds followed by rotation at 1000 RPM for 1 minute to form a film. It was subsequently dried in a vacuum oven at 80° C. for 10 minutes, and the solvent in the thin film was removed completely. The thickness of the formed TPD film (hole-transporting layer 5) was 50 nm.

Next, vacuum evaporation of the above-mentioned example compound No. [1]-43 was carried out to deposit the compound on the hole-transporting layer 5, and the 20 nm-thick light-emitting layer 3 was formed. The degree of vacuum at the time of vacuum evaporation was $1.0 \times 10^{-4}$ Pa, and the film forming speed was 0.2 to 0.3 nm/sec.

Furthermore, aluminum quinolinol (Alq3) was formed into a film of 40 nm in thickness as an electron-transporting layer 6 by vacuum evaporation method. The degree of vacuum at the time of the vacuum evaporation of these organic layers was $1.0 \times 10^{-4}$ Pa, and the film forming speed was 0.2 to 0.3 nm/sec.

Next, using the vacuum evaporation source material consisting of an aluminum-lithium alloy (lithium concentration 1 atom %), a metal film with a thickness of 10 nm was formed by vacuum evaporation method on the above organic layer, the aluminum film with a thickness of 150 nm was further prepared by vacuum evaporation method, and the organic light-emitting device comprising an aluminum-lithium alloy film as an electron injection electrode (cathode 4) was prepared. The degree of vacuum at the time of vacuum evaporation was $1.0 \times 10^{-4}$ Pa, and the film forming speed was 1.0 to 1.2 nm/sec.

The obtained organic EL device was covered with a glass plate for protection in dry air atmosphere, and sealed with an acrylic resin based adhesive so that the device might not be degraded by adsorption of moisture.

6V was applied to the thus obtained device by using an ITO electrode (anode 2) as a positive electrode and an Al—Li electrode (cathode 4) as a negative electrode. As the result, and blue luminescence of 780 cd/m$^2$ of luminance, maximum luminance of 5900 cd/m$^2$, and luminescence efficiency 0.73 lm/W were observed.

EXAMPLES 5 TO 13

Devices were formed in the same way as in Example 4 except that example compound [1]-43 was replaced with the example compounds shown in Table 14 and evaluated in the same way. The results are shown in Table 14.

TABLE 14

| Example | Example compound No. | Applied voltage (V) | Luminance (cd/m$^2$) | Maximum luminance (cd/m$^2$) | Efficiency (lm/W) |
|---|---|---|---|---|---|
| 5 | [1]-16 | 7 | 680 | 5000 | 0.57 |
| 6 | [1]-49 | 6 | 880 | 6700 | 0.75 |
| 7 | [1]-60 | 6 | 840 | 6100 | 0.83 |
| 8 | [1]-92 | 6 | 900 | 6600 | 0.77 |
| 9 | [1]-95 | 6 | 1000 | 6800 | 0.85 |
| 10 | [1]-158 | 6 | 820 | 6400 | 0.72 |
| 11 | [2]-17 | 6 | 820 | 5700 | 0.80 |
| 12 | [2]-65 | 6 | 980 | 6800 | 0.87 |
| 13 | [2]-85 | 6 | 810 | 5900 | 0.68 |

EXAMPLE 14

A device was formed in the same way as in Example 4 except that example compound No. [1]-60 and example compound No. [3]-1 were co-deposited (5:100 in weight ratio) to form 20 nm-thick light-emitting layer 3.

6V was applied to the thus obtained device by using an ITO electrode (anode 2) as a positive electrode and an Al—Li electrode (cathode 4) as a negative electrode. As the result, blue luminescence of 4200 cd/m² of luminance, maximum luminance of 9600 cd/m², and luminescence efficiency 1.20 lm/W were observed.

EXAMPLES 15 TO 23

Devices were formed in the same way as in Example 10 except that example compound [1]-60 was replaced with the example compounds shown in Table 15 and evaluated in the same way. The results are shown in Table 15.

TABLE 15

| Example | Example compound No. | Applied voltage (V) | Luminance (cd/m²) | Maximum luminance (cd/m²) | Efficiency (lm/W) |
|---|---|---|---|---|---|
| 15 | [1]-6 | 7 | 2900 | 6500 | 0.67 |
| 16 | [1]-47 | 6 | 6800 | 17200 | 1.74 |
| 17 | [1]-49 | 6 | 6300 | 16600 | 1.62 |
| 18 | [1]-80 | 6 | 5100 | 11500 | 1.30 |
| 19 | [1]-91 | 6 | 5200 | 13100 | 1.42 |
| 20 | [1]-99 | 6 | 6900 | 16500 | 1.80 |
| 21 | [2]-17 | 6 | 4600 | 11700 | 1.28 |
| 22 | [2]-65 | 6 | 6100 | 14200 | 1.52 |
| 23 | [2]-85 | 6 | 5100 | 11900 | 1.39 |

EXAMPLE 24

A device was formed in the same way as in Example 4 except that example compound No. [1]-43 and example compound No. [3]-15 were co-deposited (5:100 in weight ratio) to form 20 nm-thick light-emitting layer 3.

6V was applied to the thus obtained device by using an ITO electrode (anode 2) as a positive electrode and an Al—Li electrode (cathode 4) as a negative electrode. As the result, blue luminescence of 3900 cd/m² of luminance, maximum luminance of 10500 cd/m², and luminescence efficiency 1.12 lm/W were observed.

EXAMPLE 25

A device was formed in the same way as in Example 24 except that example compound No. [1]-43 was replaced with example compound No. [2]-40.

The thus obtained device along with an ITO electrode (anode 2) as a positive electrode and an Al—Li electrode (cathode 4) as a negative electrode was used on the applied voltage of 6 V, and blue luminescence of 4200 cd/m² of luminance, maximum luminance of 13100 cd/m², and luminescence efficiency 1.125 lm/W were observed.

EXAMPLE 26

A device was formed in the same way as in Example 4 except that example compound No. [1]-92 and example compound No. [4]-1 were co-deposited (5:100 in weight ratio) to form 20 nm-thick light-emitting layer 3.

6V was applied to the thus obtained device by using an ITO electrode (anode 2) as a positive electrode and an Al—Li electrode (cathode 4) as a negative electrode. As the result, blue luminescence of 6000 cd/m² of luminance, maximum luminance of 12200 cd/m², and luminescence efficiency 1.45 lm/W was observed.

EXAMPLES 27 TO 30

Devices were formed in the same way as in Example 26 except that example compound No. [1]-92 was replaced with the example compounds shown in Table 6 and evaluated in the same way. The results are shown in Table 16.

TABLE 16

| Example | Example compound No. | Applied voltage (V) | Luminance (cd/m²) | Maximum luminance (cd/m²) | Efficiency (lm/W) |
|---|---|---|---|---|---|
| 27 | [1]-66 | 6 | 5600 | 11800 | 1.33 |
| 28 | [1]-158 | 6 | 3900 | 9800 | 1.17 |
| 29 | [2]-17 | 6 | 5300 | 14100 | 1.47 |
| 30 | [2]-65 | 6 | 6600 | 15400 | 1.61 |

EXAMPLE 31

A device was formed in the same way as in Example 4 except that example compound No. [1]-60 and the above-mentioned example compound No. [5]-1 were co-deposited (5:100 in weight ratio) to form 20 nm-thick light-emitting layer 3.

6V was applied to the thus obtained device by using an ITO electrode (anode 2) as a positive electrode and an Al—Li electrode (cathode 4) as a negative electrode. As the result, blue luminescence of 4500 cd/m² of luminance, maximum luminance of 13700 cd/m², and luminescence efficiency 1.35 lm/W were observed.

EXAMPLE 32

A device was formed in the same way as in Example 31 except that example compound No. [1]-60 was replaced with example compound No. [2]-40.

6V was applied to the thus obtained device by using an ITO electrode (anode 2) as a positive electrode and an Al—Li electrode (cathode 4) as a negative electrode. As the result, blue luminescence of 4900 cd/m² of luminance, maximum luminance of 15200 cd/m², and luminescence efficiency 1.45 lm/W were observed.

EXAMPLE 33

A device was formed in the same way as in Example 4 except that example compound No. [1]-60 and example compound No. [6]-2 were co-deposited (5:100 in weight ratio) to form 20 nm-thick light-emitting layer 3.

6V was applied to the thus obtained device along with an ITO electrode (anode 2) as a positive electrode and an Al—Li electrode (cathode 4) as a negative electrode. As the result, blue luminescence of 4700 cd/m² of luminance, maximum luminance of 15800 cd/m², and luminescence efficiency 1.65 lm/W were observed.

EXAMPLE 34

A device was formed in the same way as in Example 33 except that example compound No. [6]-2 was replaced with example compound No. [6]-9.

6V was applied to the thus obtained device by using an ITO electrode (anode 2) as a positive electrode and an Al—Li electrode (cathode 4) as a negative electrode. As the result, blue luminescence of 5900 cd/m² of luminance, maximum luminance of 18200 cd/m², and luminescence efficiency 1.85 lm/W were observed.

EXAMPLE 35

A device was formed in the same way as in Example 4 except that example compound No. [1]-92 and the above-mentioned example compound No. [7]-1 were co-deposited (5:100 in weight ratio) to form 20 nm light-emitting layer 3.

6V was applied to the thus obtained device by using an ITO electrode (anode 2) as a positive electrode and an Al—Li electrode (cathode 4) as a negative electrode. As the result, blue luminescence of 5100 cd/m² of luminance, maximum luminance of 12300 cd/m², and luminescence efficiency 1.38 lm/W were observed.

EXAMPLES 36 TO 43

The luminescence spectra of the devices formed in Examples 4, 15, 21, 26, 31, 33, 34 and 35 were observed by MCPD-7000 and the CIE chromaticity coordinates were measured. The results are shown in Table 17.

TABLE 17

| Example | Device example No. | CIE chromaticity coordinate (x, y) |
|---------|--------------------|-----------------------------------|
| 36 | 4 | 0.15, 0.10 |
| 37 | 15 | 0.15, 0.10 |
| 38 | 21 | 0.15, 0.11 |
| 39 | 26 | 0.15, 0,10 |
| 40 | 31 | 0.16, 0.10 |
| 41 | 33 | 0.15, 0.09 |
| 42 | 34 | 0.15, 0.09 |
| 43 | 35 | 0.15, 0.11 |

EXAMPLE 44

A device was formed in the same way as in Example 4 except that example compound No. [7]-1 and example compound No. [2]-65 were co-deposited (5:100 in weight ratio) to form 20 nm-thick light-emitting layer 3.

6V was applied to the thus obtained device by using an ITO electrode (anode 2) as a positive electrode and an Al—Li electrode (cathode 4) as a negative electrode. As the result, blue luminescence of 4700 cd/m² of luminance, maximum luminance of 11100 cd/m², and luminescence efficiency 1.30 lm/W were observed.

EXAMPLE 45

A device was formed in the same way as in Example 4 except that example compound No. [1]-43 and example compound No. [2]-65 were co-deposited (5:100 in weight ratio) to form 20 nm-thick light-emitting layer 3.

6V was applied to the thus obtained device by using an ITO electrode (anode 2) as a positive electrode and an Al—Li electrode (cathode 4) as a negative electrode. As the result, blue luminescence of 5900 cd/m² of luminance, maximum luminance of 12600 cd/m², and luminescence efficiency 1.39 lm/W were observed.

EXAMPLE 46

Voltage was applied to the device formed in Example 13 for 100 hours under nitrogen atmosphere while maintaining the current density at 7.0 mA/cm² and degradation in luminance was found to be small as the initial luminance of 480 cd/m² was changed to 420 cd/m² after 100 hours.

COMPARATIVE EXAMPLE 1

A device was formed in the same way as in Example 4 except that the following styryl compound was used as a light-emitting layer.

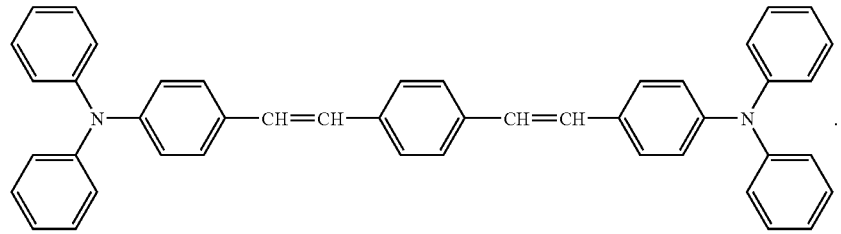

10V was applied to the thus obtained device by using an ITO electrode (anode 2) as a positive electrode and an Al—Li electrode (cathode 4) as a negative electrode. As the result, greenish blue white luminescence of 120 cd/m² of luminance, maximum luminance of 3800 cd/m², and luminescence efficiency 0.17 lm/W were observed.

COMPARATIVE EXAMPLE 2

A device was formed in the same way as in Example 4 except that the above styryl compound and example compound No. [4]-1 were co-deposited (5:100 in weight ratio) to form 20 nm-thick light-emitting layer 3.

10V was applied to the thus obtained device along with an ITO electrode (anode 2) as a positive electrode and an Al—Li electrode (cathode 4) as a negative electrode. As the result, greenish blue white luminescence of 125 cd/m² of luminance, maximum luminance of 4500 cd/m², and luminescence efficiency 0.30 lm/W were observed.

COMPARATIVE EXAMPLE 3

The luminescence spectrum of the device formed in Comparative Example 2 was observed by MCPD-7000 and the CIE chromaticity coordinate measured was (x,y)=(0.16, 0.30).

As described by way of embodiments and examples, the organic light-emitting device using the monoaminofluorene compound represented by the general formula [1] or [2] of the present invention, used in a single layer or in a mixed layer of dopant/host, enables high luminance luminescence when applied with a low voltage and is also excellent in color purity and durability. Furthermore, the device can be formed using vacuum evaporation, the casting method or the like, and a device having a large area can be readily produced at a relatively low cost.

The invention claimed is:
1. A monoaminofluorene compound selected from the following compounds:
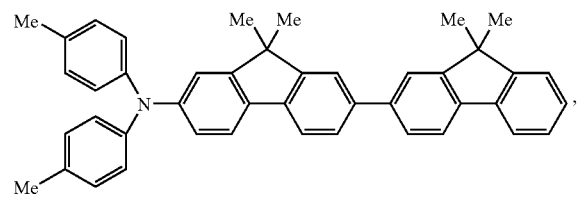
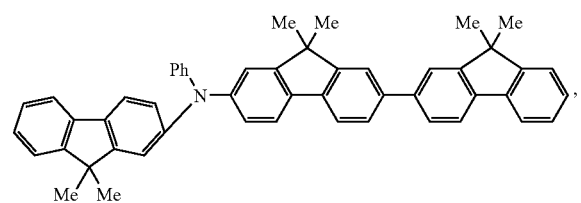
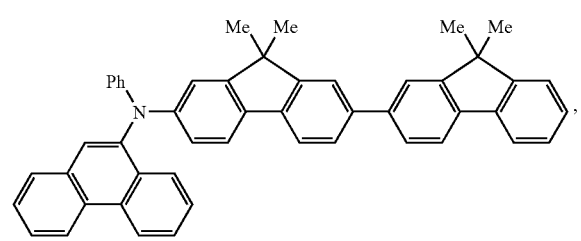
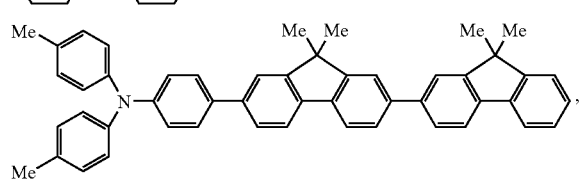
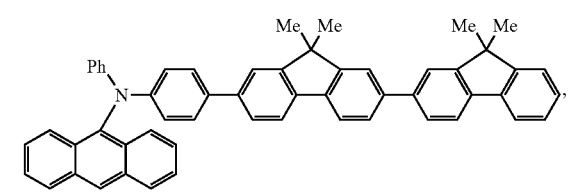
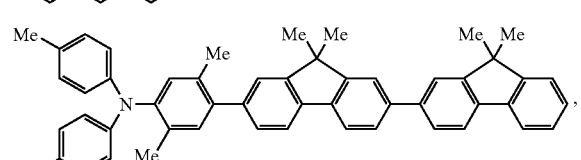
-continued
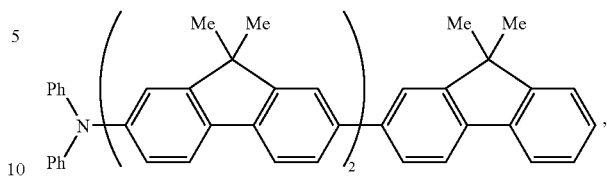
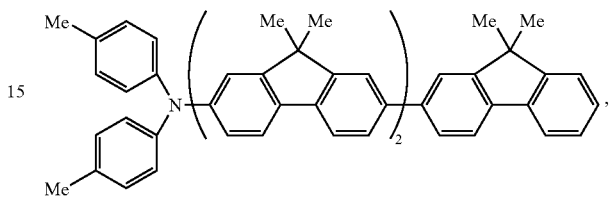
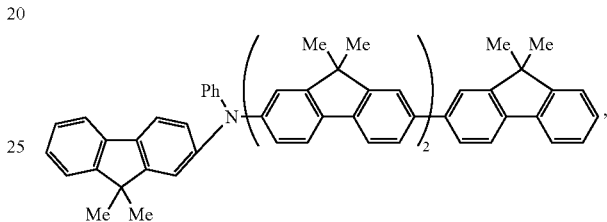
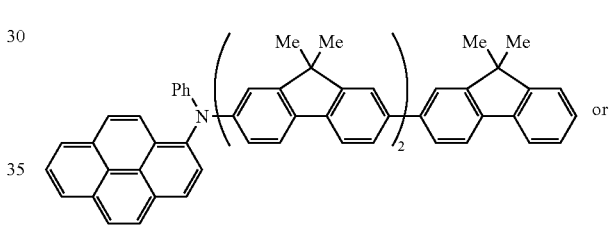
or
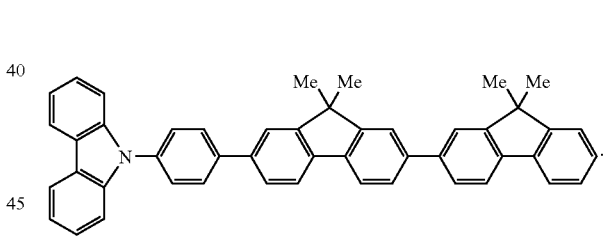
2. A monoaminofluorene compound selected from the following compounds:
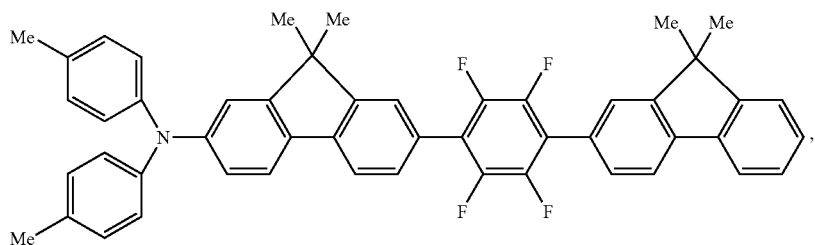

-continued

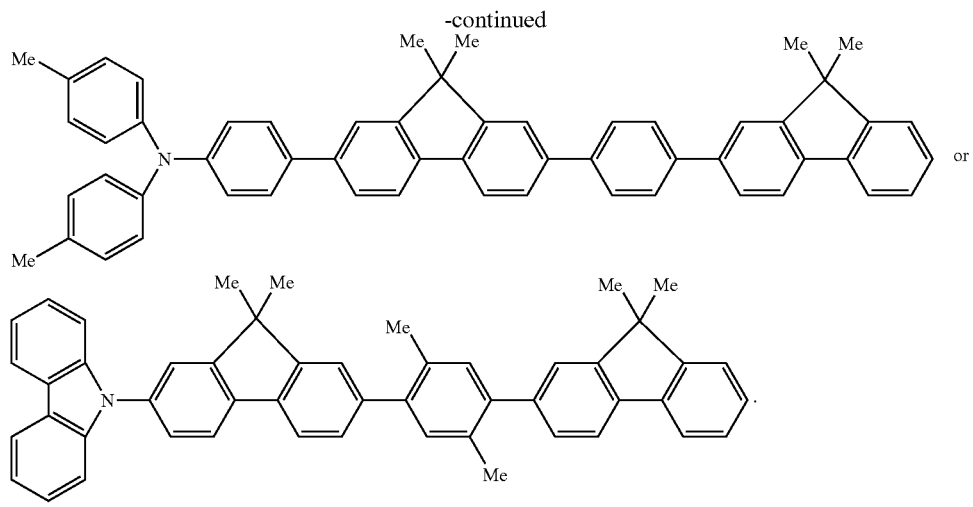

or

3. An organic light-emitting device comprising: a pair of electrodes which consist of an anode and a cathode, and one or more layers which are interposed between the electrodes and contain an organic compound, wherein at least one of the layers containing the organic compound is a light-emitting layer and contains at least one of the following compounds:

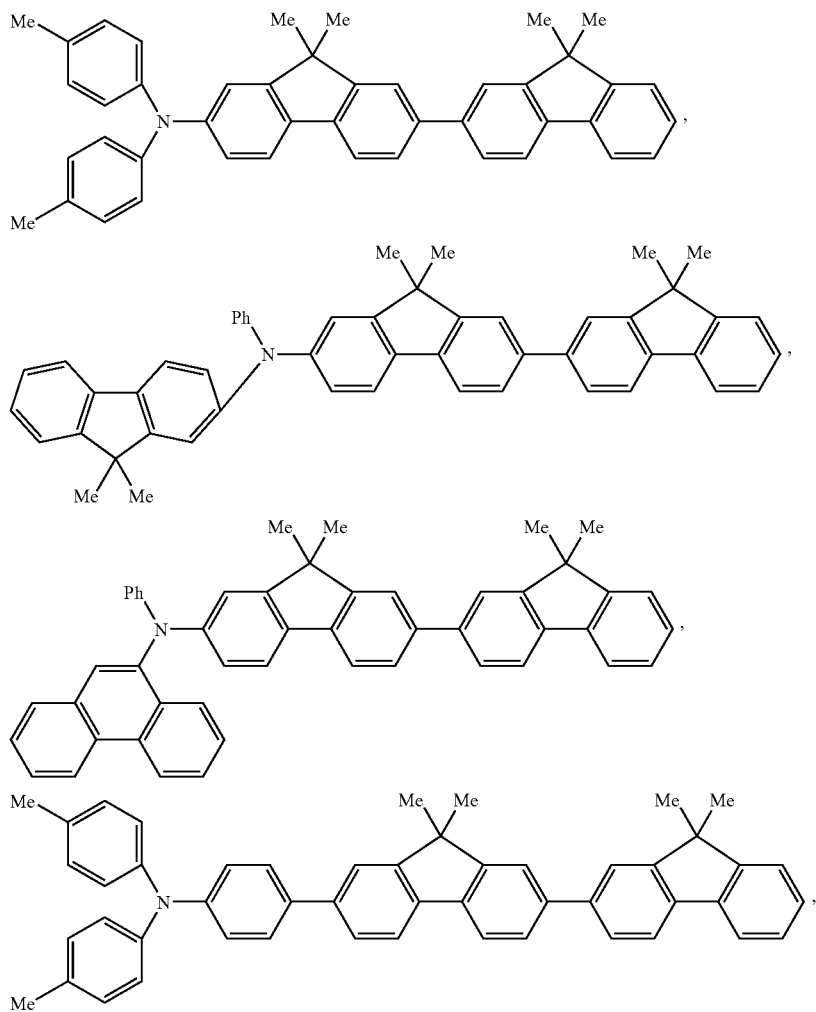

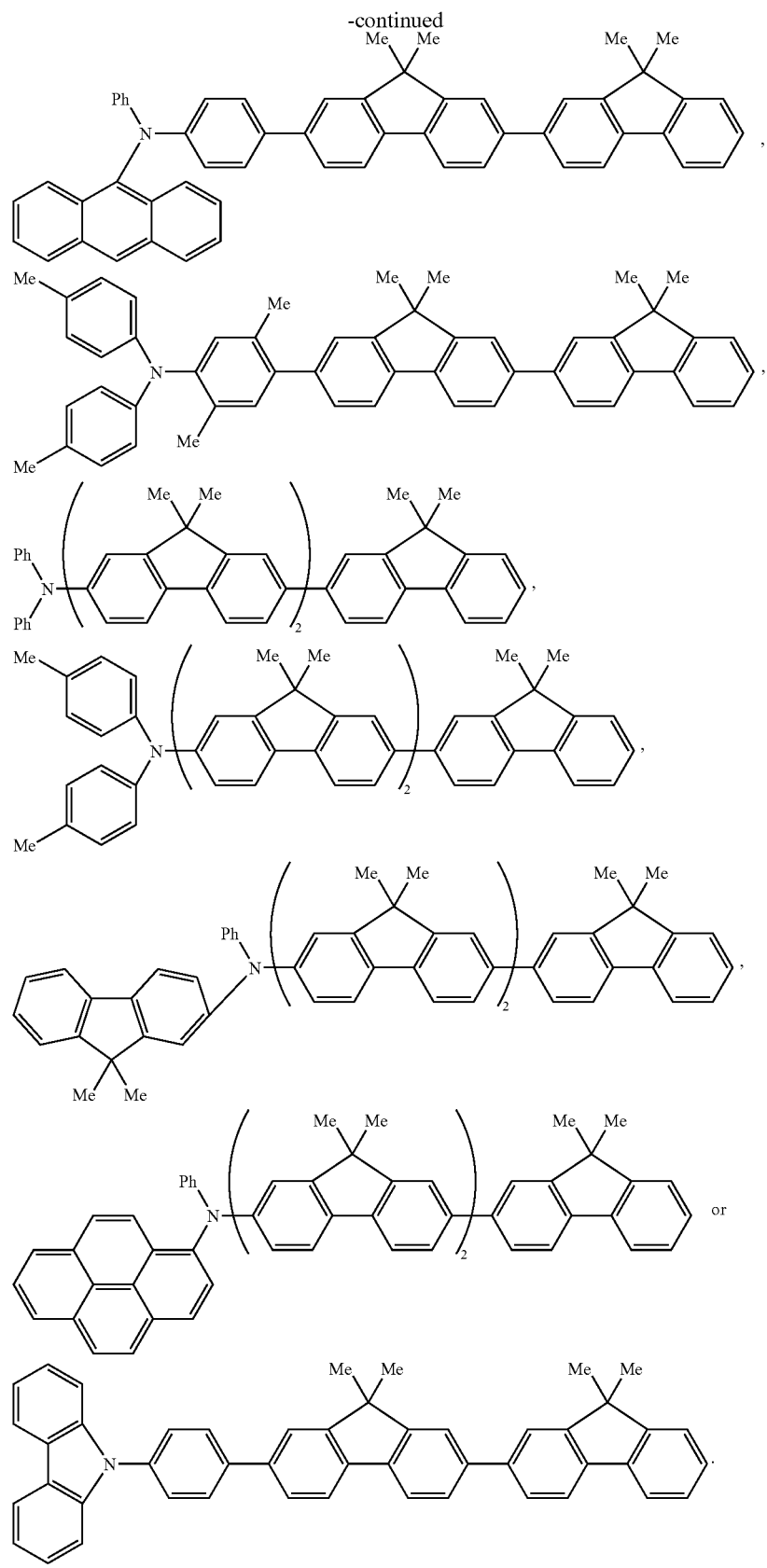

4. An organic light-emitting device comprising: a pair of electrodes which consist of an anode and a cathode, and one or more layers which are interposed between the electrodes and contain an organic compound, wherein at least one of the layers containing the organic compound is a light-emitting layer and contains at least one of the following compounds:

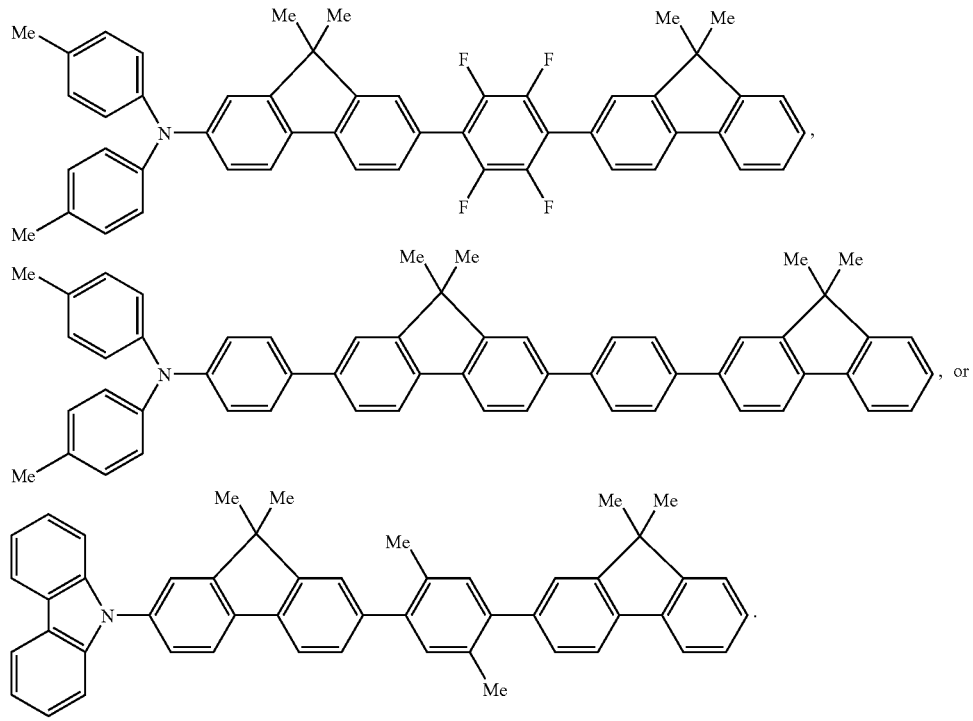

5. The organic light-emitting device according to claim 3, wherein the layer containing the organic compound contains at least one additional compound represented by the following general formula [3]:

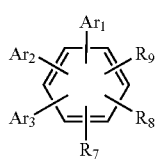

[3]

where $Ar_1$ to $Ar_3$ may be the same or different and are groups selected from the group consisting of substituted or unsubstituted aryl and heterocyclic ring groups, and either one of them may be a hydrogen atom, a substituted or unsubstituted alkyl group, or a substituted or unsubstituted aralkyl group; and

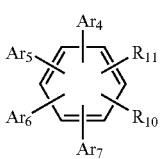

[4]

where $Ar_4$ to $Ar_7$ may be the same or different and are groups selected from the group consisting of substituted or unsubstituted aryl and heterocyclic ring groups; and $R_{10}$ and $R_{11}$ are groups selected from the group consisting of a hydrogen atom, a halogen group, substituted or unsubstituted alkyl and aralkyl groups, a substituted amino group and a cyano group.

6. The organic light-emitting device according to claim 4, wherein the layer containing the organic compound contains at least one additional compound represented by the following general formula [3]:

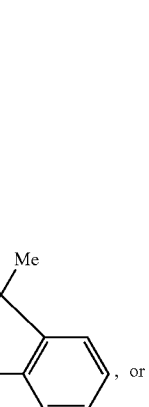

[3]

where $Ar_1$ to $Ar_3$ may be the same or different and are groups selected from the group consisting of substituted or unsubstituted aryl and heterocyclic ring groups, and either one of them may be a hydrogen atom, a substituted or unsubstituted alkyl group, or a substituted or unsubstituted aralkyl group; and $R_7$ to $R_9$ are groups selected from the group consisting of a hydrogen atom, a halogen group, substituted or unsubstituted alkyl and aralkyl groups, a substituted amino group and a cyano group.

7. The organic light-emitting device according to claim 3, wherein the layer containing the organic compound contains at least one additional compound represented by the following general formula [4]:

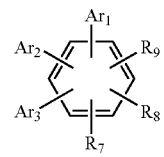

[5]

where $Ar_8$ to $Ar_{12}$ may be the same or different and are groups selected from the group consisting of substituted or unsubstituted aryl and heterocyclic ring groups; and $R_{12}$ is a group selected from the group consisting of a hydrogen atom, a halogen group, substituted or unsubstituted alkyl, aralkyl, aryl and heterocyclic ring groups, a substituted amino group and a cyano group.

8. The organic light-emitting device according to claim 4, wherein the layer containing the organic compound contains at least one additional compound represented by the following general formula [4]:

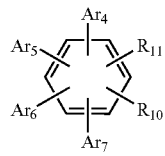
[4]

where $Ar_4$ to $Ar_7$ may be the same or different and are groups selected from the group consisting of substituted or unsubstituted aryl and heterocyclic ring groups; and $R_{10}$ and $R_{11}$ are groups selected from the group consisting of a hydrogen atom, a halogen group, substituted or unsubstituted alkyl and aralkyl groups, a substituted amino group and a cyano group.

9. The organic light-emitting device according to claim 3, wherein the layer containing the organic compound contains at least one additional compound represented by the following general formula [5]:

$R_7$ to $R_9$ are groups selected from the group consisting of a hydrogen atom, a halogen group, substituted or unsubstituted alkyl and aralkyl groups, a substituted amino group and a cyano group.

10. The organic light-emitting device according to claim 4, wherein the layer containing the organic compound contains at least one additional compound represented by the following general formula [5]:

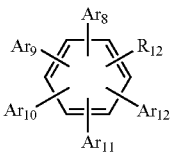
[5]

where $Ar_8$ to $Ar_{12}$ may be the same or different and are groups selected from the group consisting of substituted or unsubstituted aryl and heterocyclic ring groups; and $R_{12}$ is a group selected from the group consisting of a hydrogen atom, a halogen group, substituted or unsubstituted alkyl, aralkyl, aryl and heterocyclic ring groups, a substituted amino group and a cyano group.

11. The organic light-emitting device according to claim 3, wherein the layer containing the organic compound contains at least one additional compound represented by the following general formula [6]:

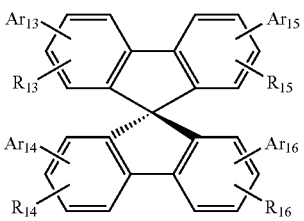
[6]

where $Ar_{13}$ to $Ar_{16}$ may be the same or different and are groups selected from the group consisting of substituted or unsubstituted aryl and heterocyclic ring groups, and up to any three of them may be a hydrogen atom, a halogen group, a substituted or unsubstituted alkyl group and a substituted or unsubstituted aralkyl group; and $R_{13}$ to $R_{16}$ are groups selected from the group consisting of a hydrogen atom, a halogen group, substituted or unsubstituted alkyl, aralkyl, aryl and heterocyclic ring groups, a substituted amino group and a cyano group.

12. The organic light-emitting device according to claim 4, wherein the layer containing the organic compound contains at least one additional compound represented by the following general formula [6]:

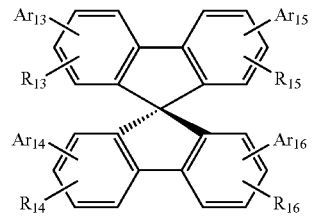
[6]

where $Ar_{13}$ to $Ar_{16}$ may be the same or different and are groups selected from the group consisting of substituted or unsubstituted aryl and heterocyclic ring groups, and up to any three of them may be a hydrogen atom, a halogen group, a substituted or unsubstituted alkyl group and a substituted or unsubstituted aralkyl group; and $R_{13}$ to $R_{16}$ are groups selected from the group consisting of a hydrogen atom, a halogen group, substituted or unsubstituted alkyl, aralkyl, aryl and heterocyclic ring groups, a substituted amino group and a cyano group.

13. The organic light-emitting device according to claim 3, wherein the layer containing the organic compound contains at least one additional compound represented by the following general formula [7]:

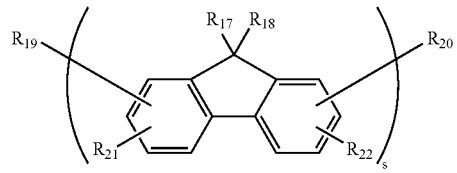
[7]

where $R_{17}$ and $R_{18}$ are groups selected from the group consisting of a hydrogen atom and substituted or unsubstituted alkyl, aralkyl and aryl groups, and $R_{17}$ and $R_{18}$ bound to different fluorene moieties may be the same or different and $R_{17}$ and $R_{18}$ bound to the same fluorene moiety may be the same or different; and $R_{19}$ to $R_{22}$ are groups selected from the group consisting of a hydrogen atom, a halogen group, substituted or unsubstituted alkyl and aralkyl and alkoxy groups, a substituted silyl group and a cyano group; and s is an integer of 2 to 5.

14. The organic light-emitting device according to claim 4, wherein the layer containing the organic compound contains at least one additional compound represented by the following general formula [7]:

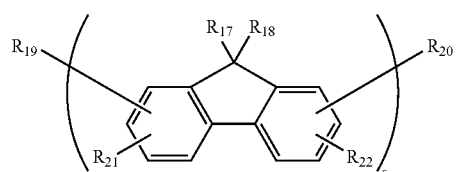
[7]

where $R_{17}$ and $R_{18}$ are groups selected from the group consisting of a hydrogen atom and substituted or unsubstituted alkyl, aralkyl and aryl groups, and $R_{17}$ and $R_{18}$ bound to different fluorene moieties may be the same or different and $R_{17}$ and $R_{18}$ bound to the same fluorene moiety may be the same or different; $R_{19}$ to $R_{22}$ are groups selected from the group consisting of a hydrogen atom, a halogen group, substituted or unsubstituted alkyl and aralkyl and alkoxy groups, a substituted silyl group and a cyano group; and s is as integer of 2 to 5.

* * * * *